US008927591B2

(12) United States Patent
Ho et al.

(10) Patent No.: US 8,927,591 B2
(45) Date of Patent: Jan. 6, 2015

(54) THIOCHROMENE DERIVATIVES AS HIF HYDROXYLASE INHIBITORS

(75) Inventors: Wen-Bin Ho, Los Altos, CA (US); Lee R. Wright, Redwood City, CA (US); Eric D. Turtle, Belmont, CA (US); Craig Mossman, Saratoga, CA (US); Lee A. Flippin, Woodside, CA (US)

(73) Assignee: Fibrogen, Inc., San Francisco, CA (US)

( * ) Notice: Subject to any disclaimer, the term of this patent is extended or adjusted under 35 U.S.C. 154(b) by 317 days.

(21) Appl. No.: 13/128,620

(22) PCT Filed: Nov. 11, 2009

(86) PCT No.: PCT/US2009/064065
§ 371 (c)(1),
(2), (4) Date: Aug. 22, 2011

(87) PCT Pub. No.: WO2010/056767
PCT Pub. Date: May 20, 2010

(65) Prior Publication Data
US 2011/0305776 A1    Dec. 15, 2011

Related U.S. Application Data

(60) Provisional application No. 61/114,971, filed on Nov. 14, 2008.

(51) Int. Cl.
A61K 31/382     (2006.01)
C07D 335/06    (2006.01)
C07D 409/04    (2006.01)

(52) U.S. Cl.
CPC ............ C07D 335/06 (2013.01); C07D 409/04 (2013.01)
USPC ............................................ 514/432; 549/23

(58) Field of Classification Search
CPC ........................... C07D 335/06; A61K 31/382
USPC .............................. 514/437, 432; 549/27, 23
See application file for complete search history.

(56) References Cited

U.S. PATENT DOCUMENTS

| 3,989,704 A | 11/1976 | Houlihan et al. |
| 4,036,964 A | 7/1977 | Buckle et al. |
| 4,260,611 A | 4/1981 | Bartmann et al. |
| 4,303,664 A | 12/1981 | Ono et al. |
| 4,559,403 A | 12/1985 | Bruderer et al. |
| 4,584,379 A | 4/1986 | Wagner |
| 4,673,682 A | 6/1987 | Konz et al. |
| 4,822,800 A | 4/1989 | Falotico et al. |
| 4,952,588 A | 8/1990 | Glamkowski et al. |
| 4,966,906 A | 10/1990 | Glamkowski et al. |
| 5,378,720 A | 1/1995 | Hlasta et al. |
| 5,620,995 A | 4/1997 | Weidmann et al. |
| 5,658,933 A | 8/1997 | Weidmann et al. |
| 5,719,164 A | 2/1998 | Weidmann et al. |
| 5,955,604 A | 9/1999 | Tsien et al. |
| 6,093,730 A | 7/2000 | Weidmann et al. |
| 6,291,162 B1 | 9/2001 | Tsien et al. |
| 6,319,931 B1 | 11/2001 | Kroemer et al. |
| 6,358,973 B1 | 3/2002 | Napoletano et al. |
| 6,358,976 B1 | 3/2002 | Wityak et al. |
| 6,369,053 B1 | 4/2002 | Yuan et al. |
| 6,762,318 B2 | 7/2004 | Kodra et al. |
| 6,777,425 B2 | 8/2004 | Burli et al. |
| 6,903,114 B2 | 6/2005 | Backstrom et al. |
| 7,208,601 B2 | 4/2007 | Mjalli et al. |
| 7,248,053 B2 | 7/2007 | Houldsworth |
| 7,294,457 B2 | 11/2007 | Kukolj et al. |
| 7,304,168 B2 | 12/2007 | Li et al. |
| 7,323,475 B2 | 1/2008 | Arend et al. |
| 7,622,503 B2 | 11/2009 | Dalton et al. |
| 7,629,357 B2 | 12/2009 | Arend et al. |
| 7,696,223 B2 | 4/2010 | Deng et al. |
| 7,713,986 B2 | 5/2010 | Seeley et al. |
| 7,863,292 B2 | 1/2011 | Arend et al. |
| 7,928,120 B2 | 4/2011 | Arend et al. |
| 8,017,625 B2 | 9/2011 | Arend et al. |
| 8,124,582 B2 | 2/2012 | Guenzler-Pukall et al. |
| 8,217,043 B2 | 7/2012 | Deng et al. |
| 8,269,008 B2 | 9/2012 | Arend et al. |
| 8,278,325 B2 | 10/2012 | Arend et al. |
| 8,324,405 B2 | 12/2012 | Ho et al. |
| 8,338,401 B2 | 12/2012 | Xu et al. |
| 2003/0153503 A1 | 8/2003 | Klaus et al. |
| 2003/0176317 A1 | 9/2003 | Guenzler-Pukall et al. |
| 2004/0235082 A1 | 11/2004 | Fourney et al. |
| 2005/0020487 A1 | 1/2005 | Klaus et al. |
| 2006/0178316 A1 | 8/2006 | Klaus et al. |

(Continued)

FOREIGN PATENT DOCUMENTS

| CA | 2134866 | 5/1995 |
| EP | 532466 | 3/1993 |

(Continued)

OTHER PUBLICATIONS

King, Med. Chem., Principle and Practice (1994), pp. 206-208.*
U.S. Appl. No. 13/599,161, filed Aug. 30, 2012, Arend et al.
Balant et al, Metabolic Considerations, etc., in Manfred ed. Burger's Medicinal Chemistry and Drug Discovery, 5th ed. vol. 1: Principles and Practice, John Wiley & Sons, In.c, 1995.
Banker et al., "Modern Pharmaceuticals", 3rd Ed., p. 596 (1996).
Bickel et al., *Hepatology*, vol. 28:404-411 (1998).
Bonsignore et al., "Synthesis of 2H-1-benzopyran-2, 4(3H)-dione-3-carboxamide and 2H, 3H-[1] benzopyrano [4,3-b]pyrano-2-hydroxy-3-carboxamide-4, 5-dione derivatives via carbon", Heterocycles, vol. 45, No. 11,pp. 2131-2136 (1997).
Bruegge et al., "Hydroxylation of Hypoxia-Inducible Transcription Factors and Chemical Compounds Targeting the HIF-alpha Hydroxylases," Current Medicinal Chemistry, vol. 14, pp. 1853-1862, XP002517838 (2007).

(Continued)

Primary Examiner — Taofiq A Solola
(74) Attorney, Agent, or Firm — Sheppard Mullin Richter & Hampton LLP

(57) ABSTRACT

The present invention relates to novel compounds, methods, and compositions capable of decreasing HIF hydroxylase enzyme activity, thereby increasing the stability and/or activity of hypoxia inducible factor (HIF).

37 Claims, No Drawings

(56) References Cited

U.S. PATENT DOCUMENTS

| | | |
|---|---|---|
| 2006/0178317 A1 | 8/2006 | Klaus et al. |
| 2006/0183695 A1 | 8/2006 | Klaus et al. |
| 2006/0199836 A1 | 9/2006 | Turtle et al. |
| 2006/0251638 A1 | 11/2006 | Guenzler-Pukall et al. |
| 2006/0258660 A1 | 11/2006 | Guenzler-Pukall et al. |
| 2006/0258702 A1 | 11/2006 | Guenzler-Pukall et al. |
| 2006/0270699 A1 | 11/2006 | Guenzler-Pukall et al. |
| 2006/0276477 A1 | 12/2006 | Klaus et al. |
| 2007/0004627 A1 | 1/2007 | Seeley et al. |
| 2007/0155784 A1 | 7/2007 | Arend et al. |
| 2007/0292433 A1 | 12/2007 | Seeley et al. |
| 2007/0293575 A1 | 12/2007 | Seeley et al. |
| 2010/0330199 A1 | 12/2010 | Zhou et al. |
| 2011/0212959 A1 | 9/2011 | Arend |
| 2011/0305776 A1 | 12/2011 | Ho |
| 2012/0178755 A1 | 7/2012 | Arend et al. |

FOREIGN PATENT DOCUMENTS

| | | |
|---|---|---|
| EP | 0 304 158 | 6/1994 |
| EP | 0 626 378 | 11/1994 |
| EP | 626178 | 11/1994 |
| EP | 0 661 269 | 12/1994 |
| EP | 706795 | 4/1996 |
| EP | 0 650 960 | 5/1997 |
| EP | 0 650 961 | 5/1997 |
| EP | 0 911 340 | 4/1999 |
| EP | 1676834 | 7/2005 |
| JP | 07-224039 | 8/1995 |
| JP | 07-228571 | 8/1995 |
| JP | 11-302257 | 11/1999 |
| JP | 2005-524612 | 8/2005 |
| JP | 2006-514113 | 4/2006 |
| JP | 2006-137763 | 6/2006 |
| JP | 2006-527199 | 11/2006 |
| WO | WO-96/18616 | 6/1996 |
| WO | WO-98/50343 | 11/1998 |
| WO | WO-98/50346 | 11/1998 |
| WO | WO-01/58892 | 8/2001 |
| WO | WO-02/074981 | 9/2002 |
| WO | WO-02/100832 | 12/2002 |
| WO | WO-02/101073 | 12/2002 |
| WO | WO-03/007945 | 1/2003 |
| WO | WO-03/010141 | 2/2003 |
| WO | WO-03/014377 | 2/2003 |
| WO | WO-03/049686 | 6/2003 |
| WO | WO-03/053997 | 7/2003 |
| WO | WO-03/080566 | 10/2003 |
| WO | WO-2004/050082 | 6/2004 |
| WO | WO-2004/052284 | 6/2004 |
| WO | WO-2004/052285 | 6/2004 |
| WO | WO-2004/108121 | 12/2004 |
| WO | WO-2004/108681 | 12/2004 |
| WO | WO-2005/007192 | 1/2005 |
| WO | WO-2005/009962 | 2/2005 |
| WO | WO-2005/011696 | 2/2005 |
| WO | WO-2005/014533 | 2/2005 |
| WO | WO-2005/077915 | 8/2005 |
| WO | WO-2006/094292 | 9/2006 |
| WO | WO-2006/133391 | 12/2006 |
| WO | WO-2006/138511 | 12/2006 |
| WO | WO-2007/025169 | 3/2007 |
| WO | WO-2007/038571 | 4/2007 |
| WO | WO-2007/062664 | 6/2007 |
| WO | WO-2007/070359 | 6/2007 |
| WO | WO-2007/090068 | 8/2007 |
| WO | WO-2007/103905 | 9/2007 |
| WO | WO-2007/115315 | 10/2007 |
| WO | WO-2007/136990 | 11/2007 |
| WO | WO-2007/146425 | 12/2007 |
| WO | WO-2007/146438 | 12/2007 |
| WO | WO-2007/150011 | 12/2007 |
| WO | WO-2008/076425 | 6/2008 |
| WO | WO-2008/076427 | 6/2008 |
| WO | WO-2008/089051 | 7/2008 |
| WO | WO-2008/089052 | 7/2008 |
| WO | WO-2008/130508 | 10/2008 |
| WO | WO-2008/130600 | 10/2008 |
| WO | WO-2008/137060 | 11/2008 |
| WO | WO-2008/137084 | 11/2008 |
| WO | WO-2009/039321 | 3/2009 |
| WO | WO-2009/039322 | 3/2009 |
| WO | WO-2009/039323 | 3/2009 |
| WO | WO-2009/049112 | 3/2009 |
| WO | WO-2009/070644 | 6/2009 |
| WO | WO-2009/073497 | 6/2009 |
| WO | WO-2009/073669 | 6/2009 |
| WO | WO-2009/075822 | 6/2009 |
| WO | WO-2009/075826 | 6/2009 |
| WO | WO-2009/086044 | 7/2009 |
| WO | WO-2009/089547 | 7/2009 |
| WO | WO-2009/100250 | 8/2009 |
| WO | WO-2010/022240 | 2/2010 |
| WO | WO-2010/056767 | 5/2010 |
| WO | WO-02/070510 | 9/2012 |

OTHER PUBLICATIONS

Bruick et al., A Conserved Family of Proly-4-Hydroylases That Modify HIF, Science, vol. 294, pp. 1337-1340, (2001).

Cockman et al., J. Biol. Chem., vol. 275: pp. 25733-25741 (2000).

Cunliffe et al., Novel Inhibitors of Prolyl 4-Hydroxylase 3 Inhibition by the Substrate Analogue N-Oxaloglycine and Its Derivatives, J. Med. Chem., vol. 35, pp. 2652-2658, (1992).

Dorwald F. A. Side Reactions in Organic Synthesis, 2005, Wiley: VCH, Weinheim p. IX of Preface p. 1-15.

Duro et al., Sintesi Ed Attivita Farmacologica D1 Ammmino-E Dialchilamminoalchilammidi-D1 Derivati Della 3-Carbossi-4-Fenillisochinolina, Ed. Sc., vol. 36, pp. 400-411, (1980) (Abstract in English).

Franklin, et al. "Approaches to the design of anti-fibrotic drugs" Biochem. Soc. Trans. 19(4): 812-815 (1991).

Franklin et al., Biochem J., vol. 353:333-338 (2001).

Freshney (Culture of Animal Cells, A Manual of Basic Technique, Alan R. Liss, Inc., 1983, New York, p. 4.

Friedman et al. Proc. Natl. Acad. Sci. USA, 97:4736-4741 (2000).

Guo et al., Selective Protection of 2',2'-Difluorodeoxycytidine (Gemcitabine), J. Org. Chem., vol. 64, pp. 8319-8322, (1999).

Iliopoulus et al., Proc. Natl. Acad. Sci. USA, 93:10595-10599 (1996).

Ivan et al., HIFa Targeted for VHL-Mediated Destruction by Proline Hydroxylation: Implications for O2 Sensing, Science, 292:464-468, (2001).

Jaakkola et al., Targeting of HIF-alpha to the von Hippel-Lindau Ubiquitylation Complex by O2-Regulated Prolyl Hydroxylation, Science, 292(5516):468-472, (2001).

Jiang et al., J. Biol. Chem., 271:17771-17778 (1996).

Kivirikko et al. Matrix Biol., 16:357-368 (1998).

Lando et al., Oxygen-Dependent Regulation of Hypoxia-Inducible Factors by Polyl and Asparaginyl Hydroxylation, Eur. J. Biochem, 270:781-790, (2003).

Majamaa et al. Biochem J., 229:127-133 (1985).

Majamaa et al. Eur. J. Biochem., 138:239-245 (1984).

Maxwell et al., Nature, 399:271-275 (1999).

Patani et al., "Bioisosterism: A Rational Approach in Drug Design," Chemical Reviews 96(8):3158-3159 (1996).

Rabinowitz et al., Annual Reports in Medicinal Chemistry, 2010, 45, 123-139.

Richard et al., Nonhypoxic Pathway Mediates the Induction of Hypoxia-Inducible Factor 1a in Vascular Smooth Muscle Cells, J. Bio. Chem., 275:26765-26771, (2000).

Safran, et al. "HIF hydroxylation and the mammalian oxygen-sensing pathway" J. Clin. Invest. 111(6):779-783 (2003).

Sandau, et al. "Induction of Hypoxia-Inducible-Factor 1 by Nitric Oxide is Mediated via the P1 3K Pathway" Biochem. Biophys. Res. Commun., 278:263-267 (2000).

Sato et al. "Stability and Physicochemical Properties of Viracept Tablets" Antibiotics and Chemotherapy 14(9):1589-1592 (1998)— English Translation Not Available.

(56) References Cited

OTHER PUBLICATIONS

Sodhi, et al. "MAPK and Akt Act Cooperatively but Independently on Hypoxia Inducible Factor-1α in rasV12 Unpregulation of VEGF" Biochem.Biophys. Res.Commun., 287:292-300 (2001).
Sutter et al., *Proc. Natl. Acad. Sci. USA*, 97:4748-4753 (2000).
Tacchini, et al. "Hepatocyte growth factor signaling stimulates hypoxia inducible factor-1 (HIF-1) activity in HepG2 hepatoma cells" Carcinogenesis, 22:1363-1371 (2001).
Tanimoto et al., *EMBO J*, 19:4298-4309 (2000).
Testa, "Prodrug Research, etc . . . ," Biochemical Pharmacology 68: 2097-2106 (2004).
Venkatesh et al., Role of the Development Scientist in Compound Lead Selection and Optimization J. Pharm. Sci. 89, 145-154 (2000).
Vippagunta et al., "Crystalline Solids", Adv. Drug Del. Rev., 48 (2001) 3-26.
Wermuth, "Molecular Variations Based on Isosteric Replacements," The Practice of Medicinal Chemistry, Elsevier, pp. 189-214, XP009112544 (2003).
Wolff, M.E., "Burger's Medicinal Chemistry", 5th Ed., Part 1, pp. 975-977 (1995).
Wolff, Burger's Medicinal Chemistry and Drug Discovery, vol. 1, Principles and Practice, John Wiley & sons, New York, 1997.
Wu et al., Regulatory Perspective of Type II Prodrug Development and Time-Dependent Toxicity Mangagement: Nonclinical Pharm/Tox Analysis and the Role of Comparative Toxicology, Toxicology, 236, pp. 1-6, (2007).
Xia et al. European Journal of Medicinal Chemistry 49 (2012) 24-40.

\* cited by examiner

THIOCHROMENE DERIVATIVES AS HIF HYDROXYLASE INHIBITORS

CROSS REFERENCE TO RELATED APPLICATIONS

This application is a National Phase application under 35 U.S.C. §371 of PCT Application PCT/US2009/064065, filed Nov. 11, 2009, which claims the benefit under 35 U.S.C. §119(e) from U.S. Provisional Application Ser. No. 61/114,971, filed Nov. 14, 2008, which are hereby incorporated by reference in their entirety.

BACKGROUND OF THE INVENTION

1. Field of the Invention

The present invention relates to novel compounds, methods, and compositions capable of decreasing HIF hydroxylase enzyme activity, thereby increasing the stability and/or activity of hypoxia inducible factor (HIF).

2. State of the Art

Hypoxia inducible factor (HIF) is a basic helix-loop-helix (bHLH) PAS (Per/Arnt/Sim) transcriptional activator that mediates changes in gene expression in response to changes in cellular oxygen concentration. HIF is a heterodimer containing an oxygen-regulated α-subunit (HIFα), and a constitutively expressed β-subunit (HIFβ/ARNT). In oxygenated (normoxic) cells, HIFα subunits are rapidly degraded by a mechanism that involves ubiquitination by the von Hippel-Lindau tumor suppressor (pVHL) E3 ligase complex. Under hypoxic conditions, HIFα is not degraded, and an active HIFα/β complex accumulates in the nucleus, and activates the expression of several genes including glycolytic enzymes, glucose transporters, erythropoietin (EPO), and vascular endothelial growth factor (VEGF). (Jiang et al. (1996) *J. Biol. Chem.* 271:17771-17778; Iliopoulus et al. (1996) *Proc. Natl. Acad. Sci. USA,* 93:10595-10599; Maxwell et al. (1999) *Nature* 399:271-275; Sutter et al. (2000) *Proc. Natl. Acad. Sci. USA* 97:4748-4753; Cockman et al. (2000) *J. Biol. Chem.* 275:25733-25741; and Tanimoto et al. (2000) *EMBO J.* 19:4298-4309.)

Levels of HIFα are elevated in most cells in response to hypoxia, and HIFα is induced in vivo when animals are subjected to anemia or hypoxia. HIFα levels rise within a few hours after the onset of hypoxia, and induce numerous beneficial cellular processes including cytoprotective effects, enhanced erythropoiesis, and physiological adaptation to ischemic or hypoxic states. Induction of HIFα is potentially beneficial in conditions such as heart attack, stroke, peripheral vascular disease, chronic ischemia, inflammation, and anemia.

HIFα levels are also increased by a number of factors that mimic hypoxia, including iron chelators such as desferrioxamine (DFO), and divalent metal salts such as $CoCl_2$. Additionally, several compounds originally identified as inhibitors of procollagen prolyl hydroxylase enzymes have been found to stabilize HIFα. Examples of such compounds can be found, e.g., in Majamaa et al. (1984) *Eur. J. Biochem.* 138:239-245; Majamaa et al. (1985) *Biochem. J.* 229:127-133; Kivirikko, and Myllyharju (1998) *Matrix Biol.* 16:357-368; Bickel et al. (1998) *Hepatology* 28:404-411; Friedman et al. (2000) *Proc. Natl. Acad. Sci. USA* 97:4736-4741; Franklin (1991) *Biochem. Soc. Trans.* 19):812-815; and Franklin et al. (2001) *Biochem. J.* 353:333-338. Additionally, compounds that inhibit HIF hydroxylases have been described in, e.g., International Publication Nos. WO 03/049686, WO 02/074981, WO 03/080566, WO 2004/108681, WO 2006/094292, WO 2007/038571, WO 2007/070359, WO 2007/090068, WO 2007/103905, WO 2007/115315, WO 2007/136990, WO 2007/150011, WO 2008/076425, WO 2008/076427, WO 2008/089051, WO 2008/089052, WO 2008/130600, WO 2008/130508, WO 2008/137084, WO 2008/137060, WO 2009/039321, WO 2009/039322, WO 2009/039323, WO 2009/049112, WO 2009/070644, WO2009/073497, WO 2009/073669, WO 2009/073669, and WO 2009/086044.

There remains a need for compounds that are effective in the treatment and prevention of conditions and disorders associated with HIF, including anemia and tissue damage caused by ischemia and/or hypoxia. The compounds provided herein inhibit HIF hydroxylase activity, thereby increasing the stability and/or activity of hypoxia inducible factor (HIF), and can be used to treat and prevent HIF-associated conditions and disorders.

SUMMARY OF THE INVENTION

The present invention is directed to novel compounds, and methods of using these compounds to inhibit HIF hydroxylase activity, thereby increasing the stability and/or activity of hypoxia inducible factor (HIF).

In one aspect, there are provided compounds of Formula I:

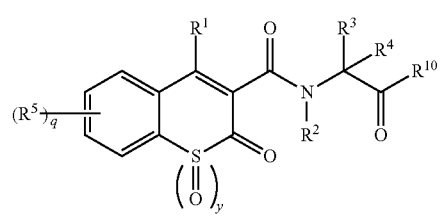

wherein:

q is 0, 1, 2, 3, or 4;

y is 0-2;

$R^1$ is selected from the group consisting of $—OR^{18}$, hydroxy, acyloxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, thio, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, amino, substituted amino, and acylamino;

$R^2$ is selected from the group consisting of hydrogen, alkyl, and substituted alkyl;

$R^3$ is selected from the group consisting of hydrogen, deuterium, alkyl, and substituted alkyl;

$R^4$ is selected from the group consisting of hydrogen, deuterium, and methyl;

each $R^5$ is independently selected from the group consisting of hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, cycloalkyl, substituted cycloalkyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heteroaryl, and substituted heteroaryl;

or two $R^5$ are taken together with the carbon atoms to which they are attached to form a 5- or 6-membered aryl or substituted aryl;

$R^{10}$ is —$NR^{11}R^{12}$ or —$OR^{13}$;

$R^{11}$ and $R^{12}$ are independently selected from the group consisting hydrogen, alkyl, alkylene-cycloalkyl, heterocyclic, and aryl;

or $R^{11}$ and $R^{12}$ are taken together with the nitrogen to which they are attached form a 5- or 6-membered heterocyclic, substituted heterocyclic, heteroaryl or substituted heteroaryl;

$R^{13}$ is selected from the group consisting of a cation, hydrogen and alkyl which is unsubstituted or substituted with one or more substituents independently selected from the group consisting of cycloalkyl, heterocyclic, aryl, and heteroaryl; and $R^{18}$ is a cation;

or a pharmaceutically acceptable salt, single stereoisomer, mixture of stereoisomers, ester, or prodrug thereof.

In another aspect, the invention is directed to compounds of Formula II:

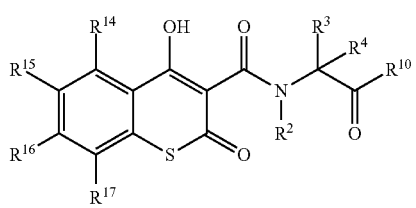

wherein:

$R^2$ is selected from the group consisting of hydrogen, alkyl, and substituted alkyl;

$R^3$ is selected from the group consisting of hydrogen, deuterium, alkyl, and substituted alkyl;

$R^4$ is selected from the group consisting of hydrogen, deuterium, and methyl;

$R^{14}$, $R^{15}$ $R^{16}$ and $R^{17}$ are independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, cycloalkyl, substituted cycloalkyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heteroaryl, and substituted heteroaryl;

or $R^{14}$ and $R^{15}$, $R^{15}$ and $R^{16}$, or $R^{16}$ and $R^{17}$ are taken together with the carbon atoms to which they are attached to form a 5- or 6-membered aryl or substituted aryl;

$R^{10}$ is —$NR^{11}R^{12}$ or —$OR^{13}$;

$R^{11}$ and $R^{12}$ are independently selected from the group consisting hydrogen, alkyl, alkylene-cycloalkyl, heterocyclic, and aryl;

or $R^{11}$ and $R^{12}$ are taken together with the nitrogen to which they are attached form a 5- or 6-membered heterocyclic, substituted heterocyclic, heteroaryl or substituted heteroaryl; and $R^{13}$ is selected from the group consisting of a cation, hydrogen and alkyl which is unsubstituted or substituted with one or more substituents independently selected from the group consisting of cycloalkyl, heterocyclic, aryl, and heteroaryl;

or a pharmaceutically acceptable salt, single stereoisomer, mixture of stereoisomers, ester, or prodrug thereof.

The invention also provides pharmaceutical compositions comprising one or more compounds of Formula I or II and a pharmaceutically acceptable excipient. In some embodiments, the composition further comprises or is used in combination with at least one additional therapeutic agent. In some embodiments, the agent is selected from the group consisting of vitamin $B_{12}$, folic acid, ferrous sulfate, recombinant human erythropoietin, and an erythropoiesis stimulating agent (ESA).

The invention is also directed to methods of treating, pretreating, or delaying onset or progression of a condition associated with or mediated, at least in part, by hypoxia inducible factor (HIF), the method comprising administering to a patient a therapeutically effective amount of a compound of Formula I or II, or a pharmaceutical composition comprising one or more compounds of Formula I or II. In one embodiment, the condition associated with or mediated by HIF is tissue damage associated with ischemia or hypoxia. In one aspect, the ischemia is associated with an event including, but not limited to, myocardial infarction, pulmonary embolism, intestinal infarction, ischemic stroke, renal ischemic-reperfusion injury, cardiac cirrhosis, transient ischemic attack, macular degeneration, chronic kidney failure, peripheral artery disease, and congestive heart failure.

The invention is also directed to methods of treating, pretreating, or delaying onset or progression of a condition associated with or mediated, at least in part, by erythropoietin (EPO), the method comprising administering to a patient a therapeutically effective amount of a compound of Formula I or II or a pharmaceutical composition comprising one or more compounds of Formula I or II.

The invention is also directed to methods of treating, pretreating, or delaying onset or progression of anemia, the method comprising administering to a patient a therapeutically effective amount of a compound of Formula I or II or a pharmaceutical composition comprising one or more compounds of Formula I or II.

The invention is also directed to methods of inhibiting the activity of at least one HIF hydroxylase, the method comprising bringing into contact the HIF hydroxylase and a compound of the invention. In one embodiment, the HIF hydroxylase is an asparaginyl hydroxylase such as Factor Inhibiting HIF (FIH). In another embodiment, the HIF hydroxylase is a prolyl hydroxylase including, but not limited to, a HIF prolyl hydroxylase selected from the group consisting of human EGLN1, EGLN2, or EGLN3, or an orthologous enzyme from another species.

DETAILED DESCRIPTION OF THE INVENTION

Before the present compositions and methods are described, it is to be understood that the invention is not limited to the particular compounds, compositions, methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

1. Compounds of the Invention

The invention is directed to compounds of Formula I:

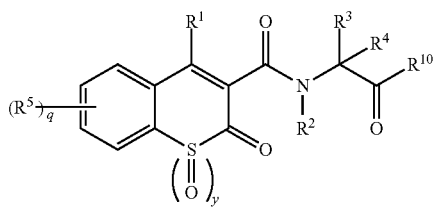

wherein:
q is 0, 1, 2, 3, or 4;
y is 0-2;
$R^1$ is selected from the group consisting of $-OR^{18}$, hydroxy, acyloxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, thio, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, amino, substituted amino, and acylamino;
$R^2$ is selected from the group consisting of hydrogen, alkyl, and substituted alkyl;
$R^3$ is selected from the group consisting of hydrogen, deuterium, alkyl, and substituted alkyl;
$R^4$ is selected from the group consisting of hydrogen, deuterium, and methyl;
each $R^5$ is independently selected from the group consisting of hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, cycloalkyl, substituted cycloalkyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heteroaryl, and substituted heteroaryl;
or two $R^5$ are taken together with the carbon atoms to which they are attached form a 5- or 6-membered aryl or substituted aryl;
$R^{10}$ is $-NR^{11}R^{12}$ or $-OR^{13}$;
$R^{11}$ and $R^{12}$ are independently selected from the group consisting hydrogen, alkyl, alkylene-cycloalkyl, heterocyclic, and aryl;
or $R^{11}$ and $R^{12}$ are taken together with the nitrogen to which they are attached form a 5- or 6-membered heterocyclic, substituted heterocyclic, heteroaryl or substituted heteroaryl;
$R^{13}$ is selected from the group consisting of a cation, hydrogen and alkyl which is unsubstituted or substituted with one or more substituents independently selected from the group consisting of cycloalkyl, heterocyclic, aryl, and heteroaryl; and
$R^{18}$ is a cation;
or a pharmaceutically acceptable salt, single stereoisomer, mixture of stereoisomers, ester, or prodrug thereof.

In certain embodiments, the invention is directed to compounds of Formula I:

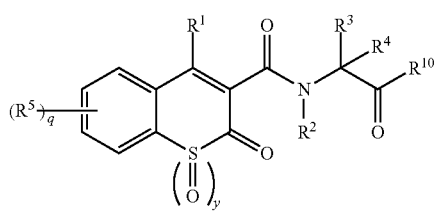

wherein:
q is 0, 1, 2, 3, or 4;
y is 0-2;
$R^1$ is selected from the group consisting of hydroxy, acyloxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, thio, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, amino, substituted amino, and acylamino;
$R^2$ is selected from the group consisting of hydrogen, alkyl, and substituted alkyl;
$R^3$ is selected from the group consisting of hydrogen, deuterium, alkyl, and substituted alkyl;
$R^4$ is selected from the group consisting of hydrogen, deuterium, and methyl;
each $R^5$ is independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heteroaryl, and substituted heteroaryl;
or two $R^5$ are taken together with the carbon atoms to which they are attached form a 5- or 6-membered aryl or substituted aryl;
$R^{10}$ is $-NR^{11}R^{12}$ or $-OR^{13}$;
$R^{11}$ and $R^{12}$ are independently selected from the group consisting hydrogen, alkyl, alkylene-cycloalkyl, heterocyclic, and aryl;
or $R^{11}$ and $R^{12}$ are taken together with the nitrogen to which they are attached form a 5- or 6-membered heterocyclic, substituted heterocyclic, heteroaryl or substituted heteroaryl; and
$R^{13}$ is selected from the group consisting of hydrogen and alkyl which is unsubstituted or substituted with one or more substituents independently selected from the group consisting of cycloalkyl, heterocyclic, aryl, and heteroaryl;

or a pharmaceutically acceptable salt, single stereoisomer, mixture of stereoisomers, ester, or prodrug thereof.

In certain embodiments of compounds of Formula I, y is 0. In certain embodiments, y is 1. In certain embodiments, y is 2.

In certain embodiments of compounds of Formula I, $R^1$ is hydroxy.

In certain embodiments of compounds of Formula I, $R^1$ is hydroxy and $R^2$ is hydrogen. In other embodiments, $R^1$ is hydroxy and $R^2$ and $R^4$ are hydrogen. In other embodiments, $R^1$ is hydroxy, $R^2$ and $R^4$ are hydrogen, and $R^3$ is hydrogen or methyl.

In certain embodiments of compounds of Formula I, q is 1 or 2.

In certain embodiments of compounds of Formula I, each $R^5$ is independently selected from the group consisting of halo, acylamino, alkyl, substituted alkyl, substituted alkynyl, cycloalkyl, aryl, substituted aryl, alkoxy, substituted alkoxy, heteroaryl, and substituted heteroaryl.

In other embodiments of compounds of Formula I, each $R^5$ is independently selected from the group consisting of hydrogen, halo, alkyl, substituted alkyl, aryl, substituted aryl, alkoxy, heteroaryl, and substituted heteroaryl.

In certain embodiments of compounds of Formula I, at least one $R^5$ is bromo, chloro, or fluoro. In certain embodiments, at least one $R^5$ is a $(C_1$-$C_3)$-alkyl, alkynyl, or cycloalkyl that is optionally substituted with an aryl. In another embodiment, at least one $R^5$ is methyl. In certain embodiments, at least one $R^5$ is $(C_1$-$C_6)$-alkoxy, such as, methoxy, butoxy, or hexyloxy. In certain embodiments, at least one $R^5$ is $(C_1$-$C_4)$-alkoxy, such as, methoxy or butoxy. In some embodiments, at least one $R^5$ is substituted $(C_1$-$C_4)$-alkoxy, such as, methoxy substituted with an aryl or cycloalkyl.

In certain embodiments of compounds of Formula I, at least one $R^5$ is an aryl or heteroaryl that is optionally substituted with at least one methyl, methoxy, chloro, fluoro or trifluoromethyl.

In certain embodiments of compounds of Formula I, two $R^5$ taken together with the carbon atoms to which they are attached form a 5- or 6-membered aryl or substituted aryl. In some embodiments, the aryl is phenyl.

In certain embodiments of compounds of Formula I, at least one $R^5$ is at the C8 position. In other embodiments, at least one $R^5$ is at the C7 position. In other embodiments, at least one $R^5$ is at the C6 position. In other embodiments, at least one $R^5$ is at the C5 position.

In certain embodiments of compounds of Formula I,
q is 0;
$R^1$ is hydroxy;
$R^2$ and $R^4$ are hydrogen;
$R^3$ is selected from the group consisting of hydrogen, alkyl, and substituted alkyl; and
$R^{10}$ is $-OR^{13}$; wherein $R^{13}$ is hydrogen, or alkyl.

In some embodiments of compounds of Formula I,
$R^1$ is hydroxy;
$R^2$ and $R^4$ are hydrogen;
$R^3$ is selected from the group consisting of hydrogen, alkyl, and substituted alkyl; and
each $R^5$ is independently selected from the group consisting of halo, acylamino, alkyl, substituted alkyl, substituted alkynyl, cycloalkyl, aryl, substituted aryl, alkoxy, substituted alkoxy, heteroaryl, and substituted heteroaryl.

In some embodiments of compounds of Formula I,
$R^1$ is hydroxy;
$R^2$ and $R^4$ are hydrogen;
$R^3$ is selected from the group consisting of hydrogen, alkyl, and substituted alkyl; and
each $R^5$ is independently selected from the group consisting of hydrogen, halo, alkyl, substituted alkyl, aryl, substituted aryl, alkoxy, heteroaryl, and substituted heteroaryl.

In some embodiments of compounds of Formula I,
$R^1$ is hydroxy;
$R^2$ and $R^4$ are hydrogen;
$R^3$ is selected from the group consisting of hydrogen, alkyl, and substituted alkyl;
each $R^5$ is independently selected from the group consisting of halo, acylamino, alkyl, substituted alkyl, substituted alkynyl, cycloalkyl, aryl, substituted aryl, alkoxy, substituted alkoxy, heteroaryl, and substituted heteroaryl; and
$R^{10}$ is $-OR^{13}$; wherein $R^{13}$ is hydrogen, or alkyl.

In some embodiments of compounds of Formula I,
$R^1$ is hydroxy;
$R^2$ and $R^4$ are hydrogen;
$R^3$ is selected from the group consisting of hydrogen, alkyl, and substituted alkyl;
each $R^5$ is independently selected from the group consisting of hydrogen, halo, alkyl, substituted alkyl, aryl, substituted aryl, alkoxy, heteroaryl, and substituted heteroaryl; and
$R^{10}$ is $-OR^{13}$; wherein $R^{13}$ is hydrogen, or alkyl.

In other embodiments of compounds of Formula I,
q is 1 or 2;
$R^1$ is hydroxy;
$R^2$ and $R^4$ are hydrogen;
$R^3$ is selected from the group consisting of hydrogen, alkyl, and substituted alkyl;
each $R^5$ is independently selected from the group consisting of halo, acylamino, alkyl, substituted alkyl, substituted alkynyl, cycloalkyl, aryl, substituted aryl, alkoxy, substituted alkoxy, heteroaryl, and substituted heteroaryl; and
$R^{10}$ is $-OR^{13}$; wherein $R^{13}$ is hydrogen, or alkyl.

In other embodiments of compounds of Formula I,
q is 1 or 2;
$R^1$ is hydroxy;
$R^2$ and $R^4$ are hydrogen;
$R^3$ is selected from the group consisting of hydrogen, alkyl, and substituted alkyl;
each $R^5$ is independently selected from the group consisting of hydrogen, halo, alkyl, substituted alkyl, aryl, substituted aryl, alkoxy, heteroaryl, and substituted heteroaryl; and
$R^{10}$ is $-OR^{13}$; wherein $R^{13}$ is hydrogen, or alkyl.

In certain embodiments of compounds of Formula I,
q is 1 or 2;
$R^1$ is hydroxy;
$R^2$, $R^3$, and $R^4$ are hydrogen;
each $R^5$ is independently selected from the group consisting of halo, acylamino, alkyl, substituted alkyl, substituted alkynyl, cycloalkyl, aryl, substituted aryl, alkoxy, substituted alkoxy, heteroaryl, and substituted heteroaryl; and
$R^{10}$ is $-OR^{13}$; wherein $R^{13}$ is hydrogen.

In certain embodiments of compounds of Formula I,
q is 1 or 2;
$R^1$ is hydroxy;
$R^2$, $R^3$, and $R^4$ are hydrogen;

each $R^5$ is independently selected from the group consisting of hydrogen, halo, alkyl, substituted alkyl, aryl, substituted aryl, alkoxy, heteroaryl, and substituted heteroaryl; and $R^{10}$ is —$OR^{13}$; wherein $R^{13}$ is hydrogen.

In certain embodiments, the invention is directed to compounds of Formula II:

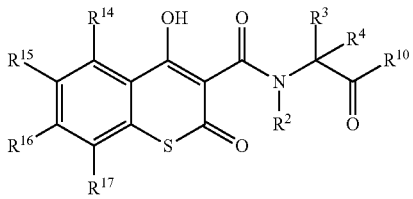

II wherein $R^2$ is selected from the group consisting of hydrogen, alkyl, and substituted alkyl;

$R^3$ is selected from the group consisting of hydrogen, deuterium, alkyl, and substituted alkyl;

$R^4$ is selected from the group consisting of hydrogen, deuterium, and methyl;

$R^{14}$, $R^{15}$ $R^{16}$ and $R^{17}$ are independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, cycloalkyl, substituted cycloalkyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heteroaryl, and substituted heteroaryl;

or $R^{14}$ and $R^{15}$, $R^{15}$ and $R^{16}$, or $R^{16}$ and $R^{17}$ are taken together with the carbon atoms to which they are attached to form a 5- or 6-membered aryl or substituted aryl;

$R^{16}$ is —$NR^{11}R^{12}$ or —$OR^{13}$;

$R^{11}$ and $R^{12}$ are independently selected from the group consisting hydrogen, alkyl, alkylene-cycloalkyl, heterocyclic, and aryl;

or $R^{11}$ and $R^{12}$ are taken together with the nitrogen to which they are attached form a 5- or 6-membered heterocyclic, substituted heterocyclic, heteroaryl or substituted heteroaryl; and $R^{13}$ is selected from the group consisting of a cation, hydrogen and alkyl which is unsubstituted or substituted with one or more substituents independently selected from the group consisting of cycloalkyl, heterocyclic, aryl, and heteroaryl;

or a pharmaceutically acceptable salt, single stereoisomer, mixture of stereoisomers, ester, or prodrug thereof.

In other embodiments, the invention is directed to compounds of Formula II:

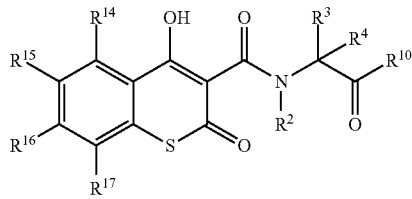

II wherein $R^2$ is selected from the group consisting of hydrogen, alkyl, and substituted alkyl;

$R^3$ is selected from the group consisting of hydrogen, deuterium, alkyl, and substituted alkyl;

$R^4$ is selected from the group consisting of hydrogen, deuterium, and methyl;

$R^{14}$, $R^{15}$ $R^{16}$ and $R^{17}$ are independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heteroaryl, and substituted heteroaryl;

or $R^{14}$ and $R^{15}$, $R^{15}$ and $R^{16}$, or $R^{16}$ and $R^{17}$ are taken together with the carbon atoms to which they are attached to form a 5- or 6-membered aryl or substituted aryl;

$R^{10}$ is —$NR^{11}R^{12}$ or —$OR^{13}$;

$R^{11}$ and $R^{12}$ are independently selected from the group consisting hydrogen, alkyl, alkylene-cycloalkyl, heterocyclic, and aryl;

or $R^{11}$ and $R^{12}$ are taken together with the nitrogen to which they are attached form a 5- or 6-membered heterocyclic, substituted heterocyclic, heteroaryl or substituted heteroaryl; and $R^{13}$ is selected from the group consisting of hydrogen and alkyl which is unsubstituted or substituted with one or more substituents independently selected from the group consisting of cycloalkyl, heterocyclic, aryl, and heteroaryl;

or a pharmaceutically acceptable salt, single stereoisomer, mixture of stereoisomers, ester, or prodrug thereof.

In certain embodiments, $R^{14}$ and $R^{17}$ are independently selected from the group consisting of hydrogen, halo, alkyl, substituted alkyl, substituted alkynyl, aryl, substituted aryl, heteroaryl, and substituted heteroaryl. In certain embodiments, $R^{14}$ and $R^{17}$ are independently selected from the group consisting of hydrogen, halo, alkyl, and alkoxy.

In certain embodiments, $R^{15}$ and $R^{16}$ are independently selected from the group consisting of hydrogen, halo, alkyl, substituted alkyl, acylamino, alkoxy, substituted alkoxy, aryl, substituted aryl, heteroaryl, and substituted heteroaryl. In certain embodiments, $R^{15}$ and $R^{16}$ are independently selected from the group consisting of hydrogen, halo, alkyl, substituted alkyl, alkoxy, aryl, substituted aryl, heteroaryl, and substituted heteroaryl.

In certain embodiments of compounds of Formula II, $R^2$ is hydrogen. In other embodiments, $R^4$ is hydrogen. In some embodiments, $R^2$ and $R^4$ are hydrogen.

In certain embodiments of compounds of Formula II, $R^3$ is selected from the group consisting of hydrogen and methyl. In particular embodiments, $R^2$, $R^3$, and $R^4$ are hydrogen.

In certain embodiments of compounds of Formula II, $R^{10}$ is —$OR^{13}$. In some embodiments $R^{13}$ is hydrogen, or alkyl which is unsubstituted or substituted with one or more substituents independently selected from the group consisting of cycloalkyl, heterocyclic, aryl, and heteroaryl. In some embodiments $R^{13}$ is $C_1$-$C_4$ alkyl. In particular embodiments, $R^{13}$ is hydrogen.

In some embodiments of compounds of Formula II,
$R^2$ and $R^4$ are hydrogen;
$R^3$ is selected from the group consisting of hydrogen, alkyl, and substituted alkyl; and
$R^{14}$, $R^{15}$, $R^{16}$ and $R^{17}$ are independently selected from the group consisting of hydrogen, halo, acylamino, alkyl, substituted alkyl, substituted alkynyl, cycloalkyl, aryl, substituted aryl, alkoxy, substituted alkoxy, heteroaryl, and substituted heteroaryl.

In some embodiments of compounds of Formula II,
$R^2$ and $R^4$ are hydrogen;
$R^3$ is selected from the group consisting of hydrogen, alkyl, and substituted alkyl; and
$R^{14}$, $R^{15}$, $R^{16}$ and $R^{17}$ are independently selected from the group consisting of hydrogen, halo, alkyl, substituted alkyl, aryl, substituted aryl, alkoxy, heteroaryl, and substituted heteroaryl.

In some embodiments of compounds of Formula II,
$R^2$ and $R^4$ are hydrogen;
$R^3$ is selected from the group consisting of hydrogen, alkyl, and substituted alkyl;
$R^{14}$, $R^{15}$, $R^{16}$ and $R^{17}$ are independently selected from the group consisting of hydrogen, halo, acylamino, alkyl, substituted alkyl, substituted alkynyl, cycloalkyl, aryl, substituted aryl, alkoxy, substituted alkoxy, heteroaryl, and substituted heteroaryl; and
$R^{16}$ is —$OR^{13}$; wherein $R^{13}$ is hydrogen or alkyl.

In some embodiments of compounds of Formula II,
$R^2$ and $R^4$ are hydrogen;
$R^3$ is selected from the group consisting of hydrogen, alkyl, and substituted alkyl;
$R^{14}$, $R^{15}$, $R^{16}$ and $R^{17}$ are independently selected from the group consisting of hydrogen, halo, alkyl, substituted alkyl, aryl, substituted aryl, alkoxy, heteroaryl, and substituted heteroaryl; and
$R^{16}$ is —$OR^{13}$; wherein $R^{13}$ is hydrogen or alkyl.

In other embodiments of compounds of Formula II,
$R^2$, $R^3$, and $R^4$ are hydrogen;
$R^{14}$ and $R^{17}$ are independently selected from the group consisting of hydrogen, halo, alkyl, substituted alkyl, substituted alkynyl, aryl, substituted aryl, heteroaryl, and substituted heteroaryl;
$R^{15}$ and $R^{16}$ are independently selected from the group consisting of hydrogen, halo, acylamino, alkyl, substituted alkyl, cycloalkyl, alkoxy, substituted alkoxy, aryl, substituted aryl, heteroaryl, and substituted heteroaryl; and
$R^{10}$ is —$OR^{13}$; wherein $R^{13}$ is hydrogen or alkyl.

In other embodiments of compounds of Formula II,
$R^2$, $R^3$, and $R^4$ are hydrogen;
$R^{14}$ and $R^{17}$ are independently selected from the group consisting of hydrogen, halo, alkyl, and alkoxy;
$R^{15}$ and $R^{16}$ are independently selected from the group consisting of hydrogen, halo, alkyl, substituted alkyl, alkoxy, aryl, substituted aryl, heteroaryl, and substituted heteroaryl; and
$R^{10}$ is —$OR^{13}$; wherein $R^{13}$ is hydrogen or alkyl.

In certain embodiments of compounds of Formula II,
$R^2$, $R^3$, and $R^4$ are hydrogen;
$R^{14}$ and $R^{15}$ taken together with the carbon atoms to which they are attached form a 5- or 6-membered aryl or substituted aryl;
$R^{16}$ is selected from the group consisting of hydrogen, halo, alkyl, substituted alkyl, alkoxy, aryl, substituted aryl, heteroaryl, and substituted heteroaryl;
$R^{17}$ is selected from the group consisting of hydrogen, halo, alkyl, and alkoxy; and
$R^{10}$ is —$OR^{13}$; wherein $R^{13}$ is hydrogen.

In certain embodiments of compounds of Formula II,
$R^2$, $R^3$, and $R^4$ are hydrogen;
$R^{14}$ is selected from the group consisting of hydrogen, halo, alkyl, and alkoxy;
$R^{15}$ is selected from the group consisting of hydrogen, halo, alkyl, substituted alkyl, alkoxy, aryl, substituted aryl, heteroaryl, and substituted heteroaryl;
$R^{16}$ and $R^{17}$ taken together with the carbon atoms to which they are attached form a 5- or 6-membered aryl or substituted aryl; and
$R^{10}$ is —$OR^{13}$; wherein $R^{13}$ is hydrogen.

Compounds of the invention include, but are not limited to, [(4-hydroxy-7-methoxy-2-oxo-2H-thiochromene-3-carbonyl)-amino]-acetic acid; [(4-hydroxy-6,7-dimethoxy-2-oxo-2H-thiochromene-3-carbonyl)-amino]-acetic acid; [(4-hydroxy-2-oxo-2H-thiochromene-3-carbonyl)-amino]-acetic acid; [(6-fluoro-4-hydroxy-2-oxo-2H-thiochromene-3-carbonyl)-amino]-acetic acid; [(7-bromo-4-hydroxy-2-oxo-2H-thiochromene-3-carbonyl)-amino]-acetic acid; [(4-hydroxy-7-methyl-2-oxo-2H-thiochromene-3-carbonyl)-amino]-acetic acid; {4-hydroxy-7-(4-methoxy-phenyl)-2-oxo-2H-thiochromene-3-carbonyl]-amino}-acetic acid; {[4-hydroxy-7-(3-methoxy-phenyl)-2-oxo-2H-thiochromene-3-carbonyl]-amino}-acetic acid; {4-hydroxy-7-(2-methoxy-phenyl)-2-oxo-2H-thiochromene-3-carbonyl]-amino}-acetic acid; {[7-(3,5-dichloro-phenyl)-4-hydroxy-2-oxo-2H-thiochromene-3-carbonyl]-amino}-acetic acid; {[4-hydroxy-2-oxo-7-(4-trifluoromethyl-phenyl)-2H-thiochromene-3-carbonyl]-amino}-acetic acid; [(4-hydroxy-2-oxo-7-phenyl-2H-thiochromene-3-carbonyl)-amino]-acetic acid; {[7-(4-fluoro-phenyl)-4-hydroxy-2-oxo-2H-thiochromene-3-carbonyl]-amino}-acetic acid; [(4-hydroxy-2-oxo-7-pyrimidin-5-yl-2H-thiochromene-3-carbonyl)-amino]-acetic acid; [(4-hydroxy-2-oxo-7-pyridin-3-yl-2H-thiochromene-3-carbonyl)-amino]-acetic acid, sodium salt; {[7-(5-fluoro-pyridin-3-yl)-4-hydroxy-2-oxo-2H-thiochromene-3-carbonyl]-amino}-acetic acid; {[7-(3-chloro-4-fluoro-phenyl)-4-hydroxy-2-oxo-2H-thiochromene-3-carbonyl]-amino}-acetic acid; [(4-hydroxy-7-naphthalen-2-yl-2-oxo-2H-thiochromene-3-carbonyl)-amino]-acetic acid; [(4-hydroxy-2-oxo-7-p-tolyl-2H-thiochromene-3-carbonyl)-amino]-acetic acid; [(7-benzyl-4-hydroxy-2-oxo-2H-thiochromene-3-carbonyl)-amino]-acetic acid; [(7-fluoro-4-hydroxy-2-oxo-2H-thiochromene-3-carbonyl)-amino]-acetic acid; [(6-chloro-4-hydroxy-8-methyl-2-oxo-2H-thiochromene-3-carbonyl)-amino]-acetic acid; [(4-hydroxy-8-methyl-2-oxo-2H-thiochromene-3-carbonyl)-amino]-acetic acid; [(1-hydroxy-3-oxo-3H-4-thia-phenanthrene-2-carbonyl)-amino]-acetic acid; [(1-hydroxy-3-oxo-3H-benzo[f]thiochromene-2-carbonyl)-amino]-acetic acid; [(7-butoxy-4-hydroxy-2-oxo-2H-thiochromene-3-carbonyl)- amino]-acetic acid; [(6-bromo-4-hydroxy-2-oxo-2H-thiochromene-3-carbonyl)-amino]-acetic acid; 2-(S)-[(6-bromo-4-hydroxy-2-oxo-2H-thiochromene-3-carbonyl)-amino]-propionic acid; {[7-(3,5-bis-trifluoromethyl-phenyl)-4-hydroxy-2-oxo-2H-thiochromene-3-carbonyl]-amino}-acetic acid; {[7-(3-fluoro-phenyl)-4-hydroxy-2-oxo-2H-thiochromene-3-carbonyl]-amino}-acetic acid; 2-(S)-{[7-(3-fluoro-phenyl)-4-hydroxy-2-oxo-2H-thiochromene-3-carbonyl]-amino}-propionic acid; {[4-hydroxy-2-oxo-7-(2-trifluoromethyl-phenyl)-2H-thiochromene-3-carbonyl]-amino}-acetic acid; {[6-(3,5-bis-trifluoromethyl-phenyl)-4-hydroxy-2-oxo-2H-thiochromene-3-carbonyl]-amino}-acetic acid; {[4-hydroxy-2-oxo-6-(2-trifluoromethyl-phenyl)-2H-thiochromene-3-carbonyl]-amino}-acetic acid; {[4-hydroxy-6-(4-methoxy-phenyl)-2-oxo-2H-thiochromene-3-carbonyl]-amino}-acetic acid; {[6-(2-chloro-phenyl)-4-hydroxy-2-oxo-2H-thiochromene-3-carbonyl]-amino}-acetic acid; {[6-(3-fluoro-phenyl)-4-hydroxy-2-oxo-2H-thiochromene-3-carbonyl]-amino}-acetic acid; {[6-(4-fluoro-phenyl)-4-hydroxy-2-oxo-2H-thiochromene-3-carbonyl]-amino}-acetic acid; {[4-hydroxy-6-(2-methoxy-phenyl)-2-oxo-2H-thiochromene-3-carbonyl]-amino}-acetic acid; {[4-hydroxy-2-oxo-6-(4-trifluoromethoxy-phenyl)-2H-thiochromene-3-carbonyl]-amino}-acetic acid; [(6-benzoylamino-4-hydroxy-2-oxo-2H-thiochromene-3-carbonyl)-amino]-acetic acid; [(8-benzyl-6-chloro-4-hydroxy-2-oxo-2H-thiochromene-3-carbonyl)-amino]-acetic acid; {[8-(3,5-bis-trifluoromethyl-phenyl)-6-chloro-4-hydroxy-2-oxo-2H-thiochromene-3-carbonyl]-amino}-acetic acid; [(6-chloro-4-hydroxy-2-oxo-8-phenyl-2H-thiochromene-3-carbonyl)-amino]-acetic acid; {[6-chloro-4-hydroxy-8-(2-methyl-5-trifluoromethyl-2H-pyrazol-3-yl)-2-oxo-2H-thiochromene-3-carbonyl]-amino}-acetic acid; [(6-chloro-4-hydroxy-2-oxo-8-pyridin-3-yl-2H-thiochromene-3-carbonyl)-amino]-acetic acid; [(8-benzyl-4-hydroxy-2-oxo-2H-thiochromene-3-carbonyl)-amino]-acetic acid; {[8-(3,5-bis-trifluoromethyl-phenyl)-4-hydroxy-2-oxo-2H-thiochromene-3-carbonyl]-amino}-acetic acid; {[4-hydroxy-8-(2-methyl-5-trifluoromethyl-2H-pyrazol-3-yl)-2-oxo-2H-thiochromene-3-carbonyl]-amino}-acetic acid; [(4-hydroxy-2-oxo-8-pyridin-3-yl-2H-thiochromene-3-carbonyl)-amino]-acetic acid; [(4-hydroxy-2-oxo-8-phenyl-2H-thiochromene-3-carbonyl)-amino]-acetic acid; [(5-fluoro-4-hydroxy-2-oxo-2H-thiochromene-3-carbonyl)-amino]-acetic acid; [(7-cyclopropyl-4-hydroxy-2-oxo-2H-thiochromene-3-carbonyl)-amino]-acetic acid; {[4-hydroxy-7-(2-methyl-5-trifluoromethyl-2H-pyrazol-3-yl)-2-oxo-2H-thiochromene-3-carbonyl]-amino}-acetic acid; 2-(S)-{[4-hydroxy-7-(2-methyl-5-trifluoromethyl-2H-pyrazol-3-yl)-2-oxo-2H-thiochromene-3-carbonyl]-amino}-propionic acid; [(6-chloro-4-hydroxy-2-oxo-8-phenylethynyl-2H-thiochromene-3-carbonyl)-amino]-acetic acid; 2-(S)-[(4-hydroxy-2-oxo-2H-thiochromene-3-carbonyl)-amino]-propionic acid; [(6-chloro-4-hydroxy-2-oxo-2H-thiochromene-3-carbonyl)-amino]-acetic acid; 2-(S)-[(6-chloro-4-hydroxy-2-oxo-2H-thiochromene-3-carbonyl)-amino]-propionic acid; [(7-chloro-4-hydroxy-2-oxo-2H-thiochromene-3-carbonyl)-amino]-acetic acid; 2-(S)-[(7-chloro-4-hydroxy-2-oxo-2H-thiochromene-3-carbonyl)-amino]-propionic acid; [(6-benzyloxy-4-hydroxy-2-oxo-2H-thiochromene-3-carbonyl)-amino]-acetic acid; [(6-cyclohexylmethoxy-4-hydroxy-2-oxo-2H-thiochromene-3-carbonyl)-amino]-acetic acid; and [(6-hexyloxy-4-hydroxy-2-oxo-2H-thiochromene-3-carbonyl)-amino]-acetic acid; or a pharmaceutically acceptable salt, single stereoisomer, mixture of stereoisomers, ester, tautomer, or prodrug thereof

2. Compositions and Methods of the Invention

The invention provides for use of a compound of Formula I or II for the manufacture of a medicament for use in treating various conditions or disorders as described herein. In one embodiment, a pharmaceutical composition is provided comprising at least one compound of Formula I or II and a pharmaceutically acceptable excipient or carrier.

In various embodiments, the medicament or pharmaceutical composition can further comprise or be used in combination with at least one additional therapeutic agent. In one embodiment, the agent is selected from the group consisting of vitamin $B_{12}$, ferrous sulfate, folic acid, and/or recombinant erythropoietin or an erythropoiesis stimulating agent (ESA).

The compounds of the present invention, or medicaments or compositions comprising the compounds, can be used to inhibit HIF hydroxylase activity, thereby modulating the stability and/or activity of HIF and activating HIF-regulated gene expression. The compound, or composition or medicament thereof, can be used in methods to treat, pretreat, or delay progression or onset of conditions mediated at least in part by HIF, including, but not limited to, anemia and various aspects of ischemic and hypoxic conditions. Ischemic and hypoxic conditions may result from an event selected from, but not limited to, myocardial infarction, pulmonary embolism, intestinal infarction, ischemic stroke, acute respiratory failure, renal ischemic-reperfusion injury, cardiac cirrhosis, macular degeneration, neonatal respiratory distress syndrome, peripheral artery disease, chronic kidney failure, congestive heart failure, etc. In yet another embodiment, the compound, or composition or medicament thereof, is administered immediately after a trauma or injury. In other embodiments, the compound, or composition or medicament thereof, can be administered to a subject based on predisposing conditions, e.g., hypertension, diabetes, occlusive arterial disease, chronic venous insufficiency, Raynaud's disease, chronic skin ulcers, cirrhosis, congestive heart failure, transient ischemic attack, and systemic sclerosis. In still other embodiments, compounds may be administered to a subject to decrease or prevent the development of tissue damage associated with ischemia or hypoxia.

The compounds of the present invention, or compositions or medicaments thereof, can also be used to increase endogenous erythropoietin (EPO). The compounds, or composition or medicament thereof, can be administered to prevent, pretreat, or treat EPO-associated conditions, including, e.g., conditions associated with anemia and neurological disorders. In one embodiment, the compounds of the present invention, or compositions or medicaments thereof, can be used to treat, pretreat, or delay onset of anemia such as anemia that may develop in association with various conditions or disorders. Conditions associated with anemia include, but are not limited to, acute or chronic kidney disease, diabetes, cancer, ulcers, infection with virus, e.g., HIV, bacteria, or parasites; inflammation, etc. Conditions can further include those associated with procedures or treatments including, e.g., radiation therapy, chemotherapy, dialysis, anesthesia, and surgery. Conditions associated with anemia additionally include abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatincontaining chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

The invention is also directed to a method of inhibiting the activity of at least one hydroxylase enzyme which modifies the alpha subunit of hypoxia inducible factor. The HIF hydroxylase enzyme may be an asparaginyl hydroxylase such as Factor Inhibiting HIF (FIH). The HIF hydroxylase enzyme may be a prolyl hydroxylase including, but not limited to, a prolyl hydroxylase selected from the group consisting of EGLN1, EGLN2, and EGLN3. In one embodiment, the method comprises contacting the hydroxylase enzyme with an effective amount of one or more compounds selected from the group comprising compounds of Formula I or II.

3. Definitions

It must be noted that as used herein, and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology, and pharmacology, within the skill of the art. Such techniques are explained fully in the literature. (See, e.g., Gennaro, A. R., ed. (1990) Remington's Pharmaceutical Sciences, 18$^{th}$ ed., Mack Publishing Co.; Colowick, S. et al., eds., Methods In Enzymology, Academic Press, Inc.; D. M. Weir, and C. C. Blackwell, eds. (1986) Handbook of Experimental Immunology, Vols. I-IV, Blackwell Scientific Publications; Maniatis, T. et al., eds. (1989) Molecular Cloning: A Laboratory Manual, 2$^{nd}$ edition, Vols. I-III, Cold Spring Harbor Laboratory Press; Ausubel, F. M. et al., eds. (1999) Short Protocols in Molecular Biology, 4$^{th}$ edition, John Wiley & Sons; Ream et al., eds. (1998) Molecular Biology Techniques: An Intensive Laboratory Course, Academic Press; Newton & Graham eds. (1997) PCR (Introduction to Biotechniques Series), 2nd ed., Springer Verlag).

The term "HIFα" refers to the alpha subunit of hypoxia inducible factor protein. HIFα may be any human or other mammalian protein, or fragment thereof, including, but not limited to, human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130, and AAB41496), and HIF-3α (Genbank Accession No. AAC72734); rat HIF-1a (Genbank Accession No. CAA70701), HIF-2α (Genbank Accession No. CAB96612), and HIF-3α (Genbank Accession No. CAB96611); and bovine HIF-1α (Genbank Accession No. BAA78675), HIF-2α (GenBank Accession No. BAA78676), and HIF-3α (Genbank Accession No. NP_001098812). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1a (Genbank Accession No. BAA34234).

A fragment of HIFα includes any fragment retaining at least one functional or structural characteristic of HIFa. Fragments of HIFα include, e.g., the regions defined by human HIF-1α from amino acids 401 to 603 (Huang et al., supra), amino acid 531 to 575 (Jiang et al. 1997) *J. Biol. Chem.* 272:19253-19260), amino acid 556 to 575 (Tanimoto et al., supra), amino acid 557 to 571 (Srinivas et al. (1999) *Biochem. Biophys. Res. Commun.* 260:557-561), and amino acid 556 to 575 (Ivan and Kaelin (2001) *Science* 292:464-468). Further, HIFα fragments include any fragment containing at least one occurrence of the motif LXXLAP (SEQ ID NO:1), e.g., such as occurs in the human HIF-1α native sequence from $L_{397}$ to $P_{402}$, and from $L_{559}$ to $P_{564}$.

The terms "HIF-associated conditions" and "conditions mediated at least in part by HIF" are used inclusively and refer to any condition that can be associated with below normal, abnormal, or inappropriate modulation of HIF. HIF-associated conditions include any condition wherein an increase in HIF level would provide therapeutic benefit. HIF-associated conditions include anemic conditions and tissue damage or disorders associated with ischemic or hypoxic conditions.

The term "HIF hydroxylase" refers to any enzyme that modifies the alpha subunit of HIF by hydroxylation of one or more amino acid residues. HIF hydroxylases include Factor Inhibiting HIF (F1H) (GenBank Accession AAL27308; Mahon et al. (2001) *Genes Dev.* 15:2675-2686; Lando et al. (2002) *Science* 295:858-861; and Lando et al. (2002) *Genes Dev.* 16:1466-1471), which modifies at least one asparagine residue found within HIFa. (Also, see, Elkins et al. (2002) *J. Biol. Chem.*C200644200.) HIF hydroxylases also include HIF prolyl hydroxylases (HIF PHs), which modify proline residues found within HIFa.

The terms "HIF prolyl hydroxylase" and "HIF PH" refer to any enzyme that modifies the alpha subunit of HIF protein by hydroxylation of one or more proline residues. Preferably, the proline residue hydroxylated by HIF PH includes the proline found within the motif LXXLAP (SEQ ID NO:1). HIF PH includes members of the Egl-Nine (EGLN) gene family described by Taylor (2001, *Gene* 275:125-132), and characterized by Aravind and Koonin (2001, Genome Biol 2: RESEARCH 0007), Epstein et al. (2001, Cell 107:43-54), and Bruick and McKnight (2001, *Science* 294:1337-1340). HIF PH2, as used in examplary assays described herein (infra), may be any HIF PH2, e.g., human EGLN1 (GenBank Accession No. AAG33965; Dupuy et al. (2000) *Genomics* 69:348-54), mouse EGLN1 (GenBank Accession No. CAC42515), rat EGLN1 (GenBank Accession No. P59722), etc. Alternatively, another HIF PH may be used in the assay. Such HIF PH enzymes include, but are not limited to, human EGLN2 isoform 1 (GenBank Accession No. CAC42510; Taylor, supra), human EGLN2 isoform 3 (GenBank Accession No. NP 542770), mouse EGLN2 (GenBank Accession No. CAC42516), and rat EGLN2 (GenBank Accession No. AAO46039); and human EGLN3 (GenBank Accession No. CAC42511; Taylor, supra), mouse EGLN3 (GenBank Accession No. CAC42517), and rat EGLN3 (SM-20) (GenBank Accession No. AAA19321). In other embodiments of the present invention, EGLN may include *Caenorhabditis elegans* EGL-9 (GenBank Accession No. AAD56365) and *Drosophila melanogaster* CG1114 gene product (GenBank Accession No. AAF52050). HIF PH also includes any fragment of the foregoing full-length proteins that retains the ability to hydroxylate at least one prolyl residue in HIFα.

The term "ischemia" refers to a deficient supply of blood to a cell, tissue, organ, etc. Ischemia is associated with a reduction in nutrients, including oxygen, delivered to tissues. Ischemia may arise due to conditions such as atherosclerosis, formation of a thrombus in an artery or vein, blockage of an artery or vein by an embolus, vascular closure due to other causes, e.g., vascular spasm, etc. Such conditions may reduce blood flow, producing a state of hypoperfusion to an organ or tissue, or block blood flow completely. Other conditions that can lead to ischemia include tissue damage due to trauma or injury, such as, e.g., spinal cord injury; viral infection, which can lead to, e.g., congestive heart failure, etc. The term "ischemic condition" refers to conditions or events that are associated with or result in ischemia. Conditions associated or resulting in ischemia include, but are not limited to, an event selected from the group consisting of myocardial infarction, ischemic stroke, pulmonary embolism, perinatal hypoxia, circulatory shock including, e.g., hemorrhagic, septic, cardiogenic, etc.; mountain sickness, acute respiratory failure, etc.; intestinal infarction, acute kidney failure, renal ischemia reperfusion injury, etc.; atherosclerosis, chronic venous insufficiency, congestive heart failure, cardiac cirrhosis, diabetes, macular degeneration, sleep apnea, Raynaud's disease, systemic sclerosis, nonbacterial thrombotic endocarditis, occlusive artery disease, angina pectoris, transient ischemic attacks (TIAs), chronic alcoholic liver disease, chronic kidney failure, peripheral vascular disorders, ulcers, burns, chronic wounds etc. Ischemia can also result when individuals are placed under general anesthesia, and can cause tissue damage in organs prepared for transplant.

The terms "hypoxia" and "hypoxic" refer to an environment with levels of oxygen below normal. The term "hypoxic condition" includes, but is not limited to, ischemic conditions (ischemic hypoxia) such as those listed above, wherein hypoxia results from reduced circulation; pulmonary disorders (hypoxic hypoxia) such as COPD, severe pneumonia, pulmonary edema, pulmonary hypertension, hyaline membrane disease, and the like, wherein hypoxia results from reduced oxygenation of the blood in the lungs; anemic conditions (anemic hypoxia) such as gastric or duodenal ulcers, liver or renal disease, thrombocytopenia or blood coagulation disorders, cancer or other chronic illness, cancer chemotherapy and other therapeutic interventions that produce anemia, and the like, wherein hypoxia results from a decreased concentration of hemoglobin or red blood cells; and altitude sickness, etc.

The term "anemia" as used herein refers to any abnormality or deficiency in hemoglobin or erythrocytes that leads to reduced oxygen levels in the blood. Anemia can be associated with abnormal production, processing, or performance of erythrocytes and/or hemoglobin. The term anemia refers to any reduction in the number of red blood cells and/or in the level of hemoglobin in blood relative to normal blood levels.

The term "anemic condition" refers to any condition, disease, or disorder associated with anemia. Anemia can arise due to various conditions, for example, acute or chronic kidney disease, infections, inflammation, cancer, irradiation, toxins, diabetes, and surgery. Infections may be due to, e.g., virus, bacteria, and/or parasites, etc. Inflammation may be due to infection or autoimmune disorders, such as rheumatoid arthritis, etc. Anemia can be associated with blood loss due to, e.g., stomach ulcers, duodenal ulcers, hemorrhoids, cancer of the stomach or large intestine, trauma, injury, surgical procedures, etc. Anemia can develop in association with radiation therapy, chemotherapy, and kidney dialysis. Anemia can also develop in HIV-infected patients undergoing treatment with azidothymidine (zidovudine) or other reverse transcriptase inhibitors, and can develop in cancer patients undergoing chemotherapy, e.g., with cyclic cisplatin- or non-cisplatin-containing chemotherapeutics. Aplastic anemia and myelodysplastic syndromes are diseases associated with bone marrow failure, which results in decreased production of erythrocytes. Further, anemia can result from defective or abnormal hemoglobin or erythrocytes, such as in disorders including microcytic anemia, hypochromic anemia, etc. Anemia can result from disorders in iron transport, processing, and utilization, see, e.g., sideroblastic anemia, etc.

The terms "disorders," "diseases," and "conditions" are used inclusively herein and refer to any condition deviating from normal.

The terms "erythropoietin" and "EPO" refer to any naturally occurring, recombinant, or synthetic erythropoietin, erythropoiesis stimulating protein (ESP), or erythropoiesis stimulating agent (ESA) including, e.g., human erythropoietin (GenBank Accession No. AAA52400; Lin et al. (1985) Proc. Nat'l. Acad. Sci. USA 82:7580-7584), EPOETIN human recombinant erythropoietin (Amgen, Inc., Thousand Oaks Calif.), ARANESP human recombinant erythropoietin (Amgen), PROCRIT human recombinant erythropoietin (Ortho Biotech Products, L. P., Raritan N.J.), Continuous erythropoiesis receptor activator (CERA; F. Hoffmann-La Roche Ltd., Basel, Switzerland), etc.

The terms "erythropoietin-associated conditions" and "conditions mediated at least in part by erythropoietin" are used inclusively and refer to any condition that can be associated with below normal, abnormal, or inappropriate modulation of erythropoietin. EPO-associated conditions include any condition wherein an increase in EPO level would provide therapeutic benefit. Erythropoietin-associated conditions include anemic conditions such as those described above.

EPO-associated conditions further include neurological disorders and/or injuries, including cases of stroke, trauma, epilepsy, neurodegenerative disease, and the like, wherein erythropoietin may provide a neuroprotective effect. Neurodegenerative diseases contemplated by the invention include Alzheimer's disease, Parkinson's disease, Huntington's disease, and the like.

The terms "treating," "treatment" and the like, are used herein to mean administering a therapy to a patient in need thereof. The therapy may be administered thereby providing a prophylactic effect in terms of completely or partially preventing a disorder or sign or symptom thereof and/or the therapy may be administered thereby providing a partial or complete cure for a disorder and/or adverse effect attributable to the disorder.

The term "alkyl" refers to saturated monovalent hydrocarbyl groups having from 1 to 10 carbon atoms, more particularly from 1 to 5 carbon atoms, and even more particularly 1 to 3 carbon atoms. This term is exemplified by groups such as methyl, ethyl, n-propyl, iso-propyl, n-butyl, t-butyl, n-pentyl, and the like.

The term "substituted alkyl" refers to an alkyl group of from 1 to 10 carbon atoms, more particularly 1 to 5 carbon atoms, and having from 1 to 5 substituents, preferably 1 to 3 substituents, each of which substituents is independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thio, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, sulfonyl, substituted sulfonyl, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{40}$R$^{40}$, —NR$^{40}$S(O)$_2$—NR$^{40}$-alkyl, —NR$^{40}$S(O)$_2$—NR$^{40}$-substituted alkyl, —NR$^{40}$S(O)$_2$—NR$^{40}$-aryl, —NR$^{40}$S(O)$_2$—NR$^{40}$-substituted aryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heterocyclic, and —NR$^{40}$S(O)$_2$—NR$^{40}$-substituted heterocyclic, where each R$^{40}$ is independently selected from hydrogen or alkyl. This group is exemplified by groups such as trifluoromethyl, benzyl, pyrazol-1-ylmethyl, etc.

The term "alkylidene" or "alkylene" refers to divalent saturated aliphatic hydrocarbyl groups preferably having from 1 to 5 and more preferably 1 to 3 carbon atoms which are either straight-chained or branched. This term is exemplified by groups such as methylene (—CH$_2$—), ethylene (—CH$_2$CH$_2$—) n-propylene (—CH$_2$CH$_2$CH$_2$—), iso-propylene (—CH$_2$CH(CH$_3$)—) and the like. "(C$_{u-v}$)alkylene" refers to alkylene groups having from u to v carbon atoms. The alkylidene or alkylene groups include branched and straight chain hydrocarbyl groups. For example "(C$_{1-6}$)alkylene" is meant to include methylene, ethylene, propylene, 2-methypropylene, pentylene, and the like.

The term "alkyl alcohol" refers to the group "alkyl-OH". For example, alkyl alcohol is meant to include methanol, ethanol, 2-propanol, 2-butanol, butanol, etc.

The term "substituted alkyl alcohol" refers to the group "substituted alkyl-OH".

The term "alkoxy" refers to the group "alkyl-O—," which includes, by way of example, methoxy, ethoxy, n-propoxy, iso-propoxy, n-butoxy, t-butoxy, sec-butoxy, n-pentoxy, and the like.

The term "substituted alkoxy" refers to the group "substituted alkyl-O—".

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—, provided that a nitrogen atom of the heterocyclic or substituted heterocyclic is not bound to the —C(O)— group, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminoacyl" or "amide", or the prefix "carbamoyl," "carboxamide," "substituted carbamoyl" or "substituted carboxamide" refers to the group —C(O)NR$^{42}$R$^{42}$ where each R$^{42}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic; or where each R$^{42}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "alkenyl" refers to a vinyl unsaturated monovalent hydrocarbyl group having from 2 to 6 carbon atoms, and preferably 2 to 4 carbon atoms, and having at least 1, and preferably from 1 to 2 sites of vinyl (>C=C<) unsaturation. Such groups are exemplified by vinyl (ethen-1-yl), allyl, but-3-enyl and the like.

The term "substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This term includes both E (trans) and Z (cis) isomers as appropriate. It also includes mixtures of both E and Z components.

The term "alkynyl" refers to acetylenic unsaturated monovalent hydrocarbyl groups having from 2 to 6 carbon atoms, and preferably 2 to 3 carbon atoms, and having at least 1, and preferably from 1 to 2 sites of acetylenic (—C≡C—) unsaturation. This group is exemplified by ethyn-1-yl, propyn-1-yl, propyn-2-yl, and the like.

The term "substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This group is exemplified by groups such as phenylethynyl, etc.

The term "amino" refers to the group —NH$_2$.

The term "substituted amino" refers to the group —NR$^{41}$R$^{41}$, where each R$^{41}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, sulfonyl, and substituted sulfonyl, provided that both R$^{41}$ groups are not hydrogen; or the R$^{41}$ groups can be joined together with the nitrogen atom to form a heterocyclic or substituted heterocyclic ring. This group is exemplified by phenylamino, methylphenylamino, and the like. This group is exemplified by groups such as (ethanic acid-2-yl)amino, etc.

The term "acylamino" refers to the groups —NR$^{45}$C(O) alkyl, —NR$^{45}$C(O)substituted alkyl, —NR$^{45}$C(O)cycloalkyl, —NR$^{45}$C(O)substituted cycloalkyl, —NR$^{45}$C(O) alkenyl, —NR$^{45}$C(O)substituted alkenyl, —NR$^{45}$C(O)

alkynyl, —NR$^{45}$C(O)substituted alkynyl, —NR$^{45}$C(O)aryl, —NR$^{45}$C(O)substituted aryl, —NR$^{45}$C(O)heteroaryl, —NR$^{45}$C(O)substituted heteroaryl, —NR$^{45}$C(O)heterocyclic, and —NR$^{45}$C(O)substituted heterocyclic where R$^{45}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are defined herein.

The term "oxycarbonylamino" refers to the groups —NR$^{46}$C(O)O-alkyl, —NR$^{46}$C(O)O-substituted alkyl, —NR$^{46}$C(O)O-alkenyl, —NR$^{46}$C(O)O-substituted alkenyl, —NR$^{46}$C(O)O-alkynyl, —NR$^{46}$C(O)O-substituted alkynyl, —NR$^{46}$C(O)O-cycloalkyl, —NR$^{46}$C(O)O-substituted cycloalkyl, —NR$^{46}$C(O)O-aryl, —NR$^{46}$C(O)O-substituted aryl, —NR$^{46}$C(O)O-heteroaryl, —NR$^{46}$C(O)O-substituted heteroaryl, —NR$^{46}$C(O)O-heterocyclic, and —NR$^{46}$C(O)O-substituted heterocyclic where R$^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "oxythiocarbonylamino" refers to the groups —NR$^{46}$C(S)O-alkyl, —NR$^{46}$C(S)O-substituted alkyl, —NR$^{46}$C(S)O-alkenyl, —NR$^{46}$C(S)O-substituted alkenyl, —NR$^{46}$C(S)O-alkynyl, —NR$^{46}$C(S)O-substituted alkynyl, —NR$^{46}$C(S)O-cycloalkyl, —NR$^{46}$C(S)O-substituted cycloalkyl, —NR$^{46}$C(S)O-aryl, —NR$^{46}$C(S)O-substituted aryl, —NR$^{46}$C(S)O-heteroaryl, —NR$^{46}$C(S)O-substituted heteroaryl, —NR$^{46}$C(S)O-heterocyclic, and —NR$^{46}$C(S)O-substituted heterocyclic where R$^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonyloxy," or the prefix "carbamoyloxy" or "substituted carbamoyloxy," refers to the groups —OC(O)NR$^{47}$R$^{47}$ where each R$^{47}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic; or where each R$^{47}$ is joined to form, together with the nitrogen atom, a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonylamino" refers to the group —NR$^{49}$C(O)N(R$^{49}$)$_2$ where each R$^{49}$ is independently selected from the group consisting of hydrogen and alkyl.

The term "aminothiocarbonylamino" refers to the group —NR$^{49}$C(S)N(R$^{49}$)$_2$ where each R$^{49}$ is independently selected from the group consisting of hydrogen and alkyl.

The term "aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is the aryl group. Preferred aryls include phenyl and naphthyl.

The term "substituted aryl" refers to aryl groups, as defined herein, which are substituted with from 1 to 4, particularly 1 to 3, substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amidino (—C(═NH)-amino or substituted amino), amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters, cyano, thio, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino (—NH—C(═NH)-amino or substituted amino), halo, nitro, heteroaryl, substituted heteroaryl, heterocyclic, substituted heterocyclic, oxycarbonylamino, oxythiocarbonylamino, sulfonyl, substituted sulfonyl, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{51}$R$^{51}$, —NR$^{51}$S(O)$_2$—NR$^{51}$-alkyl, —NR$^{51}$S(O)$_2$—NR$^{51}$-substituted alkyl, —NR$^{51}$S(O)$_2$—NR$^{51}$-aryl, —NR$^{51}$S(O)$_2$—NR$^{51}$-substituted aryl, —NR$^{51}$S(O)$_2$—NR$^{51}$-heteroaryl, —NR$^{51}$S(O)$_2$—NR$^{51}$-substituted heteroaryl, —NR$^{51}$S(O)$_2$—NR$^{51}$-heterocyclic, —NR$^{51}$S(O)$_2$—NR$^{51}$-substituted heterocyclic, where each R$^{51}$ is independently selected from hydrogen or alkyl, wherein each of the terms is as defined herein. This group is exemplified by groups such as 4-fluorophenyl, 3-methoxyphenyl, 4-t-butylphenyl, 4-trifluoromethylphenyl, 2-trifluoromethoxyphenyl, 3-trifluoromethoxyphenyl, 4-trifluoromethoxyphenyl, 2-chlorophenyl, 3-chlorophenyl, 4-chlorophenyl, 2-chloro-6-fluorophenyl, 2,4-dichlorophenyl, 4-methoxyphenyl, 3-cyanophenyl, 4-cyanophenyl, 4-phenoxyphenyl, 4-methanesulfonylphenyl, biphenyl-4-yl, etc.

The term "aryloxy" refers to the group aryl-O— that includes, by way of example, phenoxy, naphthoxy, and the like.

The term "substituted aryloxy" refers to substituted aryl-O— groups.

The term "aryloxyaryl" refers to the group -aryl-O-aryl.

The term "substituted aryloxyaryl" refers to aryloxyaryl groups substituted with from 1 to 3 substituents on either or both aryl rings as defined above for substituted aryl.

The term "carboxyl" refers to —COOH or salts thereof.

The term "carboxyl ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)β-cycloalkyl, —C(O)O-substituted cycloalkyl, —C(O)O-aryl, —C(O)O-substituted aryl, —C(O)O-heteroaryl, —C(O)O-substituted heteroaryl, —C(O)O-heterocyclic, and —C(O)O-substituted heterocyclic.

The term "cyano" refers to the group —CN.

The term "cycloalkyl" refers to a saturated or an unsaturated but nonaromatic cyclic alkyl groups of from 3 to 10, 3 to 8 or 3 to 6 carbon atoms having single or multiple cyclic rings including, by way of example, adamantyl, cyclopropyl, cyclobutyl, cyclopentyl, cyclooctyl, cyclohexenyl, and the like.

The term "substituted cycloalkyl" refers to a cycloalkyl group, having from 1 to 5 substituents selected from the group consisting of oxo (═O), thioxo (═S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl esters, cycloalkyl, substituted cycloalkyl, heteroaryl, substituted heteroaryl, heterocyclic, and substituted heterocyclic.

The term "cycloalkylene" and "substituted cycloalkylene" refer to divalent cycloalkyl and substituted cycloalkyl groups as defined above.

The term "cycloalkoxy" refers to —O-cycloalkyl groups.

The term "substituted cycloalkoxy" refers to —O-substituted cycloalkyl groups.

The term "halo" or "halogen" refers to fluoro, chloro, bromo, and iodo.

The term "hydroxy" or "hydroxyl" refers to the group —OH.

The term "heteroaryl" refers to an aromatic ring of from 1 to 15 carbon atoms, preferably from 1 to 10 carbon atoms, and 1 to 4 heteroatoms within the ring selected from the group consisting of oxygen, nitrogen, and sulfur. Such heteroaryl groups can have a single ring (e.g., pyridinyl, furyl, or thienyl) or multiple condensed rings (e.g., indolizinyl or benzothienyl) provided the point of attachment is through a ring containing the heteroatom and that ring is aromatic. The nitrogen and/or sulfur ring atoms can optionally be oxidized to provide for the N-oxide or the sulfoxide, and sulfone derivatives. Examples of heteroaryls include but are not limited to, pyridinyl, pyrimidinyl, pyrrolyl, pyrazolyl, indolyl, thiophenyl, thienyl, and furyl.

The term "substituted heteroaryl" refers to heteroaryl groups that are substituted with from 1 to 3 substituents selected from the same group of substituents defined for substituted aryl. This group is exemplified by groups such as 5-fluoro-pyridin-3-yl, 1-benzyl-1H-[1,2,3]triazol-4-yl, 5-bromo-furan-2-yl, trifluoromethyl-2H-pyrazol-3-yl, etc.

The term "heteroaryloxy" refers to the group —O-heteroaryl, and "substituted heteroaryloxy" refers to the group —O-substituted heteroaryl.

The term "heterocyclyl" or "heterocyclic" refers to a saturated or unsaturated (but not aromatic) group having a single ring or multiple condensed rings, from 1 to 10 carbon atoms, and from 1 to 4 hetero atoms selected from the group consisting of nitrogen, sulfur or oxygen within the ring wherein, in fused ring systems, one or more of the rings can be aryl or heteroaryl provided that the point of attachment is at the heterocycle. The nitrogen and/or sulfur ring atoms can optionally be oxidized to provide for the N-oxide or the sulfoxide, and sulfone derivatives.

The term "substituted heterocyclyl" or "substituted heterocyclic" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

The term "nitro" refers to the group —NO$_2$.

The term "oxo" refers to the atom (=O) or to the atom (—O$^-$).

The term "sulfonyl" refers to the group —S(O)$_2$H. The term "substituted sulfonyl" refers to the group —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

The term "heterocyclyloxy" refers to the group —O-heterocyclic, and "substituted heterocyclyloxy" refers to the group —O-substituted heterocyclic.

The term "thio" or "mercapto" refers to the group —SH.

The term "alkylsulfanyl," "alkylthio," or "thioether" refers to the groups —S-alkyl where alkyl is as defined above.

The term "substituted alkylthio," "substituted alkylsulfanyl," or "substituted alkylthio" refers to the group —S-substituted alkyl where substituted alkyl is as defined above.

The term "cycloalkylthio" or "cycloalkylsulfanyl" refers to the groups —S -cycloalkyl where cycloalkyl is as defined above.

The term "substituted cycloalkylthio" refers to the group —S-substituted cycloalkyl where substituted cycloalkyl is as defined above.

The term "arylthio" or "arylsulfanyl" refers to the group —S-aryl, and "substituted arylthio" refers to the group —S-substituted aryl where aryl and substituted aryl are as defined above.

The term "heteroarylthio" or "heteroarylsulfanyl" refers to the group —S-heteroaryl, and "substituted heteroarylthio" refers to the group —S-substituted heteroaryl where heteroaryl and substituted heteroaryl are as defined above.

The term "heterocyclicthio" or "heterocyclicsulfanyl" refers to the group —S-heterocyclic, and "substituted heterocyclicthio" refers to the group —S-substituted heterocyclic where heterocyclic, and substituted heterocyclic are as defined above.

The term "ester" refers to compounds of Formula I or II that include the group —COOR$^{54}$ where R$^{54}$ is alkyl, substituted alkyl, alkoxy, or substituted alkoxy. For example, esters of the invention include compounds of Formula I wherein R$^{10}$ is —OR$^{13}$ and R$^{13}$ is alkyl. In some embodiments, esters include compounds of Formula I wherein R$^1$ is acyloxy. Esters of Formula II can be provided, for example, via esterification of the hydroxyl group at the C4 position of the thiocoumarin ring using a suitable reagent such as an acid chloride or anhydride and/or esterification of the carboxylic acid moiety. Such methods are well known in the art.

The term "pharmaceutically acceptable salt" refers to pharmaceutically acceptable salts of a compound, which salts are derived from a variety of organic and inorganic counter ions well known in the art, and include, by way of example only, sodium, potassium, calcium, magnesium, ammonium, tetraalkylammonium, and the like; and, when the molecule contains a basic functionality, salts of organic or inorganic acids, such as hydrochloride, hydrobromide, tartrate, mesylate, acetate, maleate, oxalate, and the like. For example, pharmaceutically acceptable salts of the invention can be provided by compounds of Formula I when R$^{10}$ is —OR$^{13}$ and R$^{13}$ is a cation, and/or when R$^1$ is —OR$^{18}$. Similarly, pharmaceutically acceptable salts of the invention can be provided by compounds of Formula II at the hydroxyl group at the C4 position of the thiocoumarin, and/or at the carboxylic acid moiety by methods well known in the art. The term "cation" refers to a positively charged organic and inorganic counter ion, and includes, by way of example only, sodium, potassium, calcium, magnesium, ammonium, tetraalkylammonium, and the like.

The terms "stereoisomer" or "stereoisomers" refer to compounds that differ in the chirality of one or more stereocenters. Stereoisomers include enantiomers (compounds are non-superimposable mirror images) and diastereomers (compounds having more than one stereogenic center that are non-mirror images of each other and wherein one or more stereogenic center differs between the two stereoisomers). The compounds of the invention can be present as a mixture of stereoisomers or as a single stereoisomer.

The term "tautomer" refers to alternate forms of a compound that differ in the position of a proton, such as enol, keto, and imine enamine tautomers, or the tautomeric forms of heteroaryl groups containing a ring atom attached to both a ring NH moiety and a ring =N moiety such as pyrazoles, imidazoles, benzimidazoles, triazoles, and tetrazoles.

The term "prodrug" as used herein, refers to compounds of Formula I or II that include chemical groups which, in vivo, can be converted into the carboxylate group adjacent to the —C($R^3$)($R^4$) substituent in compounds of Formula I and II, and/or can be split off from the amide N-atom and/or can be split off from the $R^1$ atom to provide for the active drug, a pharmaceutically acceptable salt thereof, or a biologically active metabolite thereof. Suitable groups are well known in the art and particularly include: for the carboxylic acid moiety, a prodrug selected from, e.g., esters including, but not limited to, those derived from alkyl alcohols, substituted alkyl alcohols, hydroxy substituted aryls and heteroaryls and the like; amides, particularly amides derived from amines of the Formula HN$R^{200}R^{210}$ where $R^{200}$ and $R^{210}$ are independently hydrogen, alkyl, substituted alkyl, aryl, substituted aryl, and the like; hydroxymethyl, aldehyde and derivatives thereof.

The term "excipient" as used herein means an inert or inactive substance used in the production of pharmaceutical products or other tablets, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

4. Compound Preparation

The compounds of this invention can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

Synthesis of Compounds of the Invention

The compounds of this invention are preferably prepared by, but are not limited to, the synthetic protocols illustrated in Scheme A. In Scheme A, the substituents R, $R^{20}$, $R^2$, $R^3$, $R^4$, $R^5$, $R^{10}$, $R^{11}$, $R^{12}$, and $R^{13}$ are as defined herein.

amino acid (particularly, but not limited to, glycine or alanine or their corresponding salts). The reaction is conducted under conventional coupling conditions well known in the art. In one embodiment, the reaction is conducted in the presence of sodium methoxide, sodium ethoxide or another suitable base in methanol, DMF or another suitable solvent under elevated reaction temperatures and particularly at reflux. The reaction is continued until it is substantially complete which typically occurs within about 1 to 72 h. Alternatively, the reaction can

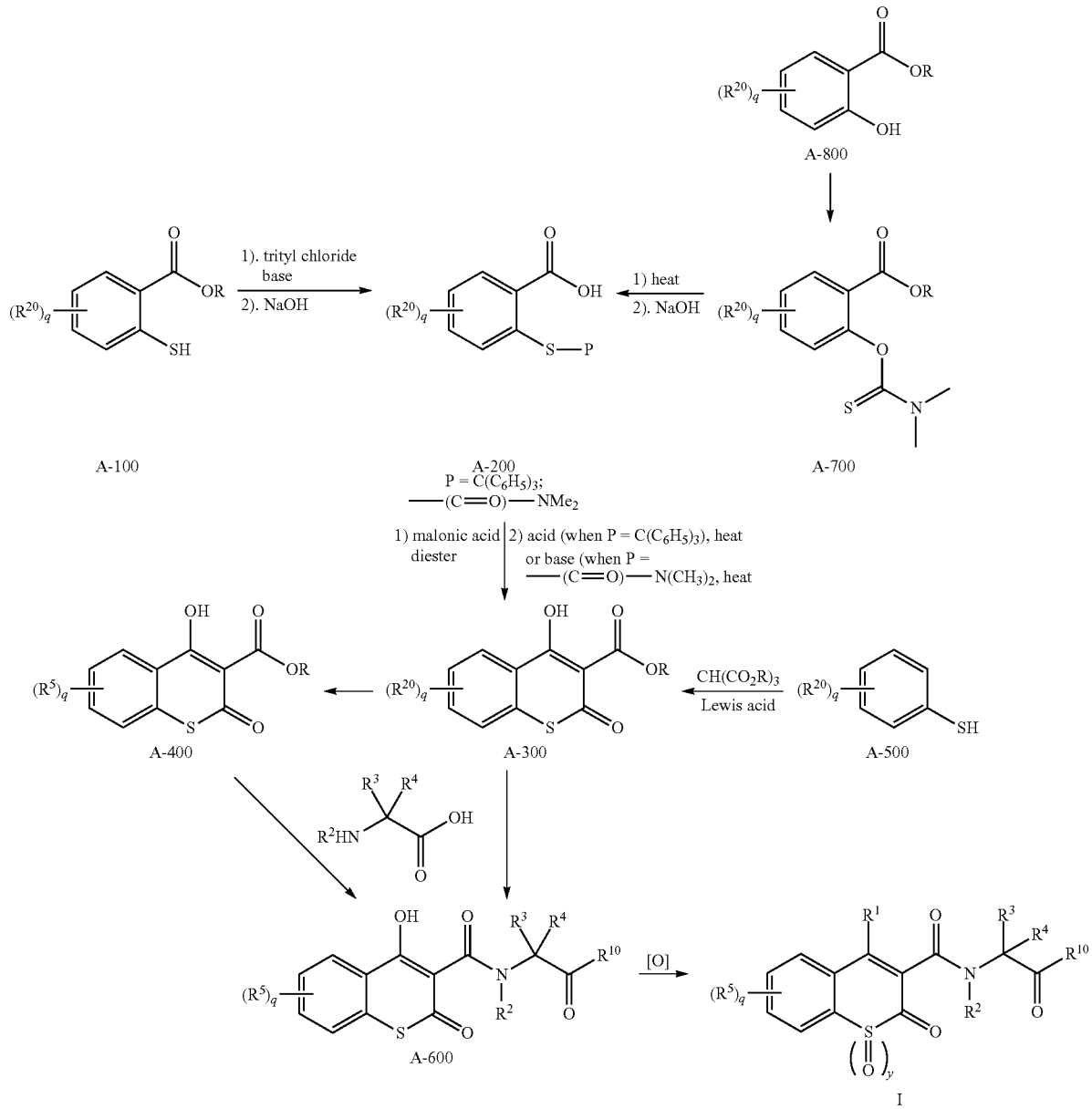

Scheme A

Compounds A-600 (when $R^{10}$=—OH) can be modified to A-600 (when $R^{10}$=—$NR^{11}R^{12}$) or A-600 (when $R^{10}$=—$OR^{13}$) under conventional amidation or esterification, respectively, conditions well known in the art. Compounds A-300 and A-400 (wherein R refers to a suitable protecting group such as methyl, ethyl, etc.) are reacted with at least a stoichiometric amount and preferably an excess of a suitable alphabe performed at elevated temperatures in a microwave oven. Upon reaction completion, the compounds A-600 can be recovered by conventional techniques such as neutralization, extraction, precipitation, chromatography, filtration and the like.

Compounds A-400 for use in the reactions depicted in Scheme A, can be prepared by reacting compounds A-300

($R^{20}$ is preferably, but not limited to, Cl, Br, and I) with reagents $R^SM$, where M is a suitable functional group such as, but not limited to, boronic acids or their derivatives such as $C_6H_4B(OH)_2$; organozinc compounds such as benzylzinc bromide; organomagnesium compounds such as benzyl magnesium bromide; organotin compounds such as tributylphenyltin; hydroxyl; amino; thio, and the like. The reaction is typically conducted in the presence of suitable catalyst such as a palladium catalyst including $Pd(PPh_3)_4$, $Cl_2Pd(PPh_3)_2$ or tris(dibenzylideneacetone)dipalladium(0), or a copper catalyst such as CuCl, and if required, suitable mediators, co-catalysts and/or bases known to one skilled in the art using suitable solvents/solvent mixtures. Upon reaction completion, A-400 can be recovered by conventional techniques such as neutralization, extraction, precipitation, chromatography, filtration, and the like; or, alternatively, used in the next step without purification and/or isolation.

Compounds A-300 for use in the reactions depicted in Scheme A, can be prepared by treatment of compounds A-200 via carbodiimide-mediated alkylation with a suitable malonic acid diester (preferably, but not limited to the dimethyl or diethyl ester), and subsequent acid-mediated cyclization reaction using a suitable acid (preferably, but not limited to, hydrochloric acid under elevated temperature) or base-mediated cyclization reaction using a suitable base (preferably, but not limited to, sodium methoxide in methanol under elevated temperature) under reaction conditions well known to one skilled in the art. Alternatively, compounds A-300 can be synthesized starting with compounds A-500 via acylation and subsequent cyclization with, for example, 2-ethoxycarbonyl-malonic acid diethyl ester in the presence of a Lewis acid (preferably, but not limited to tin tetrachloride) under elevated temperature.

Alternatively, compounds A-300 can be prepared using the synthetic protocols illustrated in Scheme B. In Scheme B, the substituents R, $R^{20}$ and q are as defined herein.

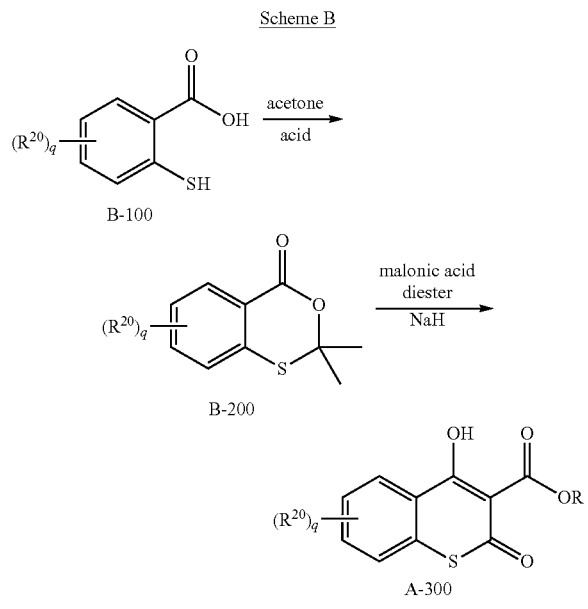

Scheme B

Alternatively, compound A-300 can be prepared from compound B-200 by treatment of compound B-200 with a suitable malonic acid diester (preferably, but not limited to, the dimethyl or diethyl ester) in the presence of a base (preferably, but not limited to, sodium hydride) using conditions well known to one skilled in the art (preferably, but not limited to, DMF at elevated temperature). Compound B-200 can be prepared from compound B-100 by treatment of compound B-100 with acetone or 2,2-dimethoxypropane in the presence of a suitable acid (preferably, but not limited to, camphor sulfonic acid) under conditions well known to one skilled in the art (preferably, but not limited to, acetone and camphor sulfonic acid at elevated temperature).

Upon completion of either of the above reactions, the compounds A-300 can be recovered by conventional techniques such as neutralization, extraction, precipitation, chromatography, filtration and the like; or, alternatively, used in the next step without purification and/or isolation.

Compounds A-200 for use in the reactions depicted in Scheme A, can be prepared first by protection of the thiophenolic group of compounds A-100 followed by hydrolysis. This is preferably done by, but not limited to, the transformation of A-100 to the corresponding tritylsulfanyl using conditions known to one skilled in the art (e.g., with trityl chloride and a suitable base at room temperature) and subsequent hydrolysis of the carboxylic ester functional group using an alkali hydroxide. Alternatively, compound A-200 (when P=—(C=O)—N(CH$_3$)$_2$) can also be prepared from pyrolytic rearrangement of A-700 followed by carboxylic ester soaponification. This pyrolytic rearrangement of O-aryl diarkylthiocarbamates to S-aryl dialkylcarbamates is preferably done thermally or by microwave irradiation of compound A-700 with or without the presence of a suitable solvent (e.g. bromobenzene). And subsequent hydrolysis of the carboxylic ester functional group was done using an alkali hydroxide. Upon reaction completion, A-200 can be recovered by conventional techniques such as neutralization, extraction, precipitation, chromatography, filtration, and the like; or, alternatively, used in the next step without purification and/or isolation.

Compound A-700 can be readily prepared by reaction of compound A-800 with a dialkyl-thiocarbamoyl chloride using conditions known to one skilled in the art (e.g. with a suitable base such as DABCO in DMF at room temperature).

The compounds A-100, A-500 and A-800 for use in the reactions depicted in Scheme A are either available from commercial sources or can be prepared according to known literature procedures.

Other modifications to arrive at compounds of this invention are well within the skill of the art. For example, modification of the C-4 hydroxy group may be done by conventional means to corresponding ethers, acyloxy, and the like, to provide compounds of Formula I. In addition, the thio moiety can be oxidized to provide compounds of Formula I using methods well known to those of skill in the art.

Alternatively, the compounds of this invention can be prepared using the synthetic protocols illustrated in Scheme C. In Scheme C, the substituents R, $R^{20}$, $R^2$, $R^3$, $R^4$, $R^5$ $R^{10}$, $R^{11}$, $R^{12}$, $R^{13}$, q and y are as defined herein.

Scheme C

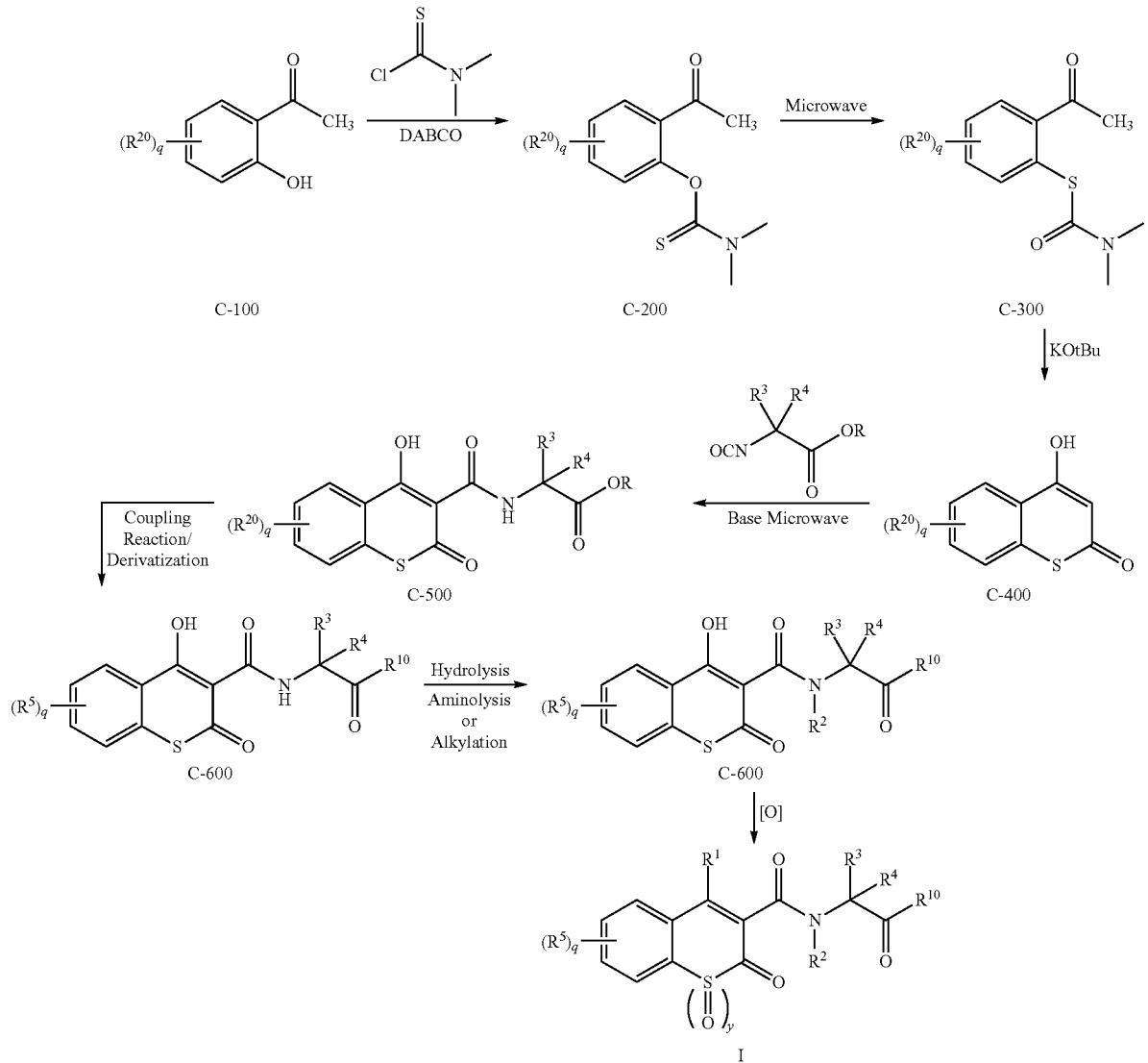

Compounds C-600 (wherein R refers to a suitable protecting group such as methyl, ethyl, etc.) for use in the reactions depicted in Scheme C, can be prepared by reacting compounds C-500 ($R^{20}$ is preferably, but not limited to Cl, Br, and I) with reagents $R^5M$, where M is a suitable functional group such as, but not limited to, boronic acids or their derivatives such as $C_6H_4B(OH)_2$; organozinc compounds such as benzylzinc bromide; organomagnesium compounds such as benzyl magnesium bromide; organotin compounds such as tributylphenyltin; hydroxyl; amino; or thio, and the like. The reaction is typically conducted in the presence of suitable catalyst such as a palladium catalyst including $Pd(PPh_3)_4$, $PdCl_2(PPh_3)_2$ or tris(dibenzylideneacetone)dipalladium(0), and the like, or a copper catalyst such as CuCl, and if required suitable mediator, co-catalyst and/or base known to one skilled in the art using suitable solvents/solvent mixtures. Upon reaction completion, C-600 can be recovered by conventional techniques such as neutralization, extraction, precipitation, chromatography, filtration, and the like; or, alternatively, used in the next step without purification and/or isolation. Compounds C-600 can be modified to A-600 (when $R^{10}=\!\!=\!\!-NR^{11}R^{12}$) or A-600 (when $R^{10}=\!\!=\!\!-OR^{13}$) under conventional aminolysis, hydrolysis, hydrogenation, or transesterification conditions well known in the art.

Compounds C-500 for use in the reactions depicted in Scheme C, can be prepared by reacting compounds C-400 ($R^{20}$ is preferably, but not limited to Cl, Br, and I) with reagents including, but not limited to, isocyanates, isothiocyanates, and acyl halides in the presence of a suitable base such as triethylamine and, if required, facilitated by microwave irradiation, sonication or appropriate methods known to one skilled in the art using suitable solvents/solvent mixtures. Upon reaction completion, C-500 can be recovered by conventional techniques such as neutralization, extraction, precipitation, chromatography, filtration, and the like; or, alternatively, used in the next step without purification and/or isolation.

Compounds C-400 for use in the reactions depicted in Scheme C, can be prepared by treatment of compounds C-300 with strong bases such as potassium tert-butoxide in suitable solvents using conditions well known to one skilled in the art. Upon completion of either of the above reactions, the compounds C-300 can be recovered by conventional techniques such as neutralization, extraction, precipitation, chromatography, filtration and the like; or, alternatively, used in the next step without purification and/or isolation.

Compounds C-300 for use in the reactions depicted in Scheme C, can be prepared thermally or by microwave irradiation of compounds C-200 either neat or in a suitable solvent using conditions known to one skilled in the art. Upon reaction completion, C-300 can be recovered by conventional techniques such as neutralization, extraction, precipitation, chromatography, filtration, and the like; or, alternatively, used in the next step without purification and/or isolation.

Compounds C-200 for use in the reactions depicted in Scheme C, can be prepared by treatment of compounds C-100 with N,N-dimethylthiocarbamoyl chloride or similar reagents in the presence of an appropriate base such as 1,4-diazabicyclo[2.2.2]octane (DABCO) in a suitable solvent using conditions known to one skilled in the art. Upon reaction completion, C-300 can be recovered by conventional techniques such as neutralization, extraction, precipitation, chromatography, filtration, and the like; or, alternatively, used in the next step without purification and/or isolation.

The compounds C-100 for use in the reactions depicted in Scheme C are available from commercial sources.

Other modifications to arrive at compounds of this invention are well within the skill of the art. For example, modification of the C-4 hydroxy group may be done by conventional means to corresponding ethers, acyloxy etc. to provide compounds of Formula I. In addition, the thio moiety can be oxidized to provide compounds of Formula I using methods well known to those of skill in the art.

5. Use of Compounds of the Invention

The compounds of the present invention can be used to inhibit HIF hydroxylase activity, thereby modulating the stability and/or activity of HIF and activating HIF-regulated gene expression. The compounds can be used in methods to treat, pretreat, or delay progression or onset of conditions associated with HIF including, but not limited to, anemia and various aspects of ischemic, and hypoxic conditions. In various embodiments, the compound is administered immediately following a condition associated with ischemia, e.g., myocardial infarction, pulmonary embolism, intestinal infarction, ischemic stroke, renal ischemic-reperfusion injury, cardiac cirrhosis, macular degeneration, pulmonary embolism, acute respiratory failure, neonatal respiratory distress syndrome, and congestive heart failure. In another embodiment, the compound is administered immediately after a trauma or injury. In other embodiments, the compound can be administered to a subject based on predisposing conditions, e.g., hypertension, diabetes, occlusive arterial disease, chronic venous insufficiency, Raynaud's disease, chronic skin ulcers, cirrhosis, congestive heart failure, and systemic sclerosis. In still other embodiments, compounds may be administered to pretreat a subject to decrease or prevent the development of tissue damage associated with ischemia or hypoxia.

In particular embodiments, the compounds of the present invention can be used to increase endogenous erythropoietin (EPO). The compounds can be administered to prevent, pretreat, or treat EPO-associated conditions, including, e.g., conditions associated with anemia and neurological disorders. Conditions associated with anemia include disorders such as acute or chronic kidney disease, diabetes, cancer, ulcers, infection with virus, e.g., HIV, bacteria, or parasites; inflammation, etc. Anemic conditions can further include those associated with procedures or treatments including, e.g., radiation therapy, chemotherapy, dialysis, and surgery. Disorders associated with anemia additionally include abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

6. Biological Testing

The biological activity of the compounds of the invention may be assessed using any conventionally known methods. Suitable assay methods are well known in the art. The following assays are presented only as examples and are not intended to be limiting. The compounds of the invention are active in at least one of the following assays.

i. Cell-based HIFα Stabilization Assay

Human cells derived from various tissues are separately seeded into 35 mm culture dishes, and grown at 37° C., 20% $O_2$, 5% $CO_2$ in standard culture medium, e.g., DMEM (Dulbecco's modification of Eagle's medium), 10% FBS (fetal bovine serum). When cell layers reach confluence, the media is replaced with OPTI-MEM media (Invitrogen Life Technologies, Carlsbad Calif.), and cell layers are incubated for approximately 24 hours in 20% $O_2$, 5% $CO_2$ at 37° C. Compound or 0.013% DMSO (dimethyl sulfoxide) is then added to existing medium and incubation is continued overnight.

Following incubation, the media is removed, centrifuged, and stored for analysis (see VEGF and EPO assays below). The cells are washed two times in cold phosphate buffered saline (PBS) and then lysed in 1 mL of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates are centrifuged at 3,000×g for 5 minutes at 4° C., and the cytosolic fractions (supernatant) are collected. The nuclei (pellet) are resuspended and lysed in 100 µL of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) are collected.

Nuclear fractions are analyzed for HIF-1α using a QUANTIKINE immunoassay (R&D Systems, Inc., Minneapolis Minn.) according to the manufacturer's instructions.

ii. Cell-based VEGF and EPO ELISA Assays

Conditioned media collected from cell cultures as described above is analyzed for vascular endothelial growth factor (VEGF) and/or erythropoietin (EPO) expression using an appropriate QUANTIKINE immunoassay (R&D Systems) according to the manufacturer's instructions.

iii. HIF-PH assay

Ketoglutaric acid α-[1-$^{14}$C]-sodium salt, alpha-ketoglutaric acid sodium salt, and HPLC purified peptide may be obtained from commercial sources, e.g., Perkin-Elmer (Wellesley Mass.), Sigma-Aldrich, and SynPep Corp. (Dublin Calif.), respectively. Peptides for use in the assay may be fragments of HIFα as described above or as disclosed in International Publication WO 2005/118836, incorporated by reference herein. For example, a HIF peptide for use in the HIF-PH assay is [methoxycoumarin]-DLDLEALAPYIPAD-DDFQL-amide (SEQ ID NO:2). HIF-PH, e.g., HIF-PH2 (EGLN1), can be expressed in, e.g., insect Hi5 cells, and partially purified, e.g., through a SP ion exchange chromatography column. Enzyme activity is determined by capturing $^{14}CO_2$ using an assay described by Kivirikko and Myllyla (1982, *Methods Enzymol*. 82:245-304). Assay reactions contain 50 mM HEPES (pH 7.4), 100 μM α-ketoglutaric acid sodium salt, 0.30 μCi/mL ketoglutaric acid α-[1-$^{14}$C]-sodium salt, 40 μM FeSO$_4$, 1 mM ascorbate, 1541.8 units/mL Catalase, with or without 50 μM peptide substrate and various concentrations of compound of the invention. Reactions are initiated by addition of HIF-PH enzyme.

The peptide-dependent percent turnover is calculated by subtracting percent turnover in the absence of peptide from percent turnover in the presence of substrate peptide. Percent inhibition and IC$_{50}$ are calculated using peptide-dependent percent turnover at given inhibitor concentrations. Calculation of IC$_{50}$ values for each inhibitor is conducted using GraFit software (Erithacus Software Ltd., Surrey UK).

Representative compounds of the invention were analyzed using the HIF-PH assay described above. Table 1 presents enzyme inhibition data for exemplary compounds against HIF-PH2, a representative HIF prolyl hydroxylase. By inhibiting HIF prolyl hydroxylase, compounds of the invention stabilize HIFα, which then combines with HIFβ to form an active transcription factor that increases expression of various genes involved in numerous beneficial cellular processes.

TABLE 1

| No. | Name | Concentration (μM) | % Inhibition HIF PH2 |
|---|---|---|---|
| 1 | [(4-Hydroxy-7-methoxy-2-oxo-2H-thiochromene-3-carbonyl)-amino]-acetic acid | 50 | 97.31 |
| 2 | [(4-Hydroxy-6,7-dimethoxy-2-oxo-2H-thiochromene-3-carbonyl)-amino]-acetic acid | 200 | 99.40 |
| 3 | [(4-Hydroxy-2-oxo-2H-thiochromene-3-carbonyl)-amino]-acetic acid | 200 | 99.17 |
| 4 | [(6-Fluoro-4-hydroxy-2-oxo-2H-thiochromene-3-carbonyl)-amino]-acetic acid | 200 | 100.24 |
| 5 | [(7-bromo-4-hydroxy-2-oxo-2H-thiochromene-3-carbonyl)-amino]-acetic acid | 12.5 | 97.58 |
| 6 | [(4-Hydroxy-7-methyl-2-oxo-2H-thiochromene-3-carbonyl)-amino]-acetic acid | 12.5 | 94.46 |
| 7 | {[4-Hydroxy-7-(4-methoxy-phenyl)-2-oxo-2H-thiochromene-3-carbonyl]-amino}-acetic acid | 12.5 | 98.74 |
| 8 | {[4-Hydroxy-7-(3-methoxy-phenyl)-2-oxo-2H-thiochromene-3-carbonyl]-amino}-acetic acid | 50 | 97.50 |
| 9 | {[4-Hydroxy-7-(2-methoxy-phenyl)-2-oxo-2H-thiochromene-3-carbonyl]-amino}-acetic acid | 50 | 97.18 |
| 10 | {[7-(3,5-Dichloro-phenyl)-4-hydroxy-2-oxo-2H-thiochromene-3-carbonyl]-amino}-acetic acid | 50 | 96.67 |
| 11 | {[4-Hydroxy-2-oxo-7-(4-trifluoromethyl-phenyl)-2H-thiochromene-3-carbonyl]-amino}-acetic acid | 50 | 95.75 |
| 12 | [(4-Hydroxy-2-oxo-7-phenyl-2H-thiochromene-3-carbonyl)-amino]-acetic acid | 50 | 96.82 |
| 13 | {[7-(4-Fluoro-phenyl)-4-hydroxy-2-oxo-2H-thiochromene-3-carbonyl]-amino}-acetic acid | 50 | 99.65 |
| 14 | [(4-Hydroxy-2-oxo-7-pyrimidin-5-yl-2H-thiochromene-3-carbonyl)-amino]-acetic acid | 50 | 99.49 |
| 15 | [(4-Hydroxy-2-oxo-7-pyridin-3-yl-2H-thiochromene-3-carbonyl)-amino]-acetic acid, sodium salt | 50 | 95.25 |
| 16 | {[7-(5-Fluoro-pyridin-3-yl)-4-hydroxy-2-oxo-2H-thiochromene-3-carbonyl]-amino}-acetic acid | 50 | 95.38 |
| 17 | {[7-(3-Chloro-4-fluoro-phenyl)-4-hydroxy-2-oxo-2H-thiochromene-3-carbonyl]-amino}-acetic acid | 50 | 92.76 |
| 18 | [(4-Hydroxy-7-naphthalen-2-yl-2-oxo-2H-thiochromene-3-carbonyl)-amino]-acetic acid | 50 | 87.89 |
| 19 | [(4-Hydroxy-2-oxo-7-p-tolyl-2H-thiochromene-3-carbonyl)-amino]-acetic acid | 50 | 92.06 |
| 21 | [(7-Fluoro-4-hydroxy-2-oxo-2H-thiochromene-3-carbonyl)-amino]-acetic acid | 12.5 | 91.06 |
| 22 | [(6-Chloro-4-hydroxy-8-methyl-2-oxo-2H-thiochromene-3-carbonyl)-amino]-acetic acid | 50 | 95.56 |
| 23 | [(4-Hydroxy-8-methyl-2-oxo-2H-thiochromene-3-carbonyl)-amino]-acetic acid | 50 | 97.50 |
| 26 | [(7-Butoxy-4-hydroxy-2-oxo-2H-thiochromene-3-carbonyl)-amino]-acetic acid | 12.5 | 96.21 |
| 27 | [(6-bromo-4-hydroxy-2-oxo-2H-thiochromene-3-carbonyl)-amino]-acetic acid | 67 | 100.00 |
| 28 | 2-(S)-[(6-Bromo-4-hydroxy-2-oxo-2H-thiochromene-3-carbonyl)-amino]-propionic acid | 67 | 98.00 |
| 29 | {[7-(3,5-Bis-trifluoromethyl-phenyl)-4-hydroxy-2-oxo-2H-thiochromene-3-carbonyl]-amino}-acetic acid | 67 | 96.37 |
| 30 | {[7-(3-Fluoro-phenyl)-4-hydroxy-2-oxo-2H-thiochromene-3-carbonyl]-amino}-acetic acid | 67 | 99.11 |
| 31 | 2-(S)-{[7-(3-Fluoro-phenyl)-4-hydroxy-2-oxo-2H-thiochromene-3-carbonyl]-amino}-propionic acid | 67 | 98.42 |
| 32 | {[4-Hydroxy-2-oxo-7-(2-trifluoromethyl-phenyl)-2H-thiochromene-3-carbonyl]-amino}-acetic acid | 67 | 93.16 |
| 33 | {[6-(3,5-Bis-trifluoromethyl-phenyl)-4-hydroxy-2-oxo-2H-thiochromene-3-carbonyl]-amino}-acetic acid | 67 | 99.39 |
| 34 | {[4-Hydroxy-2-oxo-6-(2-trifluoromethyl-phenyl)-2H-thiochromene-3-carbonyl]-amino}-acetic acid | 67 | 99.84 |
| 35 | {[4-Hydroxy-6-(4-methoxy-phenyl)-2-oxo-2H-thiochromene-3-carbonyl]-amino}-acetic acid | 67 | 99.06 |
| 36 | {[6-(2-Chloro-phenyl)-4-hydroxy-2-oxo-2H-thiochromene-3-carbonyl]-amino}-acetic acid | 67 | 99.69 |

TABLE 1-continued

| No. | Name | Concentration (µM) | % Inhibition HIF PH2 |
|---|---|---|---|
| 37 | {[6-(3-Fluoro-phenyl)-4-hydroxy-2-oxo-2H-thiochromene-3-carbonyl]-amino}-acetic acid | 67 | 98.40 |
| 38 | {[6-(4-Fluoro-phenyl)-4-hydroxy-2-oxo-2H-thiochromene-3-carbonyl]-amino}-acetic acid | 67 | 96.59 |
| 39 | {[4-Hydroxy-6-(2-methoxy-phenyl)-2-oxo-2H-thiochromene-3-carbonyl]-amino}-acetic acid | 67 | 94.72 |
| 40 | {[4-Hydroxy-2-oxo-6-(4-trifluoromethoxy-phenyl)-2H-thiochromene-3-carbonyl]-amino}-acetic acid | 50 | 94.82 |
| 41 | [(6-Benzoylamino-4-hydroxy-2-oxo-2H-thiochromene-3-carbonyl)-amino]-acetic acid | 50 | 100.00 |
| 42 | [(8-Benzyl-6-chloro-4-hydroxy-2-oxo-2H-thiochromene-3-carbonyl)-amino]-acetic acid | 50 | 100.00 |
| 43 | {[8-(3,5-Bis-trifluoromethyl-phenyl)-6-chloro-4-hydroxy-2-oxo-2H-thiochromene-3-carbonyl]-amino}-acetic acid | 50 | 100.00 |
| 44 | [(6-Chloro-4-hydroxy-2-oxo-8-phenyl-2H-thiochromene-3-carbonyl)-amino]-acetic acid | 50 | 100.00 |
| 45 | {[6-Chloro-4-hydroxy-8-(2-methyl-5-trifluoromethyl-2H-pyrazol-3-yl)-2-oxo-2H-thiochromene-3-carbonyl]-amino}-acetic acid | 50 | 100.00 |
| 46 | [(6-Chloro-4-hydroxy-2-oxo-8-pyridin-3-yl-2H-thiochromene-3-carbonyl)-amino]-acetic acid | 50 | 100.00 |
| 47 | [(8-Benzyl-4-hydroxy-2-oxo-2H-thiochromene-3-carbonyl)-amino]-acetic acid | 50 | 100.00 |
| 48 | {[8-(3,5-Bis-trifluoromethyl-phenyl)-4-hydroxy-2-oxo-2H-thiochromene-3-carbonyl]-amino}-acetic acid | 50 | 100.00 |
| 49 | {[4-Hydroxy-8-(2-methyl-5-trifluoromethyl-2H-pyrazol-3-yl)-2-oxo-2H-thiochromene-3-carbonyl]-amino}-acetic acid | 50 | 100.00 |
| 50 | [(4-Hydroxy-2-oxo-8-pyridin-3-yl-2H-thiochromene-3-carbonyl)-amino]-acetic acid | 50 | 98.75 |
| 51 | [(4-Hydroxy-2-oxo-8-phenyl-2H-thiochromene-3-carbonyl)-amino]-acetic acid | 50 | 98.80 |
| 52 | [(5-Fluoro-4-hydroxy-2-oxo-2H-thiochromene-3-carbonyl)-amino]-acetic acid | 50 | 98.48 |
| 53 | [(7-Cyclopropyl-4-hydroxy-2-oxo-2H-thiochromene-3-carbonyl)-amino]-acetic acid | 50 | 98.98 |
| 54 | {[4-Hydroxy-7-(2-methyl-5-trifluoromethyl-2H-pyrazol-3-yl)-2-oxo-2H-thiochromene-3-carbonyl]-amino}-acetic acid | 50 | 98.56 |
| 55 | 2-(S)-{[4-Hydroxy-7-(2-methyl-5-trifluoromethyl-2H-pyrazol-3-yl)-2-oxo-2H-thiochromene-3-carbonyl]-amino}-propionic acid | 50 | 94.47 |
| 56 | [(6-Chloro-4-hydroxy-2-oxo-8-phenylethynyl-2H-thiochromene-3-carbonyl)-amino]-acetic acid | 7.4 | 99.72 |
| 57 | 2-(S)-[(4-Hydroxy-2-oxo-2H-thiochromene-3-carbonyl)-amino]-propionic acid | 7.4 | 98.36 |
| 58 | [(6-Chloro-4-hydroxy-2-oxo-2H-thiochromene-3-carbonyl)-amino]-acetic acid | 7.4 | 96.82 |
| 59 | 2-(S)-[(6-Chloro-4-hydroxy-2-oxo-2H-thiochromene-3-carbonyl)-amino]-propionic acid | 50 | 95.61 |
| 60 | [(7-Chloro-4-hydroxy-2-oxo-2H-thiochromene-3-carbonyl)-amino]-acetic acid | 50 | 96.48 |
| 61 | 2-(S)-[(7-Chloro-4-hydroxy-2-oxo-2H-thiochromene-3-carbonyl)-amino]-propionic acid | 50 | 100.00 |
| 62 | [(6-Benzyloxy-4-hydroxy-2-oxo-2H-thiochromene-3-carbonyl)-amino]-acetic acid | 50 | 100.00 |
| 63 | [(6-Cyclohexylmethoxy-4-hydroxy-2-oxo-2H-thiochromene-3-carbonyl)-amino]-acetic acid | 50 | 98.94 |
| 64 | [(6-Hexyloxy-4-hydroxy-2-oxo-2H-thiochromene-3-carbonyl)-amino]-acetic acid | 200 | 100.00 |

7. Pharmaceutical Formulations and Routes of Administration

The compositions of the present invention can be delivered directly or in pharmaceutical compositions or medicaments along with suitable carriers or excipients, as is well known in the art. Present methods of treatment can comprise administration of an effective amount of a compound of the invention to a subject in need; e.g., a subject having or at risk for anemia due to, e.g., chronic renal failure, diabetes, cancer, AIDS, radiation therapy, chemotherapy, kidney dialysis, or surgery; or, e.g., a subject having or at risk for ischemia due to, e.g., myocardial infarction, congestive heart failure, cardiac cirrhosis, pulmonary insufficiency, atherosclerosis, peripheral vascular disease, or the like. In a preferred embodiment, the subject is a mammalian subject, and in a most preferred embodiment, the subject is a human subject.

An effective amount of such compound, composition, or medicament can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, supra.

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure.

Pharmaceutically acceptable excipients are available in the art and include those listed in various pharmacopoeias. (See, e.g., the U.S. Pharmacopeia (USP), Japanese Pharmacopoeia (JP), European Pharmacopoeia (EP), and British pharmacopeia (BP); the U.S. Food and Drug Administration (www.fda.gov) Center for Drug Evaluation and Research (CEDR) publications, e.g., Inactive Ingredient Guide (1996); Ash and Ash, Eds. (2002) Handbook of Pharmaceutical Additives, Synapse Information Resources, Inc., Endicott N.Y.; etc.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms, and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid, or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methane and ethane, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the compounds of the invention are well-known in the art and include water-based solutions containing a base, such as, for example, sodium hydroxide, to form an ionized compound; sucrose or sodium chloride as a tonicity agent; and a buffer, for example, a buffer that contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics.

Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the $ED_{50}$ with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of compound or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack; or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Unless otherwise stated all temperatures are in degrees Celsius (° C.). Also, in these examples and elsewhere, abbreviations have the following meanings:

μL=Microliter
μM=Micromolar
μCi=MicroCurie
aq=Aqueous
atm=Atmosphere
br=Broad
δ=Chemical shift
d=Doublet
DABCO=1,4-diazabicyclo[2.2.2]octane
DCC=Dicyclohexylcarbodiimide
DCCU=Dicyclohexyl urea
DIAD=Diisopropyl azodocarboxylate
DMF=Dimethylformamide
DMSO=Dimethylsulfoxide
EDTA=Ethylenediamine tetraacetic acid
ESI MS=Electrospray Ionization Mass Spectrometry
EtOH=Ethanol
EtOAc=Ethyl acetate
g=Gram
h=Hour
HEPES=4-(2-Hydroxyethyl)-1-piperazineethanesulfonic acid
HOBT=1-Hydroxybenzotriazole
HPLC=High-performance liquid chromatography
Hz=Hertz
L=Liter
M=Molar
m=Multiplet
m/e=Mass peak
m/z=Mass to charge ratio
MeOH=Methanol
mg=Milligram
$MgSO_4$=Magnesium sulfate
MHz=Mega Hertz
min=Minute
mL=Milliliter
mM=Millimolar
mmol=Millimole
mol=Mole
MS=Mass spectroscopy
N=Normal
NaOMe=Sodium methoxide
NMR=Nuclear magnetic resonance
$PPh_3$=Triphenyl phosphine
$Pd(PPh_3)_2Cl$=Dichlorobis(triphenylphosphine)palladium (II) 2
$Pd(PPh_3)_4$=tetrakis(triphenylphosphine)palladium(0)
ppm=Parts per million
q=Quartet
rt=Room temperature
s=Singlet t=Triplet
TBAF=Tetrabutylammonium fluoride
THF=Tetrahydrofuran
xg=Centrifugal force (gravities)

Example 1

[(4-Hydroxy-7-methoxy-2-oxo-2H-thiochromene-3-carbonyl)-amino]-acetic acid a) 4-Hydroxy-7-methoxy-2-oxo-2H-thiochromene-3-carboxylic acid ethyl ester $SnCl_4$ was added to a neat mixture of 3-methoxy-benzenethiol (0.91 g, 6.5 mmol) and 2-ethoxycarbonyl-malonic acid diethyl ester (2.27 g, 9.77 mmol) in a 20-mL open vial. The reaction mixture was heated in a 210° C. oil bath for 2.5 h. After cooling, the reaction mixture was subjected to silica gel chromatography (3%-50% $EtOAc/CH_2Cl_2$) to provide 4-hydroxy-7-methoxy-2-oxo-2H-thiochromene-3-carboxylic acid ethyl ester (100 mg). MS ESI(+) m/e: 281.10 (M+1).

b) [(4-Hydroxy-7-methoxy-2-oxo-2H-thiochromene-3-carbonyl)-amino]-acetic acid

A mixture of 4-hydroxy-7-methoxy-2-oxo-2H-thiochromene-3-carboxylic acid ethyl ester (47 mg, 0.17 mmol) and sodium glycinate (81 mg, 0.84 mmol) in 2-methoxyethanol (5.6 mL) was refluxed overnight (20 h). The reaction mixture was concentrated, and the crude residue dissolved in water (60 mL), acidified to pH 3-4 using 1 N HCl and extracted with EtOAc. The organic layer was washed with brine, dried over $MgSO_4$, filtered and concentrated to provide [(4-hydroxy-7-methoxy-2-oxo-2H-thiochromene-3-carbonyl)-amino]-acetic acid (41 mg). MS ESI(−) m/e: 308.06 (M−1).

Example 2

[(4-Hydroxy-6,7-dimethoxy-2-oxo-2H-thiochromene-3-carbonyl)-amino]-acetic acid a) 4-Hydroxy-6,7-dimethoxy-2-oxo-2H-thiochromene-3-carboxylic acid ethyl ester 4-Hydroxy-6,7-dimethoxy-2-oxo-2H-thiochromene-3-carboxylic acid ethyl ester was prepared under conditions analogous to Example 1(a). MS ESI(+) m/e: 311.12 (M+1).

b) [(4-Hydroxy-6,7-dimethoxy-2-oxo-2H-thiochromene-3-carbonyl)-amino]-acetic acid

[(4-Hydroxy-6,7-dimethoxy-2-oxo-2H-thiochromene-3-carbonyl)-amino]-acetic acid was prepared under conditions analogous to Example 1(b). MS ESI(−) m/e: 338.14 (M−1).

Example 3

[(4-Hydroxy-2-oxo-2H-thiochromene-3-carbonyl)-amino]acetic acid a) 2-Tritylsulfanyl-benzoic acid methyl ester Triethylamine (2.65 g, 26.2 mmol) was slowly added to a mixture of 2-mercapto-benzoic acid methyl ester (4.0 g, 23.8 mmol) and trityl chloride (6.63 g, 23.8 mmol) in $CH_2Cl_2$ at rt. The reaction mixture was stirred at rt for 3 h and washed with water (100 mL). The two phases were separated and the aqueous layer was extracted with $CH_2Cl_2$ (50 mL). The combined organic layers were washed with brine, dried over $Na_2SO_4$, filtered and concentrated to provide 2-tritylsulfanyl-benzoic acid methyl ester (9.6 g), which was used directly to the next reaction without further purification. MS ESI(+) m/e: 411.15 (M+1).

b) 2-Tritylsulfanyl-benzoic acid

A mixture of 2-tritylsulfanyl-benzoic acid methyl ester (9.6 g, 23.4 mmol) and LiOH (4.0 g, 95.2 mmol) in 110 mL of $MeOH/THF/H_2O$ (1/2/1) was stirred at rt overnight. The reaction mixture was concentrated to remove most organic solvents and diluted with water (150 mL). The solid was filtered off and the filtrate acidified to pH 4-5 using 3 N HCl and then 1 N HCl. The precipitate was collected by filtration, rinsed with water and then dissolved in hot EtOAc (1 L). After cooling, the organic solution was dried over $MgSO_4$, filtered and concentrated to provide 2-tritylsulfanyl-benzoic acid (6.71 g). MS ESI(−) m/e: 395.12 (M−1).

c) 4-Hydroxy-2-oxo-2H-thiochromene-3-carboxylic acid methyl ester

To a mixture of 2-tritylsulfanyl-benzoic acid (4.0 g, 10.1 mmol) in anhydrous THF (39 mL) at 0° C. was added HOBT (1.37 g, 10.1 mmol) and then DCC (2.1 g, 10.1 mmol). The resulting mixture was stirred at 0° C. for 1 h and the suspension was refrigerated overnight at 3-5° C. The precipitated solid was filtered off to give Solution 1. In another flask, dimethylmalonate (1.33 g, 10.1 mmol) was dissolved in anhydrous THF (80 mL) and cooled to 0° C. To the mixture was added NaH solid (60% dispersed in mineral oil) (808 mg, 20.2 mmol) and the suspension was stirred at 0° C. for 15 min prior to the addition of Solution 1. The resulting mixture was stirred at 0° C. for 5 min and at rt for 3 h and then concentrated in vacuo. The residue was diluted with water (200 mL) and acidified to pH 3-4 using 1 N aqueous HCl. The resulting precipitate was collected, rinsed with water and then dissolved in $CH_2Cl_2$. The organic solution was washed with brine, dried over $MgSO_4$, filtered and concentrated to give an intermediate (4.66 g). Part of this intermediate (0.51 g) was treated with 8 ml of (1/1) MeOH/3 N aqueous HCl solution and refluxed for 4 h. The reaction mixture was diluted with 50 mL of water and extracted with EtOAc. The organic layer was washed with brine, dried over $MgSO_4$, filtered and concentrated. The crude product was purified by silica gel chromatography (3%-50% $EtOAc/CH_2Cl_2$) to provide 4-hydroxy-2-oxo-2H-thiochromene-3-carboxylic acid methyl ester (48 mg). MS ESI(−) m/e: 235.08 (M−1).

d) [(4-Hydroxy-2-oxo-2H-thiochromene-3-carbonyl)-amino]-acetic acid

A mixture of 4-hydroxy-2-oxo-2H-thiochromene-3-carboxylic acid methyl ester (105 mg, 0.44 mmol) and sodium glycinate (215 mg, 2.22 mmol) in 2-methoxyethanol (13 mL) was refluxed for 5 h. The reaction mixture was concentrated, and the crude residue dissolved in water (50 mL) and acidified to pH 3-4 using 1 N HCl. The precipitate was collected, rinsed with water and dried in vacuo to provide [(4-hydroxy-2-oxo- 2H-thiochromene-3-carbonyl)-amino]-acetic acid (80 mg). MS ESI(−) m/e: 278.10 (M−1).

Example 4

[(6-Fluoro-4-hydroxy-2-oxo-2H-thiochromene-3-carbonyl)-amino]-acetic acid a) 5-Fluoro-2-tritylsulfanyl-benzoic acid methyl ester 5-Fluoro-2-tritylsulfanyl-benzoic acid methyl ester was prepared under conditions analogous to Example 3(a). MS ESI(+) m/e: 443.17 (M+1).

b) 5-Fluoro-2-tritylsulfanyl-benzoic acid

A mixture of 5-fluoro-2-tritylsulfanyl-benzoic acid methyl ester (4.74 g, 11.2 mmol) and LiOH (1.74 g, 41.4 mmol) in 80 mL of MeOH/THF/H$_2$O (1/2/1) was stirred at rt overnight. The reaction mixture was acidified to pH 4 using 1 N HCl. The precipitate was collected by filtration, rinsed with water and dried in vacuo to provide 5-fluoro-2-tritylsulfanyl-benzoic acid (4.16 g). MS ESI(+) m/e: 415.13 (M+1).

c) 6-Fluoro-4-hydroxy-2-oxo-2H-thiochromene-3-carboxylic acid methyl ester

To a mixture of 5-fluoro-2-tritylsulfanyl-benzoic acid (4.10 g, 10.0 mmol) in anhydrous THF (40 mL) at 0° C. was added HOBT (1.35 g, 10.0 mmol) and then DCC (2.06 g, 10.0 mmol). The resulting mixture was stirred at 0° C. for 1 h and the suspension refrigerated overnight (3-5° C.). The precipitated solid was filtered off to give Solution 1. In another flask, dimethylmalonate (1.33 g, 10.1 mmol) was dissolved in anhydrous THF (70 mL) and cooled to 0° C. To the mixture was added NaH solid (60% dispersed in mineral oil) (808 mg, 20.2 mmol) and the suspension was stirred at 0° C. for 10 min prior to the addition of Solution 1. The resulting mixture was stirred at 0° C. for 10 min and at rt for 3 h, and was then concentrated. The residue was diluted with water (200 mL) and acidified to pH 3-4 using 1 N aqueous HCl. The precipitate was collected, rinsed with water and dried in vacuo to give an intermediate (3.5 g). The intermediate was treated with 80 mL of (1/1) MeOH/3 N HCl and refluxed for 2 h. The clear reaction solution was poured out and diluted with water (150 mL). Precipitate formed and was collected, rinsed with water and dried. The residue was purified by silica gel chromatography (3%-70% EtOAc/hexanes) to provide 6-fluoro-4-hydroxy-2-oxo-2H-thiochromene-3-carboxylic acid methyl ester (54 mg). MS ESI(−) m/e: 253.09 (M−1).

d) [(6-Fluoro-4-hydroxy-2-oxo-2H-thiochromene-3-carbonyl)-amino]-acetic acid

[(6-Fluoro-4-hydroxy-2-oxo-2H-thiochromene-3-carbonyl)-amino]-acetic acid was prepared under conditions analogous to Example 3(d). MS ESI(−) m/e: 295.92 (M−1).

Example 5

[(7-bromo-4-hydroxy-2-oxo-2H-thiochromene-3-carbonyl)-amino]-acetic acid a) 4-Bromo-2-dimethylthiocarbamoyloxy-benzoic acid methyl ester To a mixture of 4-bromo-2-hydroxy-benzoic acid methyl ester (Mori, N. et al, Bull Chem. Soc. Jpn. 1969, 42(2), 488-491) (29.3 g, 127 mmol) and dimethylthiocarbamoyl chloride (17.2 g, 140 mmol) in DMF at room temperature was added DABCO (21.3 g, 190 mmol). The resulting mixture, after being stirred at room temperature overnight, was diluted with water (1.25 L) and acidified to a pH of around 4 using 1 N HCl. The precipitate was collected, rinsed with water and dried in vacuo to provide 4-bromo-2-dimethylthiocarbamoyloxy-benzoic acid methyl ester as an off-white solid (36.8 g). $^1$H NMR (200 MHz, CDCl$_3$): δ (ppm)=7.84 (d, J=8.2 Hz, 1H), 7.43 (dd, J=8.6, 2.0 Hz, 1H), 7.29 (d, J=2.0 Hz, 1H), 3.83 (s, 3H), 3.45 (s, 3H), 3.38 (s, 3H).

b) 4-Bromo-2-dimethylcarbamoylsulfanyl-benzoic acid methyl ester

Solid 4-bromo-2-dimethylthiocarbamoyloxy-benzoic acid methyl ester was heated neat to 180° C. in a microwave reactor (CEM Discovery) (5 g, 15.7 mmol at a time for 7 reactions) for various period of times (ranging from 5 min to 40 min). All 7 reaction mixtures were combined and purified by silica gel chromatography (eluting with 50-60% EtOAc in CH$_2$Cl$_2$) to provide 4-bromo-2-dimethylcarbamoylsulfanyl-benzoic acid methyl ester 23.08 g. MS ESI(+) m/e: 320.04, 318.00 (M+1).

c) 4-Bromo-2-dimethylcarbamoylsulfanyl-benzoic acid

A mixture of 4-bromo-2-dimethylcarbamoylsulfanyl-benzoic acid methyl ester (2.04 g, 6.42 mmol) and lithium hydroxide hydrate (404 mg, 9.62 mmol) in (1/1/1) THF/MeOH/H$_2$O (21 mL) was stirred at room temperature for 6 h. The reaction mixture was concentrated to remove most organic solvents. The residue was diluted with water (100 mL) and extracted with EtOAc (20 mL), which is discarded. The aqueous layer was acidified to pH 3-4 using 1 N HCl and extracted with EtOAc (2×100 mL). The combined organic layers were washed with brine, dried over MgSO$_4$, filtered and concentrated to provide 4-bromo-2-dimethylcarbamoylsulfanyl-benzoic acid (1.67 g). $^1$H NMR (200 MHz, CDCl$_3$): δ ppm)=7.76 (m, 2H), 7.61 (dd, J=8.2, 2.0 Hz, 1H), 3.15 (br s, 3H), 3.06 (br s, 3H).

d) 2-(4-Bromo-2-dimethylcarbamoylsulfanyl-benzoyl)-malonic acid dimethyl ester

To a mixture of 4-bromo-2-dimethylcarbamoylsulfanyl-benzoic acid (12.1 g, 39.8 mmol) in THF (160 mL) at 0° C. was added DCC (8.2 g, 39.8 mmol), followed by HOBT (5.37 g, 39.8 mmol). The reaction mixture was stirred at 0° C. for 2 h and filtered to give Solution 1. In another flask, NaH (60% dispersed in mineral oil) (1.43 g, 59.7 mmol) was added to cold THF (320 mL, 0° C.) and added slowly dimethyl malonate (5.52 g, 41.79 mmol). The reaction mixture was stirred at 0° C. for 15 min until gas evolution ceased. To this mixture was added Solution 1. The resulting mixture was stirred at 0° C. for 5 min, then at room temperature for 2 h and concentrated. The residue was treated with water (600 mL) and acidified to pH 4-5 using 1 N HCl, extracted with EtOAc (2×300 mL) and the combined organic layers washed with brine, dried over MgSO$_4$, filtered and concentrated. The crude residue was purified by silica gel chromatography (1%-20% EtOAc in CH$_2$Cl$_2$) to provide 2-(4-bromo-2-dimethylcarbamoylsulfanyl-benzoyl)-malonic acid dimethyl ester (11.50 g). MS ESI(−) m/e: 417.93, 415.96 (M−1).

e) 7-Bromo-4-hydroxy-2-oxo-2H-thiochromene-3-carboxylic acid methyl ester

A mixture of 2-(4-bromo-2-dimethylcarbamoylsulfanyl-benzoyl)-malonic acid dimethyl ester (11.2 g, 26.79 mmol) in 0.5 M NaOMe/MeOH solution (214 mL) was heated to reflux for 6 h. After cooling overnight, the precipitated solid was collected by filtration and rinsed with MeOH followed by ether. The solid was dried in vacuo to provide 7-bromo-4-hydroxy-2-oxo-2H-thiochromene-3-carboxylic acid methyl ester (5.37 g) as a sodium salt. $^1$H NMR (200 MHz, DMSO-d$_6$): δ (ppm)=7.98 (d, J=8.5 Hz, 1H), 7.50 (d, J=1.9 Hz, 1H), 7.38 (dd, J=8.5, 1.8 Hz, 1H), 3.56 (s, 3H).

f) [(7-Bromo-4-hydroxy-2-oxo-2H-thiochromene-3-carbonyl)-amino]-acetic acid

[(7-Bromo-4-hydroxy-2-oxo-2H-thiochromene-3-carbonyl)-amino]-acetic acid was prepared under conditions analogous to Example 3(d). MS ESI(−) m/e: 355.94, 358.02 (M−1).

Example 6

[(4-Hydroxy-7-methyl-2-oxo-2H-thiochromene-3-carbonyl)-amino]-acetic acid a) 4-Hydroxy-7-methyl-2-oxo-2H-thiochromene-3-carboxylic acid methyl ester

To a mixture of 7-bromo-4-hydroxy-2-oxo-2H-thiochromene-3-carboxylic acid methyl ester (Example 5e) (150 mg, 0.48 mmol) in DMF was added tetramethyltin (254 mg, 1.43 mmol) and PdCl$_2$(PPh$_3$)$_2$ (17 mg, 0.024 mmol). The resulting mixture was purged with nitrogen gas for 20 seconds and heated in a 120-125° C. oil bath for 1 h. The reaction mixture was diluted with water (15 mL) and the suspended black solid was filtered off. The clear filtrate was acidified to pH 4 using 1 N HCl and extracted with EtOAc (2×). The combined organic layers were washed with brine, dried over MgSO$_4$, filtered and concentrated. The crude product was triturated with MeOH (1 mL) and the solid collected to provide 4-hydroxy-7-methyl-2-oxo-2H-thiochromene-3-carboxylic acid methyl ester (82 mg). $^1$H NMR (200 MHz, CDCl$_3$): δ (ppm)=15.20 (s, 1H), 8.23 (d, J=8.5 Hz, 1H), 7.17 (m, 2H), 4.00 (s, 3H), 2.44 (s, 3H).

b.) [(4-Hydroxy-7-methyl-2-oxo-2H-thiochromene-3-carbonyl)-amino]-acetic acid A mixture of 4-hydroxy-7-methyl-2-oxo-2H-thiochromene-3-carboxylic acid methyl ester (80 mg, 0.32 mmol) and sodium glycinate (310 mg, 3.2 mmol) in 2-methoxyethanol (10 mL) was refluxed for 3 h. The reaction mixture was concentrated and the crude residue dissolved in water (50 mL), acidified to pH 3-4 using 1 N HCl and extracted with EtOAc. The organic layer was washed with brine, dried over MgSO$_4$, filtered and concentrated to provide [(4-hydroxy-7-methyl-2-oxo-2H-thiochromene-3-carbonyl)-amino]-acetic acid (89 mg). MS ESI(−) m/e: 292.12 (M−1).

Example 7

{[4-Hydroxy-7-(4-methoxy-phenyl)-2-oxo-2H-thiochromene-3-carbonyl]-amino}-acetic acid a) 4-Hydroxy-7-(4-methoxy-phenyl)-2-oxo-2H-thiochromene-3-carboxylic acid methyl ester To a mixture of 7-bromo-4-hydroxy-2-oxo-2H-thiochromene-3-carboxylic acid methyl ester (Example 5e) (180 mg, 0.57 mmol) in dimethoxyethane (DME) (2.5 mL) was added 4-methoxyphenylboronic acid (104 mg, 0.69 mmol), Pd(PPh$_3$)$_4$ solid (66 mg, 0.06 mmol) and then 2M aqueous Na$_2$CO$_3$ solution (0.7 mL). The resulting mixture was purged with nitrogen gas for 1 min and heated to reflux for 2 h. After cooling the reaction mixture was diluted with water (50 mL) and acidified using 1 N HCl to pH 3-4. The precipitate was collected by filtration, rinsed with water and dissolved in CH$_2$Cl$_2$. The organic solution was washed with brine, dried over MgSO$_4$, filtered and concentrated. The crude product was triturated with MeOH (5 mL) and the solid collected, rinsed with MeOH (2 mL) and dried in vacuo to provide 4-hydroxy-7-(4-methoxy-phenyl)-2-oxo-2H-thiochromene-3-carboxylic acid methyl ester (139 mg). MS ESI(+) m/e: 343.11 (M+1).

b) {[4-Hydroxy-7-(4-methoxy-phenyl)-2-oxo-2H-thiochromene-3-carbonyl]-amino}-acetic acid {[4-Hydroxy-7-(4-methoxy-phenyl)-2-oxo-2H-thiochromene-3-carbonyl]-amino}-acetic acid was prepared under conditions analogous to Example 3(d). MS ESI(−) m/e: 384.15 (M−1).

Example 8

{[4-Hydroxy-7-(3-methoxy-phenyl)-2-oxo-2H-thiochromene-3-carbonyl]-amino}-acetic acid a) 4-Hydroxy-7-(3-methoxy-phenyl)-2-oxo-2H-thiochromene-3-carboxylic acid methyl ester 4-Hydroxy-7-(3-methoxy-phenyl)-2-oxo-2H-thiochromene-3-carboxylic acid methyl ester was prepared from 7-bromo-4-hydroxy-2-oxo-2H-thiochromene-3-carboxylic acid methyl ester (Example 5e) and 3-methoxyphenylboronic acid under conditions analogous to Example 7(a). MS ESI(−) m/e: 341.10 (M−1).

b) {[4-Hydroxy-7-(3-methoxy-phenyl)-2-oxo-2H-thiochromene-3-carbonyl]-amino}-acetic acid {[4-Hydroxy-7-(3-methoxy-phenyl)-2-oxo-2H-thiochromene-3-carbonyl]-amino}-acetic acid was prepared under conditions analogous to Example 6(b). The crude product was further triturated with hot acetonitrile and the solid collected to provide {[4-hydroxy-7-(3-methoxy-phenyl)-2-oxo-2H-thiochromene-3-carbonyl]-amino}-acetic acid. MS ESI(−) m/e: 384.12 (M−1).

Example 9

{[4-Hydroxy-7-(2-methoxy-phenyl)-2-oxo-2H-thiochromene-3-carbonyl]-amino}-acetic acid a) 4-Hydroxy-7-(2-methoxy-phenyl)-2-oxo-2H-thiochromene-3-carboxylic acid methyl ester 4-Hydroxy-7-(2-methoxy-phenyl)-2-oxo-2H-thiochromene-3-carboxylic acid methyl ester was prepared from 7-bromo-4-hydroxy-2-oxo-2H-thiochromene-3-carboxylic acid methyl ester (Example 5e) and 2-methoxyphenylboronic acid under conditions analogous to Example 7(a). MS ESI(−) m/e: 341.07 (M−1).

b) {[4-Hydroxy-7-(2-methoxy-phenyl)-2-oxo-2H-thiochromene-3-carbonyl]-amino}-acetic acid {[4-Hydroxy-7-(2-methoxy-phenyl)-2-oxo-2H-thiochromene-3-carbonyl]-amino}-acetic acid was prepared under conditions analogous to Example 6(b). The crude product was further triturated with acetonitrile and solid was collected to provide {[4-hydroxy-7-(2-methoxy-phenyl)-2-oxo-2H-thiochromene-3-carbonyl]-amino}-acetic acid. MS ESI (−) m/e: 384.08 (M−1).

Example 10

{[7-(3,5-Dichloro-phenyl)-4-hydroxy-2-oxo-2H-thiochromene-3-carbonyl]-amino}-acetic acid a) 7-(3,5-Dichloro-phenyl)-4-hydroxy-2-oxo-2H-thiochromene-3-carboxylic acid methyl ester 7-(3,5-Dichloro-phenyl)-4-hydroxy-2-oxo-2H-thiochromene-3-carboxylic acid methyl ester was prepared from 7-bromo-4-hydroxy-2-oxo-2H-thiochromene-3-carboxylic acid methyl ester (Example 5e) and 3,5-dichlorophenylboronic acid under conditions analogous to Example 7(a). The crude product was purified by silica gel chromatography (eluting with 5%-60% EtOAc in $CH_2Cl_2$) to provide 7-(3,5-dichloro-phenyl)-4-hydroxy-2-oxo-2H-thiochromene-3-carboxylic acid methyl ester. MS ESI(−) m/e: 378.98 (M−1).

b) {[7-(3,5-Dichloro-phenyl)-4-hydroxy-2-oxo-2H-thiochromene-3-carbonyl]-amino}-acetic acid {[7-(3,5-Dichloro-phenyl)-4-hydroxy-2-oxo-2H-thiochromene-3-carbonyl]-amino}-acetic acid was prepared under conditions analogous to Example 3(d). MS ESI(−) m/e: 421.96 (M−1).

Example 11

{[4-Hydroxy-2-oxo-7-(4-trifluoromethyl-phenyl)-2H-thiochromene-3-carbonyl]-amino}-acetic acid a) 4-Hydroxy-2-oxo-7-(4-trifluoromethyl-phenyl)-2H-thiochromene-3-carboxylic acid methyl ester 4-Hydroxy-2-oxo-7-(4-trifluoromethyl-phenyl)-2H-thiochromene-3-carboxylic acid methyl ester was prepared from 7-bromo-4-hydroxy-2-oxo-2H-thiochromene-3-carboxylic acid methyl ester (Example 5e) and 4-trifluoromethylphenylboronic acid under conditions analogous to Example 7(a). MS ESI(−) m/e: 379.05 (M−1).

b) {[4-Hydroxy-2-oxo-7-(4-trifluoromethyl-phenyl)-2H-thiochromene-3-carbonyl]-amino}-acetic acid {[4-Hydroxy-2-oxo-7-(4-trifluoromethyl-phenyl)-2H-thiochromene-3-carbonyl]-amino}-acetic acid was prepared under conditions analogous to Example 6(b). MS ESI(−) m/e: 422.06 (M−1).

Example 12

[(4-Hydroxy-2-oxo-7-phenyl-2H-thiochromene-3-carbonyl)-amino]-acetic acid a) 4-Hydroxy-2-oxo-7-phenyl-2H-thiochromene-3-carboxylic acid methyl ester 4-Hydroxy-2-oxo-7-phenyl-2H-thiochromene-3-carboxylic acid methyl ester was prepared from 7-bromo-4-hydroxy-2-oxo-2H-thiochromene-3-carboxylic acid methyl ester (Example 5e) and phenylboronic acid under conditions analogous to Example 7(a). $^1$H NMR (200 MHz, $CDCl_3$): δ (ppm)=15.26 (s, 1H), 8.40 (d, J=9.1 Hz, 1H), 7.65-7.45 (m, 7H), 4.02 (s, 3H).

b) [(4-Hydroxy-2-oxo-7-phenyl-2H-thiochromene-3-carbonyl)-amino]-acetic acid

[(4-Hydroxy-2-oxo-7-phenyl-2H-thiochromene-3-carbonyl)-amino]-acetic acid was prepared under conditions analogous to Example 3(d). The crude product was further triturated with acetonitrile and the solid collected to provide [(4-hydroxy-2-oxo-7-phenyl-2H-thiochromene-3-carbonyl)-amino]-acetic acid. MS ESI(−) m/e: 354.10 (M−1).

Example 13

{[7-(4-Fluoro-phenyl)-4-hydroxy-2-oxo-2H-thiochromene-3-carbonyl]-amino}-acetic acid a) 7-(4-Fluoro-phenyl)-4-hydroxy-2-oxo-2H-thiochromene-3-carboxylic acid methyl ester 7-(4-Fluoro-phenyl)-4-hydroxy-2-oxo-2H-thiochromene-3-carboxylic acid methyl ester was prepared from 7-bromo-4-hydroxy-2-oxo-2H-thiochromene-3-carboxylic acid methyl ester (Example 5e) and 4-fluorophenylboronic acid under conditions analogous to Example 7(a). $^1$H NMR (200 MHz, $CDCl_3$): δ (ppm)=15.27 (s, 1H), 8.39 (d, J=8.5 Hz, 1H), 7.60-7.50 (m, 4H), 7.21-7.17 (m, 2H), 4.02 (s, 3H).

b) {[7-(4-Fluoro-phenyl)-4-hydroxy-2-oxo-2H-thiochromene-3-carbonyl]-amino}-acetic acid {[7-(4-Fluoro-phenyl)-4-hydroxy-2-oxo-2H-thiochromene-3-carbonyl]-amino}-acetic acid was prepared under conditions analogous to Example 6(b). MS ESI(−) m/e: 372.09 (M−1).

Example 14

[(4-Hydroxy-2-oxo-7-pyrimidin-5-yl-2H-thiochromene-3-carbonyl)-amino]-acetic acid a) 4-Hydroxy-2-oxo-7-pyrimidin-5-yl-2H-thiochromene-3-carboxylic acid methyl ester To a mixture of 7-bromo-4-hydroxy-2-oxo-2H-thiochromene-3-carboxylic acid methyl ester (Example 5e) (220 mg, 0.70 mmol) in dimethoxyethane (DME) (3.1 mL) was added pyrimidine-5-yl boronic acid (104 mg, 0.84 mmol), $Pd(PPh_3)_4$ solid (65 mg, 0.08 mmol) and then 2M aqueous $Na_2CO_3$ solution (0.86 mL). The resulting mixture was purged with nitrogen gas for 1 min and heated to reflux for 2 h. After cooling, the reaction mixture was diluted with water (80 mL), acidified using 1 N HCl to pH 3-4 and extracted with EtOAc. The two phases were filtered through a pad of Celite® to form two clear layers. The organic layer was separated, washed with brine, dried over $MgSO_4$, filtered and concentrated. The crude product was triturated with MeOH (10 mL) and the solid collected, rinsed with MeOH (2 mL) and dried in vacuo to provide 4-hydroxy-2-oxo-7-pyrimidin-5-yl-2H-thiochromene-3-carboxylic acid methyl ester (79 mg). MS ESI(−) m/e: 313.09 (M−1).

b) [(4-Hydroxy-2-oxo-7-pyrimidin-5-yl-2H-thio-chromene-3-carbonyl)-amino]-acetic acid

[(4-Hydroxy-2-oxo-7-pyrimidin-5-yl-2H-thiochromene-3-carbonyl)-amino]-acetic acid was prepared under conditions analogous to Example 6(b). MS ESI(−) m/e: 356.11 (M−1).

Example 15

[(4-Hydroxy-2-oxo-7-pyridin-3-yl-2H-thio-chromene-3-carbonyl)-amino]-acetic acid, sodium salt a) 4-Hydroxy-2-oxo-7-pyridin-3-yl-2H-thio-chromene-3-carboxylic acid methyl ester 4-Hydroxy-2-oxo-7-pyridin-3-yl-2H-thiochromene-3-carboxylic acid methyl ester was prepared from 7-bromo-4-hydroxy-2-oxo-2H-thiochromene-3-carboxylic acid methyl ester (Example 5e) and 3-pyridyl-boronic acid under conditions analogous to Example 14(a). MS ESI(+) m/e: 314.12 (M+1).

b) [(4-Hydroxy-2-oxo-7-pyridin-3-yl-2H-thio-chromene-3-carbonyl)-amino]-acetic acid, sodium salt

[(4-Hydroxy-2-oxo-7-pyridin-3-yl-2H-thiochromene-3-carbonyl)-amino]-acetic acid, disodium salt was prepared under conditions analogous to Example 3(d). The neutral form product (100 mg) was treated with acetonitrile (3 mL) and water (10 mL). To the suspension mixture was added 2 equivalents of 1 N aqueous NaOH solution. The resulting clear solution was lyophilized to provide [(4-hydroxy-2-oxo-7-pyridin-3-yl-2H-thiochromene-3-carbonyl)-amino]-acetic acid, disodium salt (119 mg). $^1$H NMR (200 MHz, D$_2$O): δ (ppm)=8.61 (d, J=1.9 Hz, 1H), 8.34 (dd, J=5.1, 1.5 Hz, 1H), 8.12 (d, J=8.4 Hz, 1H), 7.94 (dd, J=6.3, 1.9 Hz, 1H), 7.57 (m, 2H), 7.35 (dd, J=8.1, 5.1 Hz, 1H), 3.80 (s, 2H).

Example 16

{[7-(5-Fluoro-pyridin-3-yl)-4-hydroxy-2-oxo-2H-thiochromene-3-carbonyl]-amino}-acetic acid a) 7-(5-Fluoro-pyridin-3-yl)-4-hydroxy-2-oxo-2H-thiochromene-3-carboxylic acid methyl ester 7-(5-Fluoro-pyridin-3-yl)-4-hydroxy-2-oxo-2H-thiochromene-3-carboxylic acid methyl ester was prepared from 7-bromo-4-hydroxy-2-oxo-2H-thiochromene-3-carboxylic acid methyl ester (Example 5e) and 5-fluoro-3-pyridyl-boronic acid under conditions analogous to Example 14(a). MS ESI(+) m/e: 332.08 (M+1).

b) {[7-(5-Fluoro-pyridin-3-yl)-4-hydroxy-2-oxo-2H-thiochromene-3-carbonyl]-amino}-acetic acid {[7-(5-Fluoro-pyridin-3-yl)-4-hydroxy-2-oxo-2H-thiochromene-3-carbonyl]-amino}-acetic acid was prepared under conditions analogous to Example 6(b). MS ESI(+) m/e: 375.14 (M+1).

Example 17

{[7-(3-Chloro-4-fluoro-phenyl)-4-hydroxy-2-oxo-2H-thiochromene-3-carbonyl]-amino}-acetic acid a) 7-(3-Chloro-4-fluoro-phenyl)-4-hydroxy-2-oxo-2H-thiochromene-3-carboxylic acid methyl ester 7-(3-Chloro-4-fluoro-phenyl)-4-hydroxy-2-oxo-2H-thiochromene-3-carboxylic acid methyl ester was prepared from 7-bromo-4-hydroxy-2-oxo-2H-thiochromene-3-carboxylic acid methyl ester (Example 5e) and 3-chloro-4-fluoro-phenylboronic acid under conditions analogous to Example 7(a). MS ESI(+) m/e: 365.10 (M+1).

b) {[7-(3-Chloro-4-fluoro-phenyl)-4-hydroxy-2-oxo-2H-thiochromene-3-carbonyl]-amino}-acetic acid {[7-(3-Chloro-4-fluoro-phenyl)-4-hydroxy-2-oxo-2H-thiochromene-3-carbonyl]-amino}-acetic acid was prepared under conditions analogous to Example 3(d). The crude product was triturated with CH$_2$Cl$_2$ and the solid collected and dried to provide {[7-(3-chloro-4-fluoro-phenyl)-4-hydroxy-2-oxo-2H-thiochromene-3-carbonyl]-amino}-acetic acid. MS ESI(−) m/e: 406.08 (M−1).

Example 18

[(4-Hydroxy-7-naphthalen-2-yl-2-oxo-2H-thio-chromene-3-carbonyl)-amino]-acetic acid a) 4-Hydroxy-7-naphthalen-2-yl-2-oxo-2H-thio-chromene-3-carboxylic acid methyl ester To a mixture of 7-bromo-4-hydroxy-2-oxo-2H-thiochromene-3-carboxylic acid methyl ester (Example 5e) (220 mg, 0.70 mmol) in dimethoxyethane (DME) (3.1 mL) was added naphthalen-2-yl-boronic acid (144 mg, 0.84 mmol), Pd(PPh$_3$)$_4$ solid (64 mg, 0.06 mmol) and then 2M aqueous Na$_2$CO$_3$ solution (0.86 mL). The resulting mixture was purged with nitrogen gas for 1 min and heated to reflux for 3 h. After cooling, the reaction mixture was diluted with water (100 mL) and acidified using 1 N HCl to pH 3-4. The precipitate was collected by filtration, rinsed with CH$_2$Cl$_2$ and the solid dried to provide 4-hydroxy-7-naphthalen-2-yl-2-oxo-2H-thiochromene-3-carboxylic acid methyl ester (119 mg). MS ESI(+) m/e: 363.19 (M+1).

b) [(4-Hydroxy-7-naphthalen-2-yl-2-oxo-2H-thio-chromene-3-carbonyl)-amino]-acetic acid

[(4-Hydroxy-7-naphthalen-2-yl-2-oxo-2H-thiochromene-3-carbonyl)-amino]-acetic acid was prepared under conditions analogous to Example 3(d). The crude product was triturated with MeOH and the solid collected and dried to provide [(4-hydroxy-7-naphthalen-2-yl-2-oxo-2H-thiochromene-3-carbonyl)-amino]-acetic acid. MS ESI(+) m/e: 406.14 (M+1).

Example 19

[(4-Hydroxy-2-oxo-7-p-tolyl-2H-thiochromene-3-carbonyl)-amino]-acetic acid a) 4-Hydroxy-2-oxo-7-p-tolyl-2H-thiochromene-3-carboxylic acid methyl ester 4-Hydroxy-2-oxo-7-p-tolyl-2H-thiochromene-3-carboxylic acid methyl ester was prepared from 7-bromo-4-hydroxy- 2-oxo-2H-thiochromene-3-carboxylic acid methyl ester (Example 5e) and 4-methyl-phenylboronic acid under conditions analogous to Example 7(a). $^1$H NMR (200 MHz, CDCl$_3$): δ (ppm)=15.23 (s, 1H), 8.38 (d, J=8.7 Hz, 1H), 7.64-7.51 (m, 4H), 7.38-7.26 (m, 2H), 4.02 (s, 3H), 2.41 (s, 3H).

b) [(4-Hydroxy-2-oxo-7-p-tolyl-2H-thiochromene-3-carbonyl)-amino]-acetic acid

[(4-Hydroxy-2-oxo-7-p-tolyl-2H-thiochromene-3-carbonyl)-amino]-acetic acid was prepared under conditions analogous to Example 3(d). MS ESI(+) m/e: 370.13 (M+1).

Example 20

[(7-Benzyl-4-hydroxy-2-oxo-2H-thiochromene-3-carbonyl)-amino]-acetic acid a) 7-Benzyl-4-hydroxy-2-oxo-2H-thiochromene-3-carboxylic acid methyl ester To a mixture of 7-bromo-4-hydroxy-2-oxo-2H-thiochromene-3-carboxylic acid methyl ester (Example 5e) (220 mg, 0.70 mmol) in THF (8 mL) was added potassium benzyltrifluoroborate (138 mg, 0.70 mmol), Cs$_2$CO$_3$ (682 mg, 2.09 mmol), PdCl$_2$(PPh$_3$)$_2$ (49 mg, 0.07 mmol) and then water (2 mL). The resulting mixture was refluxed overnight (18 h). After cooling, the reaction mixture was diluted with water (75 mL) and acidified using 1 N HCl to pH 4. The precipitate was collected, rinsed with water and the solid dissolved in CH$_2$Cl$_2$. The CH$_2$Cl$_2$ solution was dried over MgSO$_4$, filtered, concentrated and the crude product purified by silica gel chromatography (5%-100% EtOAc/CH$_2$Cl$_2$) to provide 7-benzyl-4-hydroxy-2-oxo-2H-thiochromene-3-carboxylic acid methyl ester (99 mg). $^1$H NMR (200 MHz, CDCl$_3$): δ (ppm)=15.2 (s, 1H), 8.25 (d, J=8.2 Hz, 1H), 7.36-7.16 (m, 7H), 4.04 (s, 2H), 4.00 (s, 3H).

b) [(7-Benzyl-4-hydroxy-2-oxo-2H-thiochromene-3-carbonyl)-amino]-acetic acid

[(7-Benzyl-4-hydroxy-2-oxo-2H-thiochromene-3-carbonyl)-amino]-acetic acid was prepared under conditions analogous to Example 3(d). MS ESI(−) m/e: 368.16 (M−1).

Example 21

[(7-Fluoro-4-hydroxy-2-oxo-2H-thiochromene-3-carbonyl)-amino]-acetic acid a) Dimethyl-thiocarbamic acid O-(2-acetyl-5-fluoro-phenyl)ester 1-(4-Fluoro-2-hydroxy-phenyl)ethanone (4 g, 25.95 mmol), DABCO (3.06 g, 27.25 mmol) and N,N-dimethylthiocarboamoyl chloride (3.4 g, 27.25 mmol) were placed together in a dry flask. Anhydrous DMF (10 mL) was added and the reaction was stirred overnight (18 h) at room temperature. The crude reaction mixture was poured onto a mixture of 1N HCl and ice. The oily residue that formed upon addition of the acid was extracted with ethyl acetate. The organic phase was washed sequentially with two volumes of water and one volume of brine and dried over sodium sulfate. The crude material was purified using silica gel chromatography (3%-10% ethyl acetate in hexanes) to provide dimethyl-thiocarbamic acid O-(2-acetyl-5-fluoro-phenyl) ester (5.9 g, 94%). $^1$H NMR (200 MHz, CDCl$_3$): 7.82 (1H, dd), 7.05 (1H, dt), 6.9 (1H, dd), 3.45 (3H, s), 3.39, (3H,$), 2.52 (3H, s).

b) Dimethyl-thiocarbamic acid S-(2-acetyl-5-fluoro-phenyl) ester

Dimethyl-thiocarbamic acid O-(2-acetyl-5-fluoro-phenyl) ester (5.1 g, 21.12 mmol) was heated to 180 C in a CEM Microwave apparatus for 75 min. The reaction was cooled and concentrated in vacuo. The crude residue was subjected to silica gel chromatography (10%-30% ethyl acetate in hexanes) to provide dimethyl-thiocarbamic acid S-(2-acetyl-5-fluoro-phenyl) ester (3.5 g, 69%). $^1$H NMR (200 MHz, CDCl$_3$): 7.62 (1H, dd), 7.33 (1H, dd), 7.1 (1H, dt), 3.05 (6H, br s), 2.57 (3H, s).

c) 7-Fluoro-4-hydroxy-thiochromen-2-one

Dimethyl-thiocarbamic acid S-(2-acetyl-5-fluoro-phenyl) ester (2.7 g, 11.2 mmol) was dissolved in dry THF (15 mL) and transferred via cannula to a flask containing 1M potassium tert-butoxide in THF (22.4 mL). The reaction was permitted to for 4 h at ambient temperature. The reaction mixture was concentrated in vacuo and dissolved in water. The aqueous layer was extracted with diethyl ether and the organic phase was discarded. The aqueous portion was acidified to pH 3 with 1N HCl, the precipitate collected via filtration and air dried to provide 7-fluoro-4-hydroxy-thiochromen-2-one (2.0 g, 91%) which was used without further purification. MS ESI(−) m/e: 195.209 (M−1).

d) [(7-Fluoro-4-hydroxy-2-oxo-2H-thiochromene-3-carbonyl)-amino]-acetic acid ethyl ester 7-Fluoro-4-hydroxy-thiochromen-2-one (2.0 g, 10.2 mmol) was dissolved in a mixture of triethylamine (1.7 mL, 12.23 mmol) and dichloromethane (50 mL). Isocyanato-acetic acid ethyl ester (1.4 mL, 12.23 mmol) was added to the solution and the reaction stirred overnight (18 h) at ambient temperature. The reaction mixture was acidified to pH 3 using 1N HCl and extracted with ethyl acetate. The organic phase was washed with brine, dried over sodium sulfate, and the crude residue purified by silica gel chromatography (10%-40% ethyl acetate in hexanes) to provide [(7-fluoro-4-hydroxy-2-oxo-2H-thiochromene-3-carbonyl)-amino]-acetic acid ethyl ester (900 mg, 30%). MS ESI(−) m/e: 324.117 (M−1).

e) [(7-Fluoro-4-hydroxy-2-oxo-2H-thiochromene-3-carbonyl)-amino]-acetic acid

[(7-Fluoro-4-hydroxy-2-oxo-2H-thiochromene-3-carbonyl)-amino]-acetic acid ethyl ester (150 mg, 0.461 mmol) was dissolved in a mixture of tetrahydrofuran (5 mL) and methanol (5 mL). 1N Sodium hydroxide (1.85 mL) was added to the solution and the reaction was stirred overnight (18 h) at ambient temperature. The reaction was concentrated in vacuo and the residue dissolved in water, treated with 1N HCl to pH 3 to precipitate the product, which was collected via filtration and dried to yield [(7-fluoro-4-hydroxy-2-oxo-2H-thiochromene-3-carbonyl)-amino]-acetic acid (100 mg, 75%.) MS ESI(−) m/e: 296.23 (M−1).

Example 22

[(6-Chloro-4-hydroxy-8-methyl-2-oxo-2H-thio-chromene-3-carbonyl)-amino]-acetic acid a) Dimethyl-thiocarbamic acid O-(2-acetyl-6-bromo-4-chloro-phenyl) ester

Dimethyl-thiocarbamic acid O-(2-acetyl-6-bromo-4-chloro-phenyl) ester was prepared under conditions analogous to Example 21(a) using 1-(3-Bromo-5-chloro-2-hydroxy-phenyl)-ethanone. MS ESI(−) m/e: 336.035 (M−1).

b) Dimethyl-thiocarbamic acid S-(2-acetyl-6-bromo-4-chloro-phenyl) ester

Dimethyl-thiocarbamic acid S-(2-acetyl-6-bromo-4-chloro-phenyl) ester was prepared under conditions analogous to Example 21(b). $^1$H NMR (200 MHz, CDCl$_3$): 7.74 (1H, d), 7.35 (1H, d), 3.12 (6H, br d), 2.54 (3H, s).

c) 8-Bromo-6-chloro-4-hydroxy-thiochromen-2-one

8-Bromo-6-chloro-4-hydroxy-thiochromen-2-one was prepared under conditions analogous to Example 21(c). MS ESI(−) m/e: 291.07 (M−1).

d) [(8-Bromo-6-chloro-4-hydroxy-2-oxo-2H-thio-chromene-3-carbonyl)-amino]-acetic acid ethyl ester

[(8-Bromo-6-chloro-4-hydroxy-2-oxo-2H-thiochromene-3-carbonyl)-amino]-acetic acid ethyl ester was prepared under conditions analogous to Example 21(d). MS ESI(−) m/e: 420.235 (M−1).

e) [(6-Chloro-4-hydroxy-8-methyl-2-oxo-2H-thio-chromene-3-carbonyl)-amino]-acetic acid ethyl ester

[(8-Bromo-6-chloro-4-hydroxy-2-oxo-2H-thiochromene-3-carbonyl)-amino]-acetic acid ethyl ester (500 mg, 1.19 mmol) was dissolved in anhydrous N,N-dimethylformamide (4 mL). Tetramethyl tin (247 μL, 1.783 mmol), dichloro(bis-triphenylphosphino) palladium (125 mg, 0.18 mmol), and 4 angstrom molecular sieves were added sequentially to the reaction. The reaction was sealed and heated to 120° C. in an oil bath for 45 min. The reaction was cooled, diluted with ethyl acetate, and partitioned with water. The organic phase was washed with water, brine, and dried over sodium sulfate. The crude material was purified by silica gel chromatography (15%-45% ethyl acetate in hexanes) to provide [(6-chloro-4-hydroxy-8-methyl-2-oxo-2H-thiochromene-3-carbonyl)-amino]-acetic acid ethyl ester (400 mg, 95%). MS ESI(−) m/e: 354.223 (M−1).

f) [(6-Chloro-4-hydroxy-8-methyl-2-oxo-2H-thio-chromene-3-carbonyl)-amino]-acetic acid

[(6-Chloro-4-hydroxy-8-methyl-2-oxo-2H-thio-chromene-3-carbonyl)-amino]-acetic acid was prepared under conditions analogous to Example 21(e). MS ESI(−) m/e: 326.21 (M−1).

Example 23

[(4-Hydroxy-8-methyl-2-oxo-2H-thiochromene-3-carbonyl)-amino]-acetic acid a) [(4-Hydroxy-8-methyl-2-oxo-2H-thiochromene-3-carbonyl)-amino]-acetic acid

[(6-Chloro-4-hydroxy-8-methyl-2-oxo-2H-thio-chromene-3-carbonyl)-amino]-acetic acid (95 mg, 0.29 mmol) was dissolved in 1N sodium hydroxide (1.16 mL) and water (1.84 mL). 10% Palladium on carbon (9.5 mg) was added and the solution was vacuum purged and treated with hydrogen gas (1 atm). The reaction stirred overnight (18 h) at ambient temperature and the crude mixture was filtered through Celite® and the filter cake was washed with 1N sodium hydroxide. The aqueous phase was acidified to pH 3 with 1N hydrochloric acid and the product was collected by filtration to give [(4-hydroxy-8-methyl-2-oxo-2H-thio-chromene-3-carbonyl)-amino]-acetic acid (75 mg, 88%). MS ESI(+) m/e: 392.22 (M−1).

Example 24

[(1-Hydroxy-3-oxo-3H-4-thia-phenanthrene-2-carbonyl)-amino]-acetic acid a) Dimethyl-thiocarbamic acid O-(2-acetyl-naphthalen-1-yl) ester

Dimethyl-thiocarbamic acid O-(2-acetyl-naphthalen-1-yl) ester was prepared under conditions analogous to Example 21(a) using 1-(1-Hydroxy-naphthalen-2-yl)-ethanone. $^1$H NMR (200 MHz, CDCl$_3$): 7.90-7.80 (4H, m), 7.59-7.53 (2H, m), 3.58 (3H, s), 3.54 (3H, s), 2.66 (3H, s).

b) Dimethyl-thiocarbamic acid S-(2-acetyl-naphthalen-1-yl) ester

Dimethyl-thiocarbamic acid S-(2-acetyl-naphthalen-1-yl) ester was prepared under conditions analogous to Example 21(b). $^1$H NMR (200 MHz, CDCl$_3$): 8.43 (1H, d), 8.0-7.82 (2H, m), 7.63-7.45 (3H, m), 3.25 (3H, br s), 3.02 (3H, br s), 2.65 (3H, s).

c) 1-Hydroxy-4-thia-phenanthren-3-one

1-Hydroxy-4-thia-phenanthren-3-one was prepared under conditions analogous to Example 21(c). $^1$H NMR (200 MHz, CDCl$_3$): 8.17 (1H, d), 8.08-7.95 (2H, m), 7.77-7.69 (3H, m), 6.18 (1H, s).

d) [(1-Hydroxy-3-oxo-3H-4-thia-phenanthrene-2-carbonyl)-amino]-acetic acid ethyl ester

[(1-Hydroxy-3-oxo-3H-4-thia-phenanthrene-2-carbonyl)-amino]-acetic acid ethyl ester was prepared under conditions analogous to Example 21(d). $^1$H NMR (200 MHz, CDCl$_3$): 10.18 (1H, br t), 8.21 (1H, d), 8.05 (1H, d), 7.85-7.53 (4H, m), 4.28 (2H, q), 4.21 (2H, d), 1.34 (3H, t).

e) [(1-Hydroxy-3-oxo-3H-4-thia-phenanthrene-2-carbonyl)-amino]-acetic acid

[(1-Hydroxy-3-oxo-3H-4-thia-phenanthrene-2-carbonyl)-amino]-acetic acid was prepared under conditions analogous to Example 21(e). MS ESI(−) m/e: 328.132 (M−1).

Example 25

[(1-Hydroxy-3-oxo-3H-benzo[f]thiochromene-2-carbonyl)-amino]acetic acid a) Dimethyl-thiocarbamic acid O-(1-acetyl-naphthalen-2-yl)ester

Dimethyl-thiocarbamic acid O-(1-acetyl-naphthalen-2-yl) ester was prepared under conditions analogous to Example 21(a) using 1-(2-hydroxy-naphthalen-1-yl)-ethanone. $^1$H NMR (200 MHz, CDCl$_3$): 7.89-7.75 (3H, m), 7.54-7.48 (2H, m), 7.26 (1H, d), 3.48 (3H, s), 3.37 (3H, s), 2.66 (3H, s).

b) Dimethyl-thiocarbamic acid S-(1-acetyl-naphthalen-2-yl) ester

Dimethyl-thiocarbamic acid S-(1-acetyl-naphthalen-2-yl) ester was prepared under conditions analogous to Example 21(b). $^1$H NMR (200 MHz, CDCl$_3$): 7.70-7.49 (4H, m), 3.15 (3H, br s), 3.06 (3H, br s), 2.65 (3H, s).

c) 1-Hydroxy-benzo[f]thiochromen-3-one

1-Hydroxy-benzo[f]thiochromen-3-one was prepared under conditions analogous to Example 21(c). MS ESI(−) m/e: 227.297 (M−1).

d) [(1-Hydroxy-3-oxo-3H-benzo[f]thiochromene-2-carbonyl)-amino]-acetic acid ethyl ester

[(1-Hydroxy-3-oxo-3H-benzo[f]thiochromene-2-carbonyl)-amino]-acetic acid ethyl ester prepared under conditions analogous to Example 21(d). MS ESI(−) m/e: 356.534 (M−1).

e) [(1-Hydroxy-3-oxo-3H-benzo[f]thiochromene-2-carbonyl)-amino]-acetic acid

[(1-Hydroxy-3-oxo-3H-benzo[f]thiochromene-2-carbonyl)-amino]-acetic acid was prepared under conditions analogous to Example 21(e). MS ESI(−) m/e: 328.069 (M−1).

Example 26

[(7-Butoxy-4-hydroxy-2-oxo-2H-thiochromene-3-carbonyl)-amino]-acetic acid a) 3,3-Di-(n-butoxy)diphenyl disulfide 3,3-Dihydroxydiphenyl disulfide (5.0 g, 20 mmol) was dissolved in anhydrous N,N-dimethylformamide (30 mL). Cesium carbonate (13 g, 40 mmol) and n-butyl iodide (4.55 mL, 40 mmol) were added sequentially and the reaction was allowed to stir at ambient temperature for 36 h. The reaction was quenched by pouring the solution onto a mixture of ice and 1N HCl. The resulting oily residue was extracted into methylene chloride, dried over sodium sulfate. The crude product was purified by silica gel chromatography (1%-7% ethyl acetate in hexanes) to provide 3,3-di-(n-butoxy)diphenyl disulfide (6.9 g, 95%). $^1$H NMR (200 MHz, CDCl$_3$): 7.17 (1H, t), 7.04 (2H, m), 6.72 (1H, m), 3.90 (2H, t), 1.73 (2H, m), 1.54 (2H, m), 0.95 (3H, t).

b) 3-Butoxy-benzenethiol 3,3-Di-(n-butoxy)diphenyl disulfide (2.0 g, 5.52 mmol) was dissolved in a mixture of tetrahydrofuran (15 mL) and methanol (3 mL). To this solution was added 10% sulfuric acid (10 mL) and zinc powder (725 mg, 11 mmol) and the reaction was permitted to stir at ambient temperature for 8 h. The reaction was concentrated in vacuo and the residue extracted with methylene chloride. The organic layer was dried over sodium sulfate and concentrated to give 3-butoxy-benzenethiol (2.0 g, 100%) which was used directly without further purification. $^1$H NMR (200 MHz, CDCl$_3$): 7.107 (1H, t), 6.79 (2H, m), 6.65 (1H, m), 3.92 (2H, t), 3.43 (1H, s), 1.74 (2H, m), 1.53 (2H, m), 0.97 (3H, t).

c) 7-Butoxy-4-hydroxy-2-oxo-2H-thiochromene-3-carboxylic acid ethyl ester

3-Butoxy-benzenethiol (1.2 g, 6.58 mmol) was dissolved in 2-ethoxycarbonyl-malonic acid diethyl ester (2.1 mL, 9.87 mmol). Tin tetrachloride (26 µL, 0.224 mmol) was added and the reaction was sealed and heated to 210° C. After 2 h, the reaction was cooled and directly subjected to silica gel chromatography (5%-50% ethyl acetate in hexanes) to provide 7-butoxy-4-hydroxy-2-oxo-2H-thiochromene-3-carboxylic acid ethyl ester (140 mg, 7%). MS ESI(−) m/e: 321.249 (M−1).

d) [(7-Butoxy-4-hydroxy-2-oxo-2H-thiochromene-3-carbonyl)-amino]-acetic acid A mixture of 7-butoxy-4-hydroxy-2-oxo-2H-thiochromene-3-carboxylic acid ethyl ester (140 mg, 0.434 mmol) and sodium glycinate (420 mg, 4.34 mmol) in 2-methoxyethanol (10 mL) was refluxed overnight (16 h). Reaction mixture was concentrated, and crude residue was dissolved in water, acidified to pH 3 using 1 N HCl to precipitate the product. The precipitate was collected by filtration and dried to provide [(7-butoxy-4-hydroxy-2-oxo-2H-thiochromene-3-carbonyl)-amino]-acetic acid (120 mg, 80%). MS ESI(−) m/e: 350.21 (M−1).

Example 27

[(6-Bromo-4-hydroxy-2-oxo-2H-thiochromene-3-carbonyl)-amino]-acetic acid a) 5-Bromo-2-dimethylthiocarbamoyloxy-benzoic acid methyl ester

To a mixture of 5-Bromo-2-hydroxy-benzoic acid methyl ester (29.8 g, 129 mmol) and dimethylthiocarbamoyl chloride (17.54 g, 142 mmol) in DMF at room temperature was added DABCO (21.7 g, 193.5 mmol). The resulting mixture, after being stirred at room temperature overnight, was diluted with water (1.25 L) and acidified to a pH~4 using 1 N HCl. The precipitate was collected, rinsed with water and dried in vacuo to provide crude 5-bromo-2-dimethylthiocarbamoyloxy-benzoic acid methyl ester as an off-white solid in 91% yield. The product was used directly in the subsequent reaction without purification.

b) 5-Bromo-2-dimethylcarbamoylsulfanyl-benzoic acid methyl ester

Solid 5-bromo-2-dimethylthiocarbamoyloxy-benzoic acid methyl ester (10 g, 31.4 mmol) was suspended in bromobenzene (60 mL) heated to 195° C. overnight in a sealed vessel. The reaction was cooled, concentrated in vacuo, and purified by silica gel chromatography (eluting with 10-20% EtOAc in hexanes) to provide 5-bromo-2-dimethylcarbamoylsulfanylbenzoic acid methyl ester in 69% yield. $^1$H NMR (200 MHz, CDCl$_3$): δ ppm=8.00 (s, 1H), 7.6 (d, 1H), 7.56 (d, 1H), 3.88 (3, 3H), 3.096 (br s, 3H), 3.027 (br s, 3H).

c) 5-Bromo-2-dimethylcarbamoylsulfanyl-benzoic acid

A mixture of 5-bromo-2-dimethylcarbamoylsulfanyl-benzoic acid methyl ester (10.0 g, 31.42 mmol) and lithium hydroxide hydrate (1.98 g, 47.14 mmol) in (1/1/1) THF/MeOH/H$_2$O (70 mL total volume) was stirred at room temperature for 4 h. The reaction mixture was concentrated to remove most organic solvents. The residue was diluted with water (500 mL) and extracted with EtOAc (100 mL), which is discarded. The aqueous layer was acidified to pH 3-4 using 1 N HCl and extracted with EtOAc (2×400 mL). The combined organic layers were washed with brine, dried over MgSO$_4$, filtered and concentrated to provide crude 5-bromo-2-dimethylcarbamoylsulfanyl-benzoic acid which was used directly and without further purification.

d) 2-(5-Bromo-2-dimethylcarbamoylsulfanyl-benzoyl)-malonic acid dimethyl ester To a mixture of crude 5-bromo-2-dimethylcarbamoylsulfanyl-benzoic acid (5.4 g, 17.75 mmol) in THF (80 mL) at 0° C. was added DCC (3.66 g, 17.75 mmol), followed by HOBT (2.4 g, 17.75 mmol). The reaction mixture was stirred at 0° C. for 3 h and filtered to give Solution 1. In another flask, NaH (60% dispersed in mineral oil) (1.06 g, 26.62 mmol) was added to cold THF (170 mL, 0° C.) and added slowly dimethyl malonate (2.46 g, 18.63 mmol). The reaction mixture was stirred at 0° C. for 15 min until gas evolution ceased. To this mixture was added Solution 1. The resulting mixture was stirred at 0° C. for 5 min, then at room temperature for 2 h and concentrated. The residue was treated with water (400 mL) and acidified to pH 4-5 using 1 N HCl, extracted with EtOAc (2×200 mL) and the combined organic layers washed with brine, dried over MgSO$_4$, filtered and concentrated. The crude residue was purified by silica gel chromatography (1%-10% EtOAc in CH$_2$Cl$_2$) to provide 2-(5-bromo-2-dimethylcarbamoylsulfanyl-benzoyl)-malonic acid dimethyl ester (4.9 g) which was used directly, without further purification.

e) 6-Bromo-4-hydroxy-2-oxo-2H-thiochromene-3-carboxylic acid methyl ester

A mixture of 2-(5-bromo-2-dimethylcarbamoylsulfanyl-benzoyl)-malonic acid dimethyl ester (4.9 g, 11.71 mmol) in 0.5 M NaOMe/MeOH solution (94 mL) was heated to reflux for 6 h. After cooling overnight, the precipitated solid was collected by filtration and rinsed with MeOH followed by ether. The solid was dried in vacuo to provide 6-bromo-4-hydroxy-2-oxo-2H-thiochromene-3-carboxylic acid methyl ester (1.9 g) as a sodium salt. $^1$HNMR (200 MHz, DMSO-d$_6$): δ (ppm)=8.164 (s, 1H), 7.524 (d, 1H), 7.23 (d, 1H), 3.56 (s, 3H).

f) [(6-Bromo-4-hydroxy-2-oxo-2H-thiochromene-3-carbonyl)-amino]-acetic acid

[(6-Bromo-4-hydroxy-2-oxo-2H-thiochromene-3-carbonyl)-amino]-acetic acid was prepared under conditions analogous to Example 3(d). MS ESI(−) m/e: 355.8188, 357.8660 (M−1).

Example 28

2-(S)-[(6-Bromo-4-hydroxy-2-oxo-2H-thiochromene-3-carbonyl)-amino]-propionic acid 2-[(6-Bromo-4-hydroxy-2-oxo-2H-thiochromene-3-carbonyl)-amino]-propionic acid was prepared under conditions analogous to Example 3(d) using L-alanine. MS ESI(−) m/e: 369.86, 371.9 (M−1).

Example 29

{[7-(3,5-Bis-trifluoromethyl-phenyl)-4-hydroxy-2-oxo-2H-thiochromene-3-carbonyl]-amino}-acetic acid a) 7-(3,5-Bis-trifluoromethyl-phenyl)-4-hydroxy-2-oxo-2H-thiochromene-3-carboxylic acid methyl ester 7-(3,5-Bis-trifluoromethyl-phenyl)-4-hydroxy-2-oxo-2H-thiochromene-3-carboxylic acid methyl ester was prepared from 7-bromo-4-hydroxy-2-oxo-2H-thiochromene-3-carboxylic acid methyl ester under conditions analogous to Example 7(a) using 3,5-Bis-trifluoromethyl-phenylboronic acid. $^1$H NMR (200 MHz, CDCl$_3$): δ (ppm)=8.47 (d, 1H), 8.03 (s, 2H), 7.937 (s, 1H), 7.66-7.56 (m, 2H), 4.03 (s, 3H).

b) {[7-(3,5-Bis-trifluoromethyl-phenyl)-4-hydroxy-2-oxo-2H-thiochromene-3-carbonyl]-amino}-acetic acid {[7-(3,5-Bis-trifluoromethyl-phenyl)-4-hydroxy-2-oxo-2H-thiochromene-3-carbonyl]-amino}-acetic was prepared under conditions analogous to Example 3(d) using glycine. MS ESI(−) m/e: 489.9126 (M−1).

Example 30

{[7-(3-Fluoro-phenyl)-4-hydroxy-2-oxo-2H-thiochromene-3-carbonyl]-amino}-acetic acid a) 7-(3-Fluoro-phenyl)-4-hydroxy-2-oxo-2H-thiochromene-3-carboxylic acid methyl ester 7-(3-Fluoro-phenyl)-4-hydroxy-2-oxo-2H-thiochromene-3-carboxylic acid methyl ester was prepared from 7-bromo-4-hydroxy-2-oxo-2H-thiochromene-3-carboxylic acid methyl ester under conditions analogous to Example 7(a) using 3-fluoro-phenylboronic acid. $^1$H NMR (200 MHz, CDCl$_3$): δ (ppm)=8.41 (d, 1H), 7.625-7.114 (m, 6H), 4.02 (s, 3H).

b) {[7-(3-Fluoro-phenyl)-4-hydroxy-2-oxo-2H-thiochromene-3-carbonyl]-amino}-acetic acid 7-(3-Fluoro-phenyl)-4-hydroxy-2-oxo-2H-thiochromene-3-carbonyl]-amino}-acetic acid was prepared under conditions analogous to Example 3(d) using glycine. MS ESI(−) m/e: 371.922 (M−1).

Example 31

2-(S)-{[7-(3-Fluoro-phenyl)-4-hydroxy-2-oxo-2H-thiochromene-3-carbonyl]-amino}-propionic acid 2-{[7-(3-Fluoro-phenyl)-4-hydroxy-2-oxo-2H-thiochromene-3-carbonyl]-amino}-propionic acid was prepared under conditions analogous to Example 3(d) using L-alanine. MS ESI(+) m/e: 388.0266 (M+1).

Example 32

{[4-Hydroxy-2-oxo-7-(2-trifluoromethyl-phenyl)-2H-thiochromene-3-carbonyl]-amino}-acetic acid a) 4-Hydroxy-2-oxo-7-(2-trifluoromethyl-phenyl)-2H-thiochromene-3-carboxylic acid methyl ester 4-Hydroxy-2-oxo-7-(2-trifluoromethyl-phenyl)-2H-thiochromene-3-carboxylic acid methyl ester was prepared from 7-bromo-4-hydroxy-2-oxo-2H-thiochromene-3-carboxylic acid methyl ester (Example 5e) under conditions analogous to Example 7(a) using 2-trifluoromethyl-phenylboronic acid. $^1$H NMR (200 MHz, CDCl$_3$): δ (ppm)=8.376 (d, 1H), 7.783-7.295 (m, 6H), 4.024 (s, 3H).

b) {[4-Hydroxy-2-oxo-7-(2-trifluoromethyl-phenyl)-2H-thiochromene-3-carbonyl]-amino}-acetic acid {[4-Hydroxy-2-oxo-7-(2-trifluoromethyl-phenyl)-2H-thiochromene-3-carbonyl]-amino}-acetic acid was prepared under conditions analogous to Example 3(d) using glycine. MS ESI(−) m/e: 421.930 (M−1).

Example 33

{[6-(3,5-Bis-trifluoromethyl-phenyl)-4-hydroxy-2-oxo-2H-thiochromene-3-carbonyl]-amino}-acetic acid a) 6-(3,5-Bis-trifluoromethyl-phenyl)-4-hydroxy-2-oxo-2H-thiochromene-3-carboxylic acid methyl ester 6-(3,5-Bis-trifluoromethyl-phenyl)-4-hydroxy-2-oxo-2H-thiochromene-3-carboxylic acid methyl ester was prepared from 6-bromo-4-hydroxy-2-oxo-2H-thiochromene-3-carboxylic acid methyl ester (Example 27e) under conditions analogous to Example 7(a) using 3,5-Bis-trifluoromethyl-phenylboronic acid. $^1$H NMR (200 MHz, CDCl$_3$): δ (ppm)=8.572 (s, 1H), 8.037 (s, 2H), 7.908 (s, 1H), 7.820 (d, 1H), 7.510 (d, 1H), 4.04 (s, 3H).

b) {[6-(3,5-Bis-trifluoromethyl-phenyl)-4-hydroxy-2-oxo-2H-thiochromene-3-carbonyl]-amino}-acetic acid {[6-(3,5-Bis-trifluoromethyl-phenyl)-4-hydroxy-2-oxo-2H-thiochromene-3-carbonyl]-amino}-acetic acid was prepared under conditions analogous to Example 3(d) using glycine. MS ESI(−) m/e: 489.8597 (M−1).

Example 34

{[4-Hydroxy-2-oxo-6-(2-trifluoromethyl-phenyl)-2H-thiochromene-3-carbonyl]-amino}-acetic acid a) 4-Hydroxy-2-oxo-6-(2-trifluoromethyl-phenyl)-2H-thiochromene-3-carboxylic acid methyl ester 4-Hydroxy-2-oxo-6-(2-trifluoromethyl-phenyl)-2H-thiochromene-3-carboxylic acid methyl ester was prepared from 6-bromo-4-hydroxy-2-oxo-2H-thiochromene-3-carboxylic acid methyl ester under conditions analogous to Example 7(a) using 2-trifluoromethyl-phenylboronic acid. $^1$H NMR (200 MHz, CDCl$_3$): δ (ppm)=8.572 (s, 1H), 7.838-7.676 (m, 4H), 7.487-7.354 (m, 2H), 4.028 (s, 3H).

b) {[4-Hydroxy-2-oxo-6-(2-trifluoromethyl-phenyl)-2H-thiochromene-3-carbonyl]-amino}-acetic acid {[4-Hydroxy-2-oxo-6-(2-trifluoromethyl-phenyl)-2H-thiochromene-3-carbonyl]-amino}-acetic acid was prepared under conditions analogous to Example 3(d) using glycine. MS ESI(−) m/e: 421.9431 (M−1).

Example 35

{[4-Hydroxy-6-(4-methoxy-phenyl)-2-oxo-2H-thiochromene-3-carbonyl]-amino}-acetic acid a) 4-Hydroxy-6-(4-methoxy-phenyl)-2-oxo-2H-thiochromene-3-carboxylic acid methyl ester 4-Hydroxy-6-(4-methoxy-phenyl)-2-oxo-2H-thiochromene-3-carboxylic acid methyl ester was prepared from 6-bromo-4-hydroxy-2-oxo-2H-thiochromene-3-carboxylic acid methyl ester under conditions analogous to Example 7(a) using 4-methoxy-phenylboronic acid. $^1$H NMR (200 MHz, CDCl$_3$): δ (ppm)=8.521 (s, 1H), 7.803-7.352 (m, 5H), 7.001 (s, 1H), 4.022 (s, 3H), 3.864 (s, 3H).

b) {[4-Hydroxy-6-(4-methoxy-phenyl)-2-oxo-2H-thiochromene-3-carbonyl]-amino}-acetic acid {[4-Hydroxy-6-(4-methoxy-phenyl)-2-oxo-2H-thiochromene-3-carbonyl]-amino}-acetic acid was prepared under conditions analogous to Example 3(d) using glycine. MS ESI(−) m/e: 383.9676 (M−1).

Example 36

{[6-(2-Chloro-phenyl)-4-hydroxy-2-oxo-2H-thiochromene-3-carbonyl]-amino}-acetic acid a) 6-(2-Chloro-phenyl)-4-hydroxy-2-oxo-2H-thiochromene-3-carboxylic acid methyl ester 6-(2-Chloro-phenyl)-4-hydroxy-2-oxo-2H-thiochromene-3-carboxylic acid methyl ester was prepared from 6-bromo-4-hydroxy-2-oxo-2H-thiochromene-3-carboxylic acid methyl ester under conditions analogous to Example 7(a) using 2-chloro-phenylboronic acid. $^1$H NMR (200 MHz, CDCl$_3$): δ (ppm)=8.412 (s, 1H), 7.697 (d, 1H), 7.490-7.305 (m, 5H), 4.018 (s, 3H).

b) {[6-(2-Chloro-phenyl)-4-hydroxy-2-oxo-2H-thiochromene-3-carbonyl]-amino}-acetic acid {[6-(2-Chloro-phenyl)-4-hydroxy-2-oxo-2H-thiochromene-3-carbonyl]-amino}-acetic acid was prepared under conditions analogous to Example 3(d) using glycine. MS ESI(−) m/e: 387.9629, 389.8753 (M−1).

Example 37

{[6-(3-Fluoro-phenyl)-4-hydroxy-2-oxo-2H-thiochromene-3-carbonyl]-amino}-acetic acid a) 6-(3-Fluoro-phenyl)-4-hydroxy-2-oxo-2H-thiochromene-3-carboxylic acid methyl ester 6-(3-Fluoro-phenyl)-4-hydroxy-2-oxo-2H-thiochromene-3-carboxylic acid methyl ester was prepared from 6-bromo- 4-hydroxy-2-oxo-2H-thiochromene-3-carboxylic acid methyl ester under conditions analogous to Example 7(a) using 3-fluoro-phenylboronic acid. $^1$H NMR (200 MHz, CDCl$_3$): δ (ppm)=8.549 (s, 1H), 7.814-7.664 (m, 2H), 7.463-7.249 (m, 3H), 7.132-7.042 (m, 1H), 4.028 (s, 3H).

b) {[6-(3-Fluoro-phenyl)-4-hydroxy-2-oxo-2H-thiochromene-3-carbonyl]-amino}-acetic acid {[6-(3-Fluoro-phenyl)-4-hydroxy-2-oxo-2H-thiochromene-3-carbonyl]-amino}-acetic acid was prepared under conditions analogous to Example 3(d) using glycine. MS ESI(−) m/e: 371.9625 (M−1).

Example 38

{[6-(4-Fluoro-phenyl)-4-hydroxy-2-oxo-2H-thiochromene-3-carbonyl]-amino}-acetic acid a) 6-(4-Fluoro-phenyl)-4-hydroxy-2-oxo-2H-thiochromene-3-carboxylic acid methyl ester 6-(4-Fluoro-phenyl)-4-hydroxy-2-oxo-2H-thiochromene-3-carboxylic acid methyl ester was prepared from 6-bromo-4-hydroxy-2-oxo-2H-thiochromene-3-carboxylic acid methyl ester under conditions analogous to Example 7(a) using 4-fluoro-phenylboronic acid. $^1$H NMR (200 MHz, CDCl$_3$): δ (ppm)=8.515 (s, 1H), 7.765 (d, 1H), 7.586 (m, 2H), 7.427 (d, 1H), 7.381-7.120 (m, 2H), 4.026 (s, 3H).

b) {[6-(4-Fluoro-phenyl)-4-hydroxy-2-oxo-2H-thiochromene-3-carbonyl]-amino}-acetic acid {[6-(4-Fluoro-phenyl)-4-hydroxy-2-oxo-2H-thiochromene-3-carbonyl]-amino}-acetic acid was prepared under conditions analogous to Example 3(d) using glycine. MS ESI(−) m/e: 371.9871 (M−1).

Example 39

{[4-Hydroxy-6-(2-methoxy-phenyl)-2-oxo-2H-thiochromene-3-carbonyl]-amino}-acetic acid a) 4-Hydroxy-6-(2-methoxy-phenyl)-2-oxo-2H-thiochromene-3-carboxylic acid methyl ester 4-Hydroxy-6-(2-methoxy-phenyl)-2-oxo-2H-thiochromene-3-carboxylic acid methyl ester was prepared from 6-bromo-4-hydroxy-2-oxo-2H-thiochromene-3-carboxylic acid methyl ester under conditions analogous to Example 7(a) using 2-methoxy-phenylboronic acid. $^1$H NMR (200 MHz, CDCl$_3$): δ (ppm)=8.481 (s, 1H), 7.803 (d, 1H), 7.627-7.789 (m, 1H), 7.42-6.92 (m, 4H), 4.022 (s, 3H), 3.82 (s, 3H).

b) {[4-Hydroxy-6-(2-methoxy-phenyl)-2-oxo-2H-thiochromene-3-carbonyl]-amino}-acetic acid {[4-Hydroxy-6-(2-methoxy-phenyl)-2-oxo-2H-thiochromene-3-carbonyl]-amino}-acetic acid was prepared under conditions analogous to Example 3(d) using glycine. MS ESI(−) m/e: 383.9901 (M−1).

Example 40

{[4-Hydroxy-2-oxo-6-(4-trifluoromethoxy-phenyl)-2H-thiochromene-3-carbonyl]-amino}-acetic acid a) 4-Hydroxy-6-(2-methoxy-phenyl)-2-oxo-2H-thiochromene-3-carboxylic acid methyl ester 4-Hydroxy-6-(2-methoxy-phenyl)-2-oxo-2H-thiochromene-3-carboxylic acid methyl ester was prepared from 6-bromo-4-hydroxy-2-oxo-2H-thiochromene-3-carboxylic acid methyl ester under conditions analogous to Example 7(a) using 4-trifluoromethoxy-phenylboronic acid. $^1$H NMR (200 MHz, CDCl$_3$): δ (ppm)=8.534 (s, 1H), 7.782 (d, 1H), 7.639 (d, 2H), 7.444 (d, 1H), 7.320 (d, 2H), 4.026 (s, 3H).

b) {[4-Hydroxy-2-oxo-6-(4-trifluoromethoxy-phenyl)-2H-thiochromene-3-carbonyl]-amino}-acetic acid {[4-Hydroxy-2-oxo-6-(4-trifluoromethoxy-phenyl)-2H-thiochromene-3-carbonyl]-amino}-acetic acid was prepared under conditions analogous to Example 3(d) using glycine. MS ESI(−) m/e: 437.9177 (M−1).

Example 41

[(6-Benzoylamino-4-hydroxy-2-oxo-2H-thiochromene-3-carbonyl)-amino]-acetic acid a) 6-Benzoylamino-4-hydroxy-2-oxo-2H-thiochromene-3-carboxylic acid methyl ester 6-bromo-4-hydroxy-2-oxo-2H-thiochromene-3-carboxylic acid methyl (100 mg, 0.317 mmol), benzamide (46 mg, 0.381 mmol), Tris(dibenzylideneacetone)dipalladium (0) (9 mg, 0.016 mmol), 9,9-Dimethyl-4,5-bis(diphenylphosphino) xanthene (18 mg, 0.032 mmol), and cesium carbonate (206 mg, 0.634 mmol) were added together in an oven-dried flask equipped with a stir bar. Anhydrous 1,4-dioxane (3 mL) was added via syringe and the reaction was brought to reflux. After refluxing overnight, the reaction was cooled to ambient temperature and partitioned between ethyl acetate (15 mL) and brine (15 mL.) The biphasic mixture was vacuum-filtered and the isolated solid dried overnight to provide the title compound (140 mg.) MS ESI(−) m/e: 353.9770 (M−1).

b) [(6-Benzoylamino-4-hydroxy-2-oxo-2H-thiochromene-3-carbonyl)-amino]-acetic acid

[(6-Benzoylamino-4-hydroxy-2-oxo-2H-thiochromene-3-carbonyl)-amino]-acetic acid was prepared under conditions analogous to Example 3(d) using glycine. MS ESI(−) m/e: 396.9744 (M−1).

Example 42

[(8-Benzyl-6-chloro-4-hydroxy-2-oxo-2H-thiochromene-3-carbonyl)-amino]-acetic acid

[(8-Bromo-6-chloro-4-hydroxy-2-oxo-2H-thiochromene-3-carbonyl)-amino]-acetic acid ethyl ester (22(d)) (500 mg, 1.2 mmol) was dissolved in THF-water (4:1; 20 mL total volume). To the solution was added potassium benzyltrifluoroborate (285 mg, 1.2 mmol), cesium carbonate (1.2 g, 3.6 mmol), and bis(triphenylphosphino) palladium(II) dichloride (168 mg, 0.24 mmol). The mixture was heated to reflux for six hours, cooled and concentrated. The residue was triturated with hot methanol (20 mL) and filtered to provide the title compound (395 mg.) MS ESI(−) m/e: 402.355, 403.783 (M−1).

Example 43

{[8-(3,5-Bis-trifluoromethyl-phenyl)-6-chloro-4-hydroxy-2-oxo-2H-thiochromene-3-carbonyl]-amino}-acetic acid

[(8-Bromo-6-chloro-4-hydroxy-2-oxo-2H-thiochromene-3-carbonyl)-amino]-acetic acid ethyl ester (22(d)) (500 mg, 1.2 mmol) was dissolved in DME-aqueous sodium carbonate (2M) (7 mL: 1.5 mL). To the solution was added 3,5-bis-trifluoromethyl-phenyl boronic acid (372 mg, 1.44 mmol) and tetrakis(triphenylphosphino) palladium(0) (275 mg, 0.24 mmol). The mixture was heated to reflux for six hours, cooled and concentrated. The residue was triturated with hot methanol (20 mL) and filtered to provide the title compound (470 mg.) MS ESI(−) m/e: 524.114, 526.018 (M−1).

Example 44

[(6-Chloro-4-hydroxy-2-oxo-8-phenyl-2H-thio-chromene-3-carbonyl)-amino]-acetic acid a) [(6-Chloro-4-hydroxy-2-oxo-8-phenyl-2H-thio-chromene-3-carbonyl)-amino]-acetic acid ethyl ester

[(8-Bromo-6-chloro-4-hydroxy-2-oxo-2H-thiochromene-3-carbonyl)-amino]-acetic acid ethyl ester (22(d)) (500 mg, 1.2 mmol) was dissolved in anhydrous DMF (5 mL). To the solution was added Tributyl-phenyl-stannane (467 uL, 1.43 mmol), bis(triphenylphosphino) palladium(II) dichloride (100 mg, 0.12 mmol) and 4 A molecular sieves. The reaction was sealed and the solution was heated to 120 C for 45 minutes. The reaction was cooled, diluted with ethyl acetate (25 mL) and water (25 mL). The organic phase was separated, dried over magnesium sulfate and concentrated residue in vacuo. The residue was filtered through silica to provide the title compound (418 mg) which was used directly without further purification.

b) [(6-Chloro-4-hydroxy-2-oxo-8-phenyl-2H-thio-chromene-3-carbonyl)-amino]-acetic acid

[(6-Chloro-4-hydroxy-2-oxo-8-phenyl-2H-thio-chromene-3-carbonyl)-amino]-acetic acid ethyl ester (200 mg, 0.479 mmol) was dissolved in THF-Methanol (1:1; 13 mL total volume.) Sodium hydroxide (1.5 mmol, 1.5 mL; 1M) was added and the solution stirred overnight at ambient temperature. The reaction mixture was concentrated in vacuo and the residue was dissolved in water (10 mL.) The crude product was precipitated with 1N HCl (3 mL) and isolated via filtration and triturated with hexanes to provide the title compound (177 mg.) MS ESI(+) m/e: 390.118, 392.226 (M+1).

Example 45

{[6-Chloro-4-hydroxy-8-(2-methyl-5-trifluorom-ethyl-2H-pyrazol-3-yl)-2-oxo-2H-thiochromene-3-carbonyl]-amino}-acetic acid a) {[6-Chloro-4-hydroxy-8-(2-methyl-5-trifluorom-ethyl-2H-pyrazol-3-yl)-2-oxo-2H-thiochromene-3-carbonyl]-amino}-acetic acid ethyl ester {[6-Chloro-4-hydroxy-8-(2-methyl-5-trifluoromethyl-2H-pyrazol-3-yl)-2-oxo-2H-thiochromene-3-carbonyl]-amino}-acetic acid ethyl ester was prepared under conditions analogous to Example 44(a) using 1-Methyl-5-tributylstan-nanyl-3-trifluoromethyl-1H-pyrazole. MS ESI(−) m/e: 488.151, 490.171 (M−1).

b) [(6-Chloro-4-hydroxy-2-oxo-8-phenyl-2H-thio-chromene-3-carbonyl)-amino]-acetic acid {[6-Chloro-4-hydroxy-8-(2-methyl-5-trifluoromethyl-2H-pyrazol-3-yl)-2-oxo-2H-thiochromene-3-carbonyl]-amino}-acetic acid was prepared under conditions analogous to Example 44(b.) MS ESI(−) m/e: 460.278, 462.113 (M−1).

Example 46

[(6-Chloro-4-hydroxy-2-oxo-8-pyridin-3-yl-2H-thio-chromene-3-carbonyl)-amino]-acetic acid a) [(6-Chloro-4-hydroxy-2-oxo-8-pyridin-3-yl-2H-thiochromene-3-carbonyl)-amino]-acetic acid ethyl ester

[(6-Chloro-4-hydroxy-2-oxo-8-pyridin-3-yl-2H-thio-chromene-3-carbonyl)-amino]-acetic acid ethyl ester was prepared under conditions analogous to Example 44(a) using 3-Tributylstannanyl-pyridine.

b) [(6-Chloro-4-hydroxy-2-oxo-8-pyridin-3-yl-2H-thiochromene-3-carbonyl)-amino]-acetic acid

[(6-Chloro-4-hydroxy-2-oxo-8-pyridin-3-yl-2H-thio-chromene-3-carbonyl)-amino]-acetic acid was prepared under conditions analogous to Example 44(b.) MS ESI(−) m/e: 389.167, 391.342 (M−1).

Example 47

[(8-Benzyl-4-hydroxy-2-oxo-2H-thiochromene-3-carbonyl)-amino]-acetic acid

[(6-Chloro-4-hydroxy-2-oxo-8-benzyl-2H-thiochromene-3-carbonyl)-amino]-acetic acid (Example 42a) (70 mg, 0.173 mmol) was dissolved in aqueous sodium hydroxide (870 uL 1M in 8 mL of water) and 10% palladium on carbon (7 mg) was added. The reaction was vacuum-purged and placed under an atmosphere of hydrogen gas and permitted to stir overnight at ambient temperature. Upon completion, the reaction was filtered through a pad of Celite® to remove the palladium catalyst. The product was precipitated with 1N HCl, isolated via filtration and dried to provide the title compound (30 mg.) MS ESI(−) m/e: 368.093 (M−1).

Example 48

{[8-(3,5-Bis-trifluoromethyl-phenyl)-4-hydroxy-2-oxo-2H-thiochromene-3-carbonyl]-amino}-acetic acid {[8-(3,5-Bis-trifluoromethyl-phenyl)-4-hydroxy-2-oxo-2H-thiochromene-3-carbonyl]-amino}-acetic acid was prepared under conditions analogous to Example 47(a.) MS ESI(−) m/e: 490.013 (M−1).

Example 49

{[4-Hydroxy-8-(2-methyl-5-trifluoromethyl-2H-pyrazol-3-yl)-2-oxo-2H-thiochromene-3-carbonyl]-amino}-acetic acid {[4-Hydroxy-8-(2-methyl-5-trifluoromethyl-2H-pyrazol-3-yl)-2-oxo-2H-thiochromene-3-carbonyl]-amino}-acetic acid was prepared under conditions analogous to Example 47(a.) MS ESI(−) m/e: 426.025 (M−1).

Example 50

[(4-Hydroxy-2-oxo-8-pyridin-3-yl-2H-thiochromene-3-carbonyl)-amino]-acetic acid

[(4-Hydroxy-2-oxo-8-pyridin-3-yl-2H-thiochromene-3-carbonyl)-amino]-acetic acid was prepared under conditions analogous to Example 47(a.) MS ESI(+) m/e: 357.003 (M+1).

Example 51

[(4-Hydroxy-2-oxo-8-phenyl-2H-thiochromene-3-carbonyl)-amino]-acetic acid

[(4-Hydroxy-2-oxo-8-phenyl-2H-thiochromene-3-carbonyl)-amino]-acetic acid was prepared under conditions analogous to Example 47(a.) MS ESI(+) m/e: 356.0427 (M+1).

Example 52

[(5-Fluoro-4-hydroxy-2-oxo-2H-thiochromene-3-carbonyl)-amino]-acetic acid a) Dimethyl-thiocarbamic acid O-(2-acetyl-3-fluoro-phenyl)ester 1-(2-Fluoro-6-hydroxy-phenyl)-ethanone (2.5 g, 16.22 mmol) (available from Apollo Scientific) was dissolved in anhydrous DMF (20 mL.) Dimethylthiocarbamoyl chloride (2.2 g, 17.84 mmol) and DABCO (2.0 g, 17.84 mmol) were added sequentially in one portion. The reaction was permitted to stir overnight at ambient temperature. The reaction was quenched by pouring it into a mixture of 1N HCl-ice. The oily residue was extracted with dichloromethane and dried over sodium sulfate. The crude residue was purified by SGC (20% ethyl acetate in hexanes) to provide the title compound (2.93 g.) $^1$H NMR (200 MHz, CDCl$_3$): δ (ppm)=7.407 (dd, 1H), 7.026 (t, 1H), 6.876 (d, 1H), 3.404 (s, 3H), 3.341 (sd, 3H), 2.58 (d, 3H).

b) Dimethyl-thiocarbamic acid S-(2-acetyl-3-fluoro-phenyl) ester

Dimethyl-thiocarbamic acid O-(2-acetyl-3-fluoro-phenyl) ester (2.75 g, 11.4 mmol) was dissolved in ethyl acetate (3 mL) and placed in a CEM microwave vessel. The vessel was heated to 170° C. for 8 hours using a CEM Discovery Microwave. After cooling, the crude material was purified directly (SGC; 5% Ethyl acetate in hexanes) to provide the title compound (2.1 g). $^1$H NMR (200 MHz, CDCl$_3$): δ (ppm)=7.422-7.313 (m, 2H), 7.233-7.094 (m, 1H), 3.115-3.014 (br d, 6H), 2.573 (d, 3H).

c) 5-Fluoro-4-hydroxy-thiochromen-2-one

Dimethyl-thiocarbamic acid S-(2-acetyl-3-fluoro-phenyl) ester (2.1 g, 8.7 mmol) was dissolved in anhydrous THF (25 mL.) This solution was slowly added to a rapidly stirring solution potassium tert-butoxide (22 mL, 1M, 22 mmol) via cannula. Upon complete addition, the reaction was permitted to stir overnight at ambient temperature. The reaction was concentrated in vacuo and the residue dissolved in water and extracted three times with an equal volume of 5:1 hexanes: ethyl acetate. The organic portions were discarded and the aqueous phase acidified with 1N HCl to precipitate the product. The product was isolated via filtration and dried to provide the title compound (1.59 g.) $^1$H NMR (200 MHz, DMSO-d$_6$): δ (ppm)=12.192 (br s, 1H), 7.651-7.546 (m, 1H), 7.421 (d, 1H), 6.036 (s, 1H).

d) [(5-Fluoro-4-hydroxy-2-oxo-2H-thiochromene-3-carbonyl)-amino]-acetic acid ethyl ester 5-Fluoro-4-hydroxy-thiochromen-2-one (500 mg, 2.55 mmol) was placed in a CEM Microwave vessel and suspended in anhydrous DCM (5 mL.) Triethylamine (710 uL, 5.1 mmol) and isocyanato-acetic acid ethyl ester (572 uL, 5.1 mmol) were added in one portion and the reaction heated to 120° C. in a CEM Discovery Microwave system. After three hours, the reaction was cooled diluted with 10 volumes of dichloromethane, washed with an equal volume of 1N HCl and dried over magnesium sulfate to provide the title compound which was used in the next step without further purification.

e) [(5-Fluoro-4-hydroxy-2-oxo-2H-thiochromene-3-carbonyl)-amino]-acetic acid

[(5-Fluoro-4-hydroxy-2-oxo-2H-thiochromene-3-carbonyl)-amino]-acetic acid was prepared under conditions analogous to 44(b.) MS ESI(−) m/e: 296.0255 (M−1).

Example 53

[(7-Cyclopropyl-4-hydroxy-2-oxo-2H-thiochromene-3-carbonyl)-amino]-acetic acid a) 7-Cyclopropyl-4-hydroxy-2-oxo-2H-thiochromene-3-carboxylic acid methyl ester 7-Cyclopropyl-4-hydroxy-2-oxo-2H-thiochromene-3-carboxylic acid methyl ester was prepared from 7-bromo-4-hydroxy-2-oxo-2H-thiochromene-3-carboxylic acid methyl ester under conditions analogous to Example 7(a) using cyclopropylboronic acid. The crude material was used in the next step without purification.

b) [(7-Cyclopropyl-4-hydroxy-2-oxo-2H-thiochromene-3-carbonyl)-amino]-acetic acid

[(7-Cyclopropyl-4-hydroxy-2-oxo-2H-thiochromene-3-carbonyl)-amino]-acetic acid was prepared under conditions analogous to Example 3(d) using glycine. MS ESI(−) m/e: 317.9775 (M−1).

Example 54

{[4-Hydroxy-7-(2-methyl-5-trifluoromethyl-2H-pyrazol-3-yl)-2-oxo-2H-thiochromene-3-carbonyl]-amino}-acetic acid a) 4-Hydroxy-7-(2-methyl-5-trifluoromethyl-2H-pyrazol-3-yl)-2-oxo-2H-thiochromene-3-carboxylic acid methyl ester 4-Hydroxy-7-(2-methyl-5-trifluoromethyl-2H-pyrazol-3-yl)-2-oxo-2H-thiochromene-3-carboxylic acid methyl ester was prepared from 7-bromo-4-hydroxy-2-oxo-2H-thiochromene-3-carboxylic acid methyl ester under conditions analogous to Example 44(a) using 1-Methyl-5-tributylstannanyl-3-trifluoromethyl-1H-pyrazole. The crude material was used in the next step without purification.

b) {[4-Hydroxy-7-(2-methyl-5-trifluoromethyl-2H-pyrazol-3-yl)-2-oxo-2H-thiochromene-3-carbonyl]-amino}-acetic acid {[4-Hydroxy-7-(2-methyl-5-trifluoromethyl-2H-pyrazol-3-yl)-2-oxo-2H-thiochromene-3-carbonyl]-amino}-acetic acid was prepared under conditions analogous to Example 3(d) using glycine. MS ESI(−) m/e: 426.0042 (M−1).

Example 55

2-(S)-{[4-Hydroxy-7-(2-methyl-5-trifluoromethyl-2H-pyrazol-3-yl)-2-oxo-2H-thiochromene-3-carbonyl]-amino}-propionic acid 2-{[4-Hydroxy-7-(2-methyl-5-trifluoromethyl-2H-pyrazol-3-yl)-2-oxo-2H-thiochromene-3-carbonyl]-amino}-propionic acid was prepared under conditions analogous to Example 3(d) using L-alanine. MS ESI(−) m/e: 440.0124 (M−1).

Example 56

[(6-Chloro-4-hydroxy-2-oxo-8-phenylethynyl-2H-thiochromene-3-carbonyl)-amino]-acetic acid a) [(6-Chloro-4-hydroxy-2-oxo-8-phenylethynyl-2H-thiochromene-3-carbonyl)-amino]-acetic acid ethyl ester

[(6-Chloro-4-hydroxy-2-oxo-8-phenylethynyl-2H-thiochromene-3-carbonyl)-amino]-acetic acid ethyl ester was prepared under conditions analogous to Example 44(a) using tributyl-phenylethynyl-stannane. The crude material was used in the next step without purification.

b) [(6-Chloro-4-hydroxy-2-oxo-8-phenylethynyl-2H-thiochromene-3-carbonyl)-amino]-acetic acid

[(6-Chloro-4-hydroxy-2-oxo-8-phenylethynyl-2H-thiochromene-3-carbonyl)-amino]-acetic acid was prepared under conditions analogous to Example 44(b). MS ESI(−) m/e: 411.9288, 413.8327 (M−1).

Example 57

2-(S)-[(4-Hydroxy-2-oxo-2H-thiochromene-3-carbonyl)-amino]-propionic acid

A mixture of 4-hydroxy-2-oxo-2H-thiochromene-3-carboxylic acid methyl ester compound 3(c) (103 mg, 0.44 mmol), L-alanine (583 mg, 6.55 mmol) and NaOMe (285 mg, 5.28 mmol) in 2-methoxyethanol (14 mL) was refluxed for 6 h and concentrated. Residue was dissolved in water (100 mL) and acidified by 1 N HCl solution to pH=3-4. Precipitate was collected and rinsed with water. It was dried in vacuo and then triturated in MeOH (10 mL). Solid was collected and dried in vacuo to provide the title compound (57 mg). MS ESI(−) m/e: 291.12 (M−1).

Example 58

[(6-Chloro-4-hydroxy-2-oxo-2H-thiochromene-3-carbonyl)-amino]-acetic acid a) 6-Chloro-2,2-dimethyl-benzo[d][1,3]oxathiin-4-one A mixture of 5-chloro-2-mercapto-benzoic acid (2.5 g, 13.25 mmol) (commercial available from Biogene Organics), acetone (7.9 g, 136 mmol), (+/−) camphor sulfonic acid (1.54 g, 6.63 mmol) and 4 A moleculare sieves (1.5 g) in CHCl$_3$ was heated to refulx for 3 days. Reaction mixture was diluted with CH$_2$Cl$_2$ (100 mL) and then washed with saturated NaHCO$_3$ aqueous solution (2×50 mL). Organic layer was washed with brine, dried over MgSO$_4$, filtered and concentrated. Crude residue was passed through a pad of silica gel and eluted with CH$_2$Cl$_2$. Filtrate was concentrated to provide the title compound (769 mg). $^1$H NMR (200 MHz, CDCl$_3$): δ (ppm)=8.15 (d, J=2.4 Hz, 1H), 7.44 (dd, J=8.3, 2.0 Hz, 1H), 7.21 (d, J=8.3 Hz, 1H), 1.83 (s, 6H).

b) 6-Chloro-4-hydroxy-2-oxo-2H-thiochromene-3-carboxylic acid methyl ester

To a cold mixture of the above compound (750 mg, 3.25 mmol) and dimethyl malonate (1.07 g, 8.13 mmol) in DMF (16 mL) at o ° C. was added NaH (390 mg, 9.75 mmol) (60% disopersed in mineral oil). Resulting mixture was stirred at o ° C. for 5 min, then in a 120° C. oil bath overnight. It was quenched with water (160 mL) and acidified using 1 N HCl solution to pH=3-4. Precipitate was collected and rinsed with water. After dried in vacuo, the crude solid was triturated in hot MeOH (40 mL). After cooled, solid was collected and dried to provide the title compound (350 mg). MS ESI(−) m/e: 268.98 (M−1).

c) [(6-Chloro-4-hydroxy-2-oxo-2H-thiochromene-3-carbonyl)-amino]-acetic acid

A mixture of the above eater (120 mg, 0.44 mmol) and sodium glycinate (213 mg, 2.2 mmol) in 2-methoxyethanol (5 mL) was microwaved at 150° C. for 35 min. Reaction mixture was concentrated and dissolved in water (60 mL). Insoluble solid was filtered off. Aqueous filtrate was acidified using 1 N HCl solution and extrated with EtOAc. Organic layer was washed with brine, dried over MgSO$_4$, filtered and concentrated to provide the title compound (129 mg). MS ESI(−) m/e: 311.92 (M−1).

Example 59

2-(S)-[(6-Chloro-4-hydroxy-2-oxo-2H-thiochromene-3-carbonyl)-amino]-propionic acid A mixture of 6-chloro-4-hydroxy-2-oxo-2H-thiochromene-3-carboxylic acid methyl ester (Compound 58(b)) (100 mg, 0.37 mmol), L-alanine (165 mg, 1.85 mmol) and NaOMe (80 mg, 1.48 mmol) in 2-methoxyethanol (5.2 mL) was microwaved at 150° C. for 2 h and concentrated. Residue was dissolved in water (60 mL). Insoluble solid was filtered off. The Aqueous filtrate was acidified using 1 N HCl solution to pH=3-4. Precipitate was collected and dried. It was then triturated with MeOH (2 mL). Solid was collected and dried in vacuo to provide the title compound (50 mg). MS ESI(−) m/e: 325.93 (M−1).

Example 60

[(7-Chloro-4-hydroxy-2-oxo-2H-thiochromene-3-carbonyl)-amino]-acetic acid a) 4-Chloro-2-hydroxy-benzoic acid methyl ester

To a mixture of 4-chlorosalicylic acid (16 g, 92.6 mmol) in MeOH (210 mL) was added conc. HCl solution (5 mL). The resultant solution was refluxed for 23 h. After cooled, solid NaHCO$_3$ was added to neutralize the mixture and then was concentrated. The slurry was suspended in EtOAc and filtered through a silica gel plug, washing with EtOAc. The filtrate was washed with ¼ saturated NaHCO$_3$ solution (2×), brine, dried over Na$_2$SO$_4$, filtered and concentrated to provide the title compound (17.2 g). MS ESI(−) m/e: 185.0 (M−1).

b) 4-Chloro-2-dimethylthiocarbamoyloxy-benzoic acid methyl ester

To a mixture of the above ester (6.48 g, 34.7 mmol) in DMF (40 mL) was added DABCO (11.6 g, 104 mmol) and dimethylthiocarbamoyl chloride (4.5 g, 36.5 mmol). The resultant mixture was stirred at rt for 20 h and poured into EtOAc/1 N HCl aq solution. Organic phase was washed with 1 N HCl solution, saturated NaHCO$_3$ solution and brine. It was filtered, dried over Na$_2$SO$_4$, filtered and concentrated to provide the title compound (8.86 g) as pale yellow solid. $^1$H NMR (200 MHz, CDCl$_3$): δ (ppm)=7.93 (d, J=8.2 Hz, 1H), 7.28 (dd, J=8.5, 2.2 Hz, 1H), 7.13 (d, J=2.0 Hz, 1H). 3.83 (s, 3H), 3.46 (s, 3H), 3.38 (s, 3H).

c) 4-Chloro-2-dimethylcarbamoylsulfanyl-benzoic acid methyl ester

The above neat ester (8 g) was slowly heated to 220 C in a sand bath for 3.5 h. After cooled, the mixture was subjected to silica gel chromatography (eluting with 10%-50% EtOAc/hexanes) to provide the title compound 7.14 g as a white solid. $^1$H NMR (200 MHz, CDCl$_3$): δ (ppm)=7.84 (d, J=8.5 Hz, 1H), 7.62 (d, J=2.0 Hz, 1H), 7.38 (dd, J=8.5, 2.0 Hz, 1H). 3.88 (s, 3H), 3.09 (br d, 6H).

d) 4-Chloro-2-dimethylcarbamoylsulfanyl-benzoic acid

The above ester (5 g, 18.3 mmol) was dissolved in THF (30 mL) and cooled in an ice bath. 1 N NaOH aq solution was then slowly added and the mixture was stirred at rt for 24 h. It was diluted with water, acidified with 1 N HCl and extracted with EtOAc. The organic phase was washed with brine, dried over Na$_2$SO$_4$, filtered and concentrated to provide the title compound (4.74 g) as a white solid. MS ESI(+) m/e: 259.99 (M+1).

e) 2-(4-Chloro-2-dimethylcarbamoylsulfanyl-benzoyl)-malonic acid dimethyl ester 2-(4-Chloro-2-dimethylcarbamoylsulfanyl-benzoyl)-malonic acid dimethyl ester was prepared from the above carboxylic acid under conditions analogous to Example 5 (d). MS ESI(+) m/e: 375.96, 374.00 (M+1).

f) 7-Chloro-4-hydroxy-2-oxo-2H-thiochromene-3-carboxylic acid methyl ester

7-Chloro-4-hydroxy-2-oxo-2H-thiochromene-3-carboxylic acid methyl ester was prepared from the above ester under conditions analogous to Example 5 (e). MS ESI(+) m/e: 272.92, 270.95 (M+1).

g) [(7-Chloro-4-hydroxy-2-oxo-2H-thiochromene-3-carbonyl)-amino]-acetic acid

[(7-Chloro-4-hydroxy-2-oxo-2H-thiochromene-3-carbonyl)-amino]-acetic acid was prepared from the above ester under conditions analogous to Example 3 (d). MS ESI(−) m/e: 313.92, 311.92 (M−1).

Example 61

2-(S)-1(7-Chloro-4-hydroxy-2-oxo-2H-thiochromene-3-carbonyl)-amino]-propionic acid A mixture of 7-chloro-4-hydroxy-2-oxo-2H-thiochromene-3-carboxylic acid methyl ester (Compound 60 (f)) (125 mg, 0.46 mmol), L-alanine (494 mg, 5.55 mmol) and NaOMe (249 mg, 4.62 mmol) in 2-methoxyethanol (5 mL) was heated in a 115° C. sand bath for 24 h. 1 N HCl aq. solution was added to precipitate the product. The solid was collected and rinsed with water. It was dried in vacuo and then triturated with MeOH to provide the title compound (102 mg). MS ESI(−) m/e: 327.96, 325.97 (M−1).

Example 62

[(6-Benzyloxy-4-hydroxy-2-oxo-2H-thiochromene-3-carbonyl)-amino]-acetic acid a) 6-Hydroxy-2,2-dimethyl-benzo[1,3]dioxin-4-one 10 mL of trifluoroacetic anhydride and 4 mL of acetone were added to a slurry of 2,5-dihydroxybenzoic acid (available from Aldrich) (2 g, 13 mmol) in 16 mL of trifluoroacetic acid. The mixture was stirred at 55° C. for 23 h and then at 85° C. for 2.5 h under a nitrogen atmosphere. The reaction mixture was concentrated under vacuum, dissolved and re-concentrated from toluene twice, and dried under vacuum. The crude solid was dissolved in ethyl acetate and washed twice with saturated sodium bicarbonate solution and once with brine. The organic fraction was dried over sodium sulfate and concentrated. Crude product was purified by column chromatography (eluting from silica gel with a gradient of 5 to 50% ethyl acetate in hexanes) to provide the title product as a yellow solid 0.47 g. $^1$H NMR (200 MHz, CDCl$_3$): δ (ppm)= 7.43 (d, J=2.8 Hz, 1H), 7.08 (dd, J=9.0, 3.1 Hz, 1H), 6.85 (d, J=9.0 Hz, 1H), 5.45 (s, 1H), 1.71 (s, 6H).

b)
6-Benzyloxy-2,2-dimethyl-benzo[1,3]dioxin-4-one

A mixture of the above compound (20.3 g, 105 mmol), benzyl bromide (16.2 mL, 136 mmol) and Cs$_2$CO$_3$ (44.2 g, 136 mmol) in DMF (210 mL) was stirred at rt for 20 h. The volume of the reaction mixture was reduced to ca. 150 mL under high vacuum evaporation and then diluted with EtOAc/hexanes mixture. Solid was filtered off and filtrate was concentrated under high vacuum. Crude residue was passed through a pad of silica gel, eluting with (1/1) EtOAc/hexanes to provide the title compound (37.4 g). $^1$H NMR (200 MHz, CDCl$_3$): δ (ppm)=7.48-6.85 (m, 8H), 5.04 (s, 2H), 1.71 (s, 6H).

c) 5-Benzyloxy-2-hydroxy-benzoic acid methyl ester

NaOMe solid (5.67 g, 105 mmol) was added in one portion to a mixture of the above compound (34 g, 105 mmol) in (1/1) MeOH/THF (420 mL). The reaction mixture was stirred at rt for 1 h and concentrate to ⅓ of its volume. It was then partitioned between 1 N HCl and EtOAc. Organic phase was washed with water, brine, dried over Na$_2$SO$_4$, filtered and concentrated. Crude residue was purified by silica gel chromatography (eluting with 10%-40% EtOAc/hexanes) to provide the title compound (15 g) as a pale yellow solid. $^1$H NMR (200 MHz, CDCl$_3$): δ (ppm)=10.36 (s, 1H), 7.41-7.10 (m, 7H), 6.89 (d, J=9.0 Hz, 1H), 5.00 (s, 2H), 3.94 (s, 3H).

d)
5-Benzyloxy-2-dimethylthiocarbamoyloxy-benzoic acid methyl ester

5-Benzyloxy-2-dimethylthiocarbamoyloxy-benzoic acid methyl ester was prepared from the above ester under conditions analogous to Example 60 (b). $^1$H NMR (200 MHz, CDCl$_3$): δ (ppm)=7.58 (d, J=3.1 Hz, 1H), 7.43-7.11 (m, 6H), 7.02 (d, J=8.6 Hz, 1H), 5.06 (s, 2H), 3.82 (s, 3H), 3.46 (s, 3H), 3.38 (s, 3H).

e)
5-Benzyloxy-2-dimethylcarbamoylsulfanyl-benzoic acid methyl ester 9.2 g of the above ester was subjected to microwave reaction and the reaction was carried out 1 g at a time. 1 g of the above ester was dissolved in bromobenzene (4 mL) and was heated in a microwave reactor at 225° C. for 140 min. Combined reaction mixtures was diluted with small amount of EtOAc and filtered to collect the solid. Solid was washed with small amount of EtOAc and dried to provide the title compound (4.75 g). $^1$H NMR (200 MHz, CDCl$_3$): δ (ppm)=7.49-7.30 (m, 7H), 7.05 (dd, J=8.6, 2.8 Hz, 1H), 5.08 (s, 2H), 3.86 (s, 3H), 3.05 (br s, 36H).

f)
5-Benzyloxy-2-dimethylcarbamoylsulfanyl-benzoic acid

5-Benzyloxy-2-dimethylcarbamoylsulfanyl-benzoic acid was prepared from the above ester under conditions analogous to Example 60 (d). $^1$H NMR (200 MHz, CDCl$_3$): δ (ppm)=7.49-7.31 (m, 7H), 7.02 (dd, J=8.6, 3.1 Hz, 1H), 5.09 (s, 2H), 3.18 (s, 3H), 3.06 (s, 3H).

g) 2-(5-Benzyloxy-2-dimethylcarbamoylsulfanyl-benzoyl)-malonic acid dimethyl ester 2-(5-Benzyloxy-2-dimethylcarbamoylsulfanyl-benzoyl)-malonic acid dimethyl ester was prepared from the above carboxylic acid under conditions analogous to Example 5 (d). MS ESI(−) m/e: 444.05 (M−1).

h) 6-Benzyloxy-4-hydroxy-2-oxo-2H-thiochromene-3-carboxylic acid methyl ester

6-Benzyloxy-4-hydroxy-2-oxo-2H-thiochromene-3-carboxylic acid methyl ester was prepared from the above ester under conditions analogous to Example 5 (e). $^1$H NMR (200 MHz, DMSO-d6): δ (ppm)=7.71 (d, J=2.8 Hz, 1H), 7.47-7.32 (m, 5H), 7.16 (d, J=8.6 Hz, 1H), 7.05 (dd, J=8.6, 2.8 Hz, 1H), 5.11 (s, 2H), 3.54 (s, 3H).

i) [(6-Benzyloxy-4-hydroxy-2-oxo-2H-thiochromene-3-carbonyl)-amino]-acetic acid

[(6-Benzyloxy-4-hydroxy-2-oxo-2H-thiochromene-3-carbonyl)-amino]-acetic acid was prepared from the above ester under conditions analogous to Example 3 (d). MS ESI (−) m/e: 383.95 (M−1).

Example 63

[(6-Cyclohexylmethoxy-4-hydroxy-2-oxo-2H-thiochromene-3-carbonyl)-amino]-acetic acid a) 6-Benzyloxy-4-[2-(tert-butyl-diphenyl-silanyl)-ethoxy]-2-oxo-2H-thiochromene-3-carboxylic acid methyl ester To a mixture of 6-benzyloxy-4-hydroxy-2-oxo-2H-thiochromene-3-carboxylic acid methyl ester (Compound 62 (h), 591 mg, 1.73 mmol) and 2-(tert-Butyl-diphenyl-silanyl)-ethanol (687 mg, 2.42 mmol) (prepared according to the procedure published in *J. Org. Chem.* 2005, 70(4), 1467-1470) in THF (7 mL) was added triphenylphosphine (634 mg, 2.42 mmol), and DIAD (489 mg, 2.42 mmol). The resultant mixture was stirred at rt for 3.5 h. After concentration, the crude residue was purified by silica gel chromatography (eluting with 0-75% EtOAc/hexanes) to provide the title compound (697 mg). $^1$H NMR (200 MHz, CDCl$_3$): δ (ppm)=7.69-7.14 (m, 18H), 5.83 (s, 2H), 4.25-4.09 (m, 2H), 3.49 (s, 3H), 1.89-1.81 (m, 2H), 1.08 (s, 9H).

b) 4-(4,4-Dimethyl-3,3-diphenyl-pentyloxy)-6-hydroxy-2-oxo-2H-thiochromene-3-carboxylic acid methyl ester Pd/C (10% activated, 275 mg) was added to a mixture of the above ester (690 mg, 1.13 mmol) in EtOAc/EtOH (7 mL/5 mL). The mixture was hydrogenated in a Parr shaker under high pressure H$_2$ gas (25-30 psi) at rt overnight. It was filtered through a pad of celite and concentrated. Residue was purified by silica gel chromatography (eluting with 10-60% EtOAc/hexanes) to provide the title compound (208 mg). $^1$H NMR (200 MHz, CDCl$_3$): δ (ppm)=7.62-6.99 (m, 13H), 4.77 (s, 1H), 4.25 (m, 2H), 3.57 (s, 3H), 1.88 (m, 2H), 1.07 (s, 9H).

c) 6-Cyclohexylmethoxy-4-(4,4-dimethyl-3,3-diphenyl-pentyloxy)-2-oxo-2H-thiochromene-3-carboxylic acid methyl ester To a mixture of the above ester (150 mg, 0.29 mmol) in DMF (1 mL) was added cyclohexylmethyl bromide (144 mg, 0.81 mmol) and Cs$_2$CO$_3$ (222 mg, 0.68 mmol). The resultant mixture was stirred at 50° C. overnight. It was diluted with EtOAc and then washed with water, brine. The organic phase was dried over Na$_2$SO$_4$, filtered and concentrated. Residue was purified by silica gel chromatography (eluting with 0-40% EtOAc/hexanes) to provide the title compound (159 mg). $^1$H NMR (200 MHz, CDCl$_3$): δ (ppm)=7.59-7.08 (m, 13H), 4.26-4.18 (m, 2H), 3.81 (d, J=7.8 Hz, 2H), 3.54 (s, 3H), 1.95-1.25 (m, 13H), 1.08 (s, 9H).

d) 6-Cyclohexylmethoxy-4-hydroxy-2-oxo-2H-thiochromene-3-carboxylic acid methyl ester A mixture of the above ester (155 mg, 0.25 mmol) and TBAF (1M in THF, 0.5 mL, 0.5 mmol) in THF (1 mL) was stirred at rt for 8 h. It was poured into a mixture of EtOAc and 0.1 N HCl aq. solution. Organic phase was washed with water, brine, dried over Na$_2$SO$_4$, filtered and concentrated. Crude residue was triturated with hexanes and then MeOH and dried to provide the title compound (56 mg). MS ESI(−) m/e: 347.04 (M−1).

e) [(6-Cyclohexylmethoxy-4-hydroxy-2-oxo-2H-thiochromene-3-carbonyl)-amino]-acetic acid

[(6-Cyclohexylmethoxy-4-hydroxy-2-oxo-2H-thiochromene-3-carbonyl)-amino]-acetic acid was prepared from the above ester under conditions analogous to Example 3 (d). MS ESI(−) m/e: 390.02 (M−1).

Example 64

[(6-Hexyloxy-4-hydroxy-2-oxo-2H-thiochromene-3-carbonyl)-amino]-acetic acid a) 4-[2-(tert-Butyl-diphenyl-silanyl)-ethoxy]-6-hexyloxy-2-oxo-2H-thiochromene-3-carboxylic acid methyl ester 4-[2-(tert-Butyl-diphenyl-silanyl)-ethoxy]-6-hexyloxy-2-oxo-2H-thiochromene-3-carboxylic acid methyl ester was prepared from 4-(4,4-Dimethyl-3,3-diphenyl-pentyloxy)-6-hydroxy-2-oxo-2H-thiochromene-3-carboxylic acid methyl ester (Compound 63 (b)) and 1-iodo-hexane under conditions analogous to Example 63 (c). $^1$H NMR (200 MHz, CDCl$_3$): δ (ppm)=7.59-7.07 (m, 13H), 4.22 (m, 2H), 3.97 (t, J=6.4 Hz, 2H), 3.54 (s, 3H), 1.95-0.89 (m, 13H), 1.08 (s, 9H).

b) 6-Hexyloxy-4-hydroxy-2-oxo-2H-thiochromene-3-carboxylic acid methyl ester 6-Hexyloxy-4-hydroxy-2-oxo-2H-thiochromene-3-carboxylic acid methyl ester was prepared from the above ester under conditions analogous to Example 63 (d). MS ESI(−) m/e: 335.06 (M−1).

c) [(6-Hexyloxy-4-hydroxy-2-oxo-2H-thiochromene-3-carbonyl)-amino]-acetic acid

[(6-Hexyloxy-4-hydroxy-2-oxo-2H-thiochromene-3-carbonyl)-amino]-acetic acid was prepared from the above ester under conditions analogous to Example 3 (d). MS ESI(−) m/e: 378.04 (M−1).

---

What is claimed is:

1. A compound of Formula I:

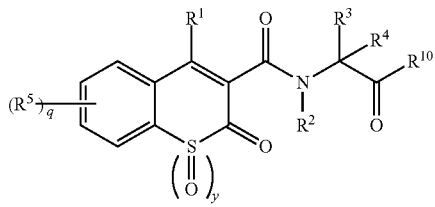

wherein:

q is 1, 2, 3, or 4;

y is 0-2;

$R^1$ is selected from the group consisting of —$OR^{18}$, hydroxy, acyloxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, thio, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, amino, substituted amino, and acylamino;

$R^2$ is selected from the group consisting of hydrogen, alkyl, and substituted alkyl;

$R^3$ is selected from the group consisting of hydrogen, deuterium, alkyl, and substituted alkyl;

$R^4$ is selected from the group consisting of hydrogen, deuterium, and methyl;

each $R^5$ is independently selected from the group consisting of cyano, acyl, substituted amino, acylamino, sulfonyl, substituted sulfonyl, substituted alkyl, alkenyl, substituted alkenyl, alkynyl, substituted alkynyl, cycloalkyl, substituted cycloalkyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heteroaryl, and substituted heteroaryl;

or two $R^5$ taken together with the carbon atoms to which they are attached form a 5- or 6-membered aryl or substituted aryl;

$R^{10}$ is —$NR^{11}R^{12}$ or —$OR^{13}$;

$R^{11}$ and $R^{12}$ are independently selected from the group consisting hydrogen, alkyl, alkylene-cycloalkyl, heterocyclic, and aryl;

or $R^{11}$ and $R^{12}$ are taken together with the nitrogen to which they are attached form a 5- or 6-membered heterocyclic, substituted heterocyclic, heteroaryl or substituted heteroaryl;

$R^{13}$ is selected from the group consisting of a cation, hydrogen and alkyl which is unsubstituted or substituted with one or more substituents independently selected from the group consisting of cycloalkyl, heterocyclic, aryl, and heteroaryl; and $R^{18}$ is a cation;

or a pharmaceutically acceptable salt, single stereoisomer, mixture of stereoisomers, or tautomer thereof.

2. The compound of claim 1, wherein $R^2$ is hydrogen.

3. The compound of claim 1, wherein q is 1 or 2.

4. The compound of claim 1, wherein $R^1$ is hydroxy.

5. The compound of claim 1, wherein $R^1$ is hydroxy and $R^2$ is hydrogen.

6. The compound of claim 1, wherein $R^1$ is hydroxy; and $R^4$ and $R^2$ are hydrogen.

7. The compound of claim 1, wherein each $R^5$ is independently selected from the group consisting of acylamino, substituted alkyl, substituted alkynyl, cycloalkyl, aryl, substituted aryl, alkoxy, substituted alkoxy, heteroaryl, and substituted heteroaryl.

8. The compound of claim 1, wherein $R^5$ is selected from a ($C_1$-$C_3$)-alkynyl, or ($C_1$-$C_3$)-cycloalkyl; each of which is optionally substituted with an aryl.

9. The compound of claim 1, wherein $R^5$ is ($C_1$-$C_6$)-alkoxy, which is optionally substituted with a cycloalkyl or aryl.

10. The compound of claim 1, wherein each $R^5$ is independently selected from the group consisting of aryl and heteroaryl; each of which is optionally substituted with at least one of methoxy, chloro, fluoro or trifluoromethyl.

11. The compound of claim 1, wherein two $R^5$ taken together with the carbon atoms to which they are attached form a 5- or 6-membered aryl or substituted aryl.

12. The compound of claim 11, wherein the aryl is phenyl.

13. The compound of claim 1, wherein $R^{10}$ is —$OR^{13}$; and $R^{13}$ is selected from the group consisting of a cation, hydrogen, and alkyl; each of which is optionally substituted with one or more substituents selected from the group consisting of cycloalkyl, heterocyclic, aryl, and heteroaryl.

14. The compound of claim 1, wherein $R^1$ is hydroxy;

$R^2$ and $R^4$ are hydrogen;

$R^3$ is selected from the group consisting of hydrogen, alkyl, and substituted alkyl; and each $R^5$ is independently selected from the group consisting of acylamino, substituted alkyl, substituted alkynyl, cycloalkyl, aryl, substituted aryl, alkoxy, substituted alkoxy, heteroaryl, and substituted heteroaryl.

15. The compound of claim 1, wherein
q is 1 or 2;
$R^1$ is hydroxy;
$R^2$ and $R^4$ are hydrogen;
$R^3$ is selected from the group consisting of hydrogen, alkyl, and substituted alkyl;
each $R^5$ is independently selected from the group consisting of acylamino, substituted alkyl, substituted alkynyl, cycloalkyl, aryl, substituted aryl, alkoxy, substituted alkoxy, heteroaryl, and substituted heteroaryl; and
$R^{10}$ is —$OR^{13}$; wherein $R^{13}$ is hydrogen or alkyl.

16. The compound of claim 1, wherein
q is 1;
$R^1$ is hydroxy;
$R^2$ and $R^4$ are hydrogen;
$R^3$ is selected from the group consisting of hydrogen, alkyl, and substituted alkyl; and
$R^{10}$ is —$OR^{13}$; wherein $R^{13}$ is hydrogen or alkyl.

17. The compound of claim 1, wherein
q is 1 or 2;
$R^1$ is hydroxy;
$R^2$, $R^3$ and $R^4$ are hydrogen;
each $R^5$ is independently selected from the group consisting of acylamino, substituted alkyl, substituted alkynyl, cycloalkyl, aryl, substituted aryl, alkoxy, substituted alkoxy, heteroaryl, and substituted heteroaryl; and
$R^{10}$ is —$OR^{13}$; wherein $R^{13}$ is hydrogen or alkyl.

18. A compound of Formula II:

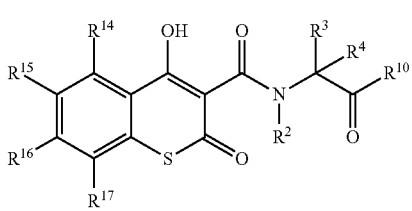

II wherein
$R^2$ is selected from the group consisting of hydrogen, alkyl, and substituted alkyl;
$R^3$ is selected from the group consisting of hydrogen, deuterium, alkyl, and substituted alkyl;
$R^4$ is selected from the group consisting of hydrogen, deuterium, and methyl;
$R^{14}$, $R^{15}$, $R^{16}$ and $R^{17}$ are independently selected from the group consisting of hydrogen, cyano, acyl, substituted amino, acylamino, sulfonyl, substituted sulfonyl, substituted alkyl, alkenyl, substituted alkenyl, alkynyl, substituted alkynyl, cycloalkyl, substituted cycloalkyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heteroaryl, and substituted heteroaryl;
or $R^{14}$ and $R^{15}$, $R^{15}$ and $R^{16}$, or $R^{16}$ and $R^{17}$ are taken together with the carbon atoms to which they are attached to form a 5- or 6-membered aryl or substituted aryl;
$R^{10}$ is —$NR^{11}R^{12}$ or —$OR^{13}$;

$R^{11}$ and $R^{12}$ are independently selected from the group consisting hydrogen, alkyl, alkylene-cycloalkyl, heterocyclic, and aryl;
or $R^{11}$ and $R^{12}$ are taken together with the nitrogen to which they are attached form a 5- or 6-membered heterocyclic, substituted heterocyclic, heteroaryl or substituted heteroaryl; and
$R^{13}$ is selected from the group consisting of a cation, hydrogen and alkyl which is unsubstituted or substituted with one or more substituents independently selected from the group consisting of cycloalkyl, heterocyclic, aryl, and heteroaryl;
or a pharmaceutically acceptable salt, single stereoisomer, mixture of stereoisomers, or tautomer thereof;
provided that at least one of $R^{14}$, $R^{15}$, $R^{16}$ and $R^{17}$ is other than hydrogen.

19. The compound of claim 18, wherein $R^{14}$ and $R^{17}$ are independently selected from the group consisting of hydrogen, substituted alkyl, substituted alkynyl, aryl, substituted aryl, heteroaryl, and substituted heteroaryl.

20. The compound of claim 18, wherein $R^{15}$ and $R^{16}$ are independently selected from the group consisting of hydrogen, acylamino, substituted alkyl, cycloalkyl, aryl, substituted aryl, alkoxy, substituted alkoxy, heteroaryl, and substituted heteroaryl.

21. The compound of claim 18, wherein $R^2$ is hydrogen.

22. The compound of claim 18, wherein $R^4$ is hydrogen.

23. The compound of claim 18, wherein $R^2$ and $R^4$ are hydrogen.

24. The compound of claim 18, wherein $R^3$ is selected from the group consisting of hydrogen and methyl.

25. The compound of claim 18, wherein $R^2$, $R^3$, and $R^4$ are hydrogen.

26. The compound of claim 18, wherein $R^{10}$ is —$OR^{13}$.

27. The compound of claim 18, wherein $R^{10}$ is —$OR^{13}$; and $R^{13}$ is hydrogen, or alkyl which is unsubstituted or substituted with one or more substituents independently selected from the group consisting of cycloalkyl, heterocyclic, aryl, and heteroaryl.

28. The compound of claim 18, wherein $R^{10}$ is —$OR^{13}$; and $R^{13}$ is $C_1$-$C_4$ alkyl.

29. The compound of claim 18, wherein $R^{10}$ is —$OR^{13}$; and $R^{13}$ is hydrogen.

30. The compound of claim 18, wherein
$R^2$ and $R^4$ are hydrogen;
$R^3$ is selected from the group consisting of hydrogen, alkyl, and substituted alkyl; and
$R^{14}$, $R^{15}$, $R^{16}$ and $R^{17}$ are independently selected from the group consisting of hydrogen, acylamino, substituted alkyl, substituted alkynyl, cycloalkyl, aryl, substituted aryl, alkoxy, substituted alkoxy, heteroaryl, and substituted heteroaryl.

31. The compound of claim 18, wherein
$R^2$ and $R^4$ are hydrogen;
$R^3$ is selected from the group consisting of hydrogen, alkyl, and substituted alkyl;
$R^{14}$, $R^{15}$, $R^{16}$ and $R^{17}$ are independently selected from the group consisting of hydrogen, acylamino, substituted alkyl, substituted alkynyl, cycloalkyl, aryl, substituted aryl, alkoxy, substituted alkoxy, heteroaryl, and substituted heteroaryl; and
$R^{10}$ is —$OR^{13}$; wherein $R^{13}$ is a cation, hydrogen or alkyl.

32. The compound of claim 18, wherein
R², R³, and R⁴ are hydrogen;
R¹⁴ and R¹⁷ are independently selected from the group consisting of hydrogen, substituted alkyl, substituted alkynyl, aryl, substituted aryl, heteroaryl, and substituted heteroaryl;
R¹⁵ and R¹⁶ are independently selected from the group consisting of hydrogen, substituted alkyl, alkoxy, aryl, substituted aryl, heteroaryl, and substituted heteroaryl; and
R¹⁰ is —OR¹³; wherein R¹³ is hydrogen or alkyl.

33. The compound of claim 18, wherein
R², R³, and R⁴ are hydrogen;
R¹⁴ and R¹⁵ taken together with the carbon atoms to which they are attached form a 5- or 6-membered aryl or substituted aryl;
R¹⁶ is selected from the group consisting of hydrogen, substituted alkyl, alkoxy, aryl, substituted aryl, heteroaryl, and substituted heteroaryl;
R¹⁷ is selected from the group consisting of hydrogen, and alkoxy; and
R¹⁰ is —OR¹³; wherein R¹³ is hydrogen.

34. The compound of claim 18, wherein
R², R³, and R⁴ are hydrogen;
R¹⁴ is selected from the group consisting of hydrogen, and alkoxy;
R¹⁵ is selected from the group consisting of hydrogen, substituted alkyl, alkoxy, aryl, substituted aryl, heteroaryl, and substituted heteroaryl;
R¹⁶ and R¹⁷ taken together with the carbon atoms to which they are attached form a 5- or 6-membered aryl or substituted aryl; and
R¹⁰ is —OR¹³; wherein R¹³ is hydrogen.

35. A compound selected from the group consisting of
[(4-hydroxy-7-methoxy-2-oxo-2H-thiochromene-3-carbonyl)-amino]-acetic acid;
[(4-hydroxy-6,7-dimethoxy-2-oxo-2H-thiochromene-3-carbonyl)-amino]-acetic acid;
{[4-hydroxy-7-(4-methoxy-phenyl)-2-oxo-2H-thiochromene-3-carbonyl]-amino}-acetic acid;
{[4-hydroxy-7-(3-methoxy-phenyl)-2-oxo-2H-thiochromene-3-carbonyl]-amino}-acetic acid;
{[4-hydroxy-7-(2-methoxy-phenyl)-2-oxo-2H-thiochromene-3-carbonyl]-amino}-acetic acid;
{[7-(3,5-dichloro-phenyl)-4-hydroxy-2-oxo-2H-thiochromene-3-carbonyl]-amino}-acetic acid;
{[4-hydroxy-2-oxo-7-(4-trifluoromethyl-phenyl)-2H-thiochromene-3-carbonyl]-amino}-acetic acid;
[(4-hydroxy-2-oxo-7-phenyl-2H-thiochromene-3-carbonyl)-amino]-acetic acid;
{[7-(4-fluoro-phenyl)-4-hydroxy-2-oxo-2H-thiochromene-3-carbonyl]-amino}-acetic acid;
[(4-hydroxy-2-oxo-7-pyrimidin-5-yl-2H-thiochromene-3-carbonyl)-amino]-acetic acid;
[(4-hydroxy-2-oxo-7-pyridin-3-yl-2H-thiochromene-3-carbonyl)-amino]-acetic acid, sodium salt;
{[7-(5-fluoro-pyridin-3-yl)-4-hydroxy-2-oxo-2H-thiochromene-3-carbonyl]-amino}-acetic acid;
{[7-(3-chloro-4-fluoro-phenyl)-4-hydroxy-2-oxo-2H-thiochromene-3-carbonyl]-amino}-acetic acid;
[(4-hydroxy-7-naphthalen-2-yl-2-oxo-2H-thiochromene-3-carbonyl)-amino]-acetic acid;
[(4-hydroxy-2-oxo-7-p-tolyl-2H-thiochromene-3-carbonyl)-amino]-acetic acid;
[(7-benzyl-4-hydroxy-2-oxo-2H-thiochromene-3-carbonyl)-amino]-acetic acid;
[(1-hydroxy-3-oxo-3H-4-thia-phenanthrene-2-carbonyl)-amino]-acetic acid;
[(1-hydroxy-3-oxo-3H-benzo[f]thiochromene-2-carbonyl)-amino]-acetic acid;
[(7-butoxy-4-hydroxy-2-oxo-2H-thiochromene-3-carbonyl)-amino]-acetic acid;
{[7-(3,5-bis-trifluoromethyl-phenyl)-4-hydroxy-2-oxo-2H-thiochromene-3-carbonyl]-amino}-acetic acid;
{[7-(3-fluoro-phenyl)-4-hydroxy-2-oxo-2H-thiochromene-3-carbonyl]-amino}-acetic acid;
2-(S)-{[7-(3-fluoro-phenyl)-4-hydroxy-2-oxo-2H-thiochromene-3-carbonyl]-amino}-propionic acid;
{[4-hydroxy-2-oxo-7-(2-trifluoromethyl-phenyl)-2H-thiochromene-3-carbonyl]-amino}-acetic acid;
{[6-(3,5-bis-trifluoromethyl-phenyl)-4-hydroxy-2-oxo-2H-thiochromene-3-carbonyl]-amino}-acetic acid;
{[4-hydroxy-2-oxo-6-(2-trifluoromethyl-phenyl)-2H-thiochromene-3-carbonyl]-amino}-acetic acid;
{[4-hydroxy-6-(4-methoxy-phenyl)-2-oxo-2H-thiochromene-3-carbonyl]-amino}-acetic acid;
{[6-(2-chloro-phenyl)-4-hydroxy-2-oxo-2H-thiochromene-3-carbonyl]-amino}-acetic acid;
{[6-(3-fluoro-phenyl)-4-hydroxy-2-oxo-2H-thiochromene-3-carbonyl]-amino}-acetic acid;
{[6-(4-fluoro-phenyl)-4-hydroxy-2-oxo-2H-thiochromene-3-carbonyl]-amino}-acetic acid;
{[4-hydroxy-6-(2-methoxy-phenyl)-2-oxo-2H-thiochromene-3-carbonyl]-amino}-acetic acid;
{[4-hydroxy-2-oxo-6-(4-trifluoromethoxy-phenyl)-2H-thiochromene-3-carbonyl]-amino}-acetic acid;
[(6-benzoylamino-4-hydroxy-2-oxo-2H-thiochromene-3-carbonyl)-amino]-acetic acid;
[(8-benzyl-4-hydroxy-2-oxo-2H-thiochromene-3-carbonyl)-amino]-acetic acid;
{[8-(3,5-bis-trifluoromethyl-phenyl)-4-hydroxy-2-oxo-2H-thiochromene-3-carbonyl]-amino}-acetic acid;
{[4-hydroxy-8-(2-methyl-5-trifluoromethyl-2H-pyrazol-3-yl)-2-oxo-2H-thiochromene-3-carbonyl]-amino}-acetic acid;
[(4-hydroxy-2-oxo-8-pyridin-3-yl-2H-thiochromene-3-carbonyl)-amino]-acetic acid;
[(4-hydroxy-2-oxo-8-phenyl-2H-thiochromene-3-carbonyl)-amino]-acetic acid;
[(7-cyclopropyl-4-hydroxy-2-oxo-2H-thiochromene-3-carbonyl)-amino]-acetic acid;
{[4-hydroxy-7-(2-methyl-5-trifluoromethyl-2H-pyrazol-3-yl)-2-oxo-2H-thiochromene-3-carbonyl]-amino}-acetic acid;
2-(S)-{[4-hydroxy-7-(2-methyl-5-trifluoromethyl-2H-pyrazol-3-yl)-2-oxo-2H-thiochromene-3-carbonyl]-amino}-propionic acid;
[(6-benzyloxy-4-hydroxy-2-oxo-2H-thiochromene-3-carbonyl)-amino]-acetic acid;
[(6-cyclohexylmethoxy-4-hydroxy-2-oxo-2H-thiochromene-3-carbonyl)-amino]-acetic acid; and
and [(6-hexyloxy-4-hydroxy-2-oxo-2H-thiochromene-3-carbonyl)-amino]-acetic acid;
or a pharmaceutically acceptable salt, single stereoisomer, mixture of stereoisomers, or tautomer thereof.

36. A pharmaceutical composition comprising one or more compounds of claim 1 or 18 and a pharmaceutically acceptable excipient.

37. The composition of claim 36 further comprising at least one additional therapeutic agent selected from the group consisting of vitamin $B_{12}$, folic acid, ferrous sulfate, recombinant human erythropoietin, and an erythropoiesis stimulating agent (ESA).

\* \* \* \* \*

SEQUENCE LISTING

```
<160> NUMBER OF SEQ ID NOS: 2

<210> SEQ ID NO 1
<211> LENGTH: 6
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Any amino acid

<400> SEQUENCE: 1

Leu Xaa Xaa Leu Ala Pro
1               5

<210> SEQ ID NO 2
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Methoxycoumarin-Asp
```

```
<220> FEATURE:
<221> NAME/KEY: misc_feature
<222> LOCATION: (19)..(19)
<223> OTHER INFORMATION: /note="C-term amidated"

<400> SEQUENCE: 2

Asp Leu Asp Leu Glu Ala Leu Ala Pro Tyr Ile Pro Ala Asp Asp
1               5                   10                  15

Phe Gln Leu
```